(12) United States Patent
Merkulov et al.

(10) Patent No.: US 6,387,680 B1
(45) Date of Patent: May 14, 2002

(54) ISOLATED HUMAN LIPASE PROTEINS, NUCLEIC ACID MOLECULES ENCODING HUMAN LIPASE PROTEINS, AND USES THEREOF

(75) Inventors: Gennady V. Merkulov, Baltimore; Karen A. Ketchum, Germantown; Valentina Di Francesco, Rockville; Ellen M. Beasley, Darnestown, all of MD (US)

(73) Assignee: PE Corporation (NY), Norwalk, CT (US)

( * ) Notice: Subject to any disclaimer, the term of this patent is extended or adjusted under 35 U.S.C. 154(b) by 0 days.

(21) Appl. No.: 09/820,001

(22) Filed: Mar. 29, 2001

(51) Int. Cl.[7] .................. C12N 9/20; C12N 1/20; C12N 15/00; C07H 21/04

(52) U.S. Cl. ................. 435/198; 435/252.3; 435/320.1; 536/23.2

(58) Field of Search .................. 435/198, 252.3, 435/320.1; 536/23.2

*Primary Examiner*—Ponnathapuachuta Murthy
*Assistant Examiner*—Yong Pak
(74) *Attorney, Agent, or Firm*—Celera Genomics; Robert A. Millman; Lin Sun-Hoffman

(57) ABSTRACT

The present invention provides amino acid sequences of peptides that are encoded by genes within the human genome, the lipase peptides of the present invention. The present invention specifically provides isolated peptide and nucleic acid molecules, methods of identifying orthologs and paralogs of the lipase peptides, and methods of identifying modulators of the lipase peptides.

11 Claims, 37 Drawing Sheets

```
  1 CTCTTACTCT TCAGCCTGAT GTCAAAAGCA AAAGTTCAGA AGTTCCTCAT
 51 CAATAAGGAG TCCTTGTGAG CAGGTGAAGC TCATCTAACT AGGCATTTCT
101 ATGATGTGGC TGCTTTTAAC AACAACTTGT TTGATCTGTG GAACTTTAAA
151 TGCTGGTGGA TTCCTTGATT TGGAAAATGA AGTGAATCCT GAGGTGTGGA
201 TGAATACTAG TGAAATCATC ATCTACAATG GCTACCCCAG TGAAGAGTAT
251 GAAGTCACCA CTGAAGATGG GTATATACTC CTTGTCAACA GAATTCCTTA
301 TGGGCGAACA CATGCTAGGA GCACAGGTCC CCGGCCAGTT GTGTATATGC
351 AGCATGCCCT GTTTGCAGAC AATGCCTACT GGCTTGAGAA TTATGCCAAT
401 GGAAGCCTTG GATTCCTTCT AGCAGATGCA GGTTATGATG TATGGATGGG
451 AAACAGTCGG GGAAACACTT GGTCAAGAAG ACACAAAACA CTCTCAGAGA
501 CAGATGAGAA ATTCTGGGCC TTTAGTTTTG ATGAAATGGC CAAATATGAT
551 CTCCCAGGAG TAATAGACTT CATTGTAAAT AAAACTGGTC AGGAGAAATT
601 GTATTTCATT GGACATTCAC TTGGCACTAC AATAGGGTTT GTAGCCTTTT
651 CCACCATGCC TGAACTGGCA CAAAGAATCA AAATGAATTT TGCCTTGGGT
701 CCTACGATCT CATTCAAATA TCCCACGGGC ATTTTTACCA GGTTTTTTCT
751 ACTTCCAAAT TCCATAATCA AGGCTGTTTT TGGTACCAAA GGTTTCTTTT
801 TAGAAGATAA GAAAACGAAG ATAGCTTCTA CCAAAATCTG CAACAATAAG
851 ATACTCTGGT TGATATGTAG CGAATTTATG TCCTTATGGG CTGGATCCAA
901 CAAGAAAAAT ATGAATCAGA GTCGAATGGA TGTGTATATG TCACATGCTC
951 CCACTGGTTC ATCAGTACAC AACATTCTGC ATATAAAACA GCTTTACCAC
1001 TCTGATGAAT TCAGAGCTTA TGACTGGGGA AATGACGCTG ATAATATGAA
1051 ACATTACAAT CAGAGTCATC CCCCTATATA TGACCTGACT GCCATGAAAG
1101 TGCCTACTGC TATTTGGGCT GGTGGACATG ATGTCCTCGG AACACCCCAG
1151 GATGTGGCCA GGATACTCCC TCAAATCAAG AGTCTTTCAT TAGTGCTAAG
1201 CCTATTGCCA GAATGGGAAC CCACCTTTGA TTTTGTCTGG GGCCTTGATG
1251 CCCCTCAACG GATGTTCAGT GGAAATCATA ACCTTTAATG AAGGCATATT
1301 TCCTAAATGC CAATGCATTT TACCTTTTTC AATTTAAAGG TTGGTTTCCA
1351 AAGCCCTTAC
(SEQ ID NO: 1)

FEATURES:
5'UTR:       1 - 100
Start Codon: 101
Stop Codon:  1286
3'UTR:       1289

Homologous proteins:
Top 10 BLAST Hits:
CRA|18000004922653 /altid=gi|7434997  /def=pir||G01416 lysosomal...   431 e-120
CRA|18000004903706 /altid=gi|542751   /def=pir||S41408 lysosomal ...  430 e-119
CRA|18000004924799 /altid=gi|4557721  /def=ref|NP_000226.1| lipa...   428 e-119
CRA|98000043616611 /altid=gi|12844223 /def=dbj|BAB26283.1| (AKO...    415 e-115
CRA|98000043617058 /altid=gi|12845127 /def=dbj|BAB26629.1| (AKO...    415 e-115
CRA|98000043616593 /altid=gi|12844194 /def=dbj|BAB26272.1| (AKO...    414 e-115

CRA|98000043617174 /altid=gi|12845372 /def=dbj|BAB26725.1| (AKO...    414 e-115
CRA|98000043617140 /altid=gi|12845298 /def=dbj|BAB26697.1| (AKO...    414 e-115
CRA|98000043617224 /altid=gi|12845477 /def=dbj|BAB26766.1| (AKO...    414 e-114
CRA|98000043616955 /altid=gi|12844939 /def=dbj|BAB26556.1| (AKO...    414 e-114

EST:
gi|8003062 /dataset=dbest /taxon=960...   62 4e-07
gi|8000757 /dataset=dbest /taxon=960...   54 9e-05

EXPRESSION INFORMATION FOR MODULATORY USE:
gi|8003062 Stomach normal
gi|8000757 Stomoach normal Tissue expression:
Human leukocyte
```

```
   1 CTCTTACTCT TCAGCCTGAT GTCAAAAGCA AAAGTTCAGA AGTTCCTCAT
  51 CAATAAGGAG TCCTTGTGAG CAGGTGAAGC TCATCTAACT AGGCATTTCT
 101 ATGATGTGGC TGCTTTTAAC AACAACTTGT TTGATCTGTG GAACTTTAAA
 151 TGCTGGTGGA TTCCTTGATT TGGAAAATGA AGTGAATCCT GAGGTGTGGA
 201 TGAATACTAG TGAAATCATC ATCTACAATG GCTACCCCAG TGAAGAGTAT
 251 GAAGTCACCA CTGAAGATGG GTATATACTC CTTGTCAACA GAATTCCTTA
 301 TGGGCGAACA CATGCTAGGA GCACAGGTCC CCGGCCAGTT GTGTATATGC
 351 AGCATGCCCT GTTTGCAGAC AATGCCTACT GGCTTGAGAA TTATGCCAAT
 401 GGAAGCCTTG GATTCCTTCT AGCAGATGCA GGTTATGATG TATGGATGGG
 451 AAACAGTCGG GGAAACACTT GGTCAAGAAG ACACAAAACA CTCTCAGAGA
 501 CAGATGAGAA ATTCTGGGCC TTTAGTTTTG ATGAAATGGC CAAATATGAT
 551 CTCCCAGGAG TAATAGACTT CATTGTAAAT AAAACTGGTC AGGAGAAATT
 601 GTATTTCATT GGACATTCAC TTGGCACTAC AATAGGGTTT GTAGCCTTTT
 651 CCACCATGCC TGAACTGGCA CAAAGAATCA AAATGAATTT TGCCTTGGGT
 701 CCTACGATCT CATTCAAATA TCCCACGGGC ATTTTTACCA GGTTTTTTCT
 751 ACTTCCAAAT TCCATAATCA AGGCTGTTTT TGGTACCAAA GGTTTCTTTT
 801 TAGAAGATAA GAAAACGAAG ATAGCTTCTA CCAAAATCTG CAACAATAAG
 851 ATACTCTGGT TGATATGTAG CGAATTTATG TCCTTATGGG CTGGATCCAA
 901 CAAGAAAAAT ATGAATCAGA GTCGAATGGA TGTGTATATG TCACATGCTC
 951 CCACTGGTTC ATCAGTACAC AACATTCTGC ATATAAAACA GCTTTACCAC
1001 TCTGATGAAT TCAGAGCTTA TGACTGGGGA AATGACGCTG ATAATATGAA
1051 ACATTACAAT CAGAGTCATC CCCTATATA TGACCTGACT GCCATGAAAG
1101 TGCCTACTGC TATTTGGGCT GGTGGACATG ATGTCCTCGG AACACCCCAG
1151 GATGTGGCCA GGATACTCCC TCAAATCAAG AGTCTTTCAT TAGTGCTAAG
1201 CCTATTGCCA GAATGGGAAC CCACCTTTGA TTTTGTCTGG GGCCTTGATG
1251 CCCCTCAACG GATGTTCAGT GGAAATCATA ACCTTTAATG AAGGCATATT
1301 TCCTAAATGC CAATGCATTT TACCTTTTTC AATTTAAAGG TTGGTTTCCA
1351 AAGCCCTTAC
(SEQ ID NO: 1)
```

FEATURES:
5'UTR:        1 - 100
Start Codon:  101
Stop Codon:   1286
3'UTR:        1289

Homologous proteins:
Top 10 BLAST Hits:
CRA|18000004922653 /altid=gi|7434997 /def=pir||G01416 lysosomal...    431  e-120
CRA|18000004903706 /altid=gi|542751 /def=pir||S41408 lysosomal ...    430  e-119
CRA|18000004924799 /altid=gi|4557721 /def=ref|NP_000226.1| lipa...    428  e-119
CRA|98000043616611 /altid=gi|12844223 /def=dbj|BAB26283.1| (AKO...    415  e-115
CRA|98000043617058 /altid=gi|12845127 /def=dbj|BAB26629.1| (AKO...    415  e-115
CRA|98000043616593 /altid=gi|12844194 /def=dbj|BAB26272.1| (AKO...    414  e-115

FIG.1A

```
CRA|98000043617174 /altid=gi|12845372 /def=dbj|BAB26725.1| (AKO...    414   e-115
CRA|98000043617140 /altid=gi|12845298 /def=dbj|BAB26697.1| (AKO...    414   e-115
CRA|98000043617224 /altid=gi|12845477 /def=dbj|BAB26766.1| (AKO...    414   e-114
CRA|98000043616955 /altid=gi|12844939 /def=dbj|BAB26556.1| (AKO...    414   e-114
```

EST:
```
gi|8003062 /dataset=dbest /taxon=960...                                62   4e-07
gi|8000757 /dataset=dbest /taxon=960...                                54   9e-05
```

EXPRESSION INFORMATION FOR MODULATORY USE:
gi|8003062 Stomach normal
gi|8000757 Stomoach normal Tissue expression:
Human leukocyte

FIG.1B

```
  1 MMWLLLTTTC LICGTLNAGG FLDLENEVNP EVWMNTSEII IYNGYPSEEY
 51 EVTTEDGYIL LVNRIPYGRT HARSTGPRPV VYMQHALFAD NAYWLENYAN
101 GSLGFLLADA GYDVWMGNSR GNTWSRRHKT LSETDEKFWA FSFDEMAKYD
151 LPGVIDFIVN KTGQEKLYFI GHSLGTTIGF VAFSTMPELA QRIKMNFALG
201 PTISFKYPTG IFTRFFLLPN SIIKAVFGTK GFFLEDKKTK IASTKICNNK
251 ILWLICSEFM SLWAGSNKKN MNQSRMDVYM SHAPTGSSVH NILHIKQLYH
301 SDEFRAYDWG NDADNMKHYN QSHPPIYDLT AMKVPTAIWA GGHDVLGTPQ
351 DVARILPQIK SLSLVLSLLP EWEPTFDFVW GLDAPQRMFS GNHNL
    (SEQ ID NO: 2)
```

FEATURES:
Functional domains and key regions:
[1] PDOC00001 PS00001 ASN_GLYCOSYLATION
N-glycosylation site Number of matches: 5
    1    35-38  NTSE
    2   100-103 NGSL
    3   160-163 NKTG
    4   272-275 NQSR
    5   320-323 NQSH

---

[2] PDOC00005 PS00005 PKC_PHOSPHO_SITE
Protein kinase C phosphorylation site

Number of matches: 4
    1   125-127 SRR
    2   204-206 SFK
    3   243-245 STK
    4   266-268 SNK

---

[3] PDOC00006 PS00006 CK2_PHOSPHO_SITE
Casein kinase II phosphorylation site

Number of matches: 8
    1    53-56  TTED
    2   130-133 TLSE
    3   132-135 SETD
    4   142-145 SFDE
    5   162-165 TGQE
    6   185-188 TMPE
    7   274-277 SRMD
    8   348-351 TPQD

---

FIG. 2A

[4] PDOC00007 PS00007 TYR_PHOSPHO_SITE
Tyrosine kinase phosphorylation site

```
        161-168 KTGQEKLY
```
------------------------------------------------
[5] PDOC00008 PS00008 MYRISTYL
N-myristoylation site Number of matches: 4
```
    1       14-19   GTLNAG
    2      117-122  GNSRGN
    3      121-126  GNTWSR
    4      175-180  GTTIGF
```
------------------------------------------------
[6] PDOC00110 PS00120 LIPASE_SER
Lipases, serine active site

```
        167-176 LYFIGHSLGT
```

Membrane spanning structure and domains:
```
Helix  Begin   End   Score  Certainty
   1       3    23   1.398  Certain
   2     167   187   1.637  Certain
   3     248   268   0.715  Putative
```

BLAST Alignment to Top Hit:
>CRA|18000004903706 /altid=gi|542751 /def=pir||S41408 lysosomal acid
        lipase (EC 3.1.1.-) / sterol esterase (EC 3.1.1.13)
        precursor - human /org=human /taxon=9606 /dataset=nraa
        /length=399
        Length = 399

Score = 430 bits (1094), Expect = e-119
  Identities = 211/394 (53%), Positives = 274/394 (68%), Gaps = 2/394 (0%)

Query:  2   MWLLLTTTCLICGTLNAGGFLDLENEVNPEVWMNTSEIIIYNGYPSEEYEVTTEDGYILL 61
            M  L    CL+  TL++ G     V+PE  MN SEII Y G+PSEEY V TEDGYIL
Sbjct:  3   MRFLGLVVCLVLWTLHSEGSGGKLTAVDPETNMNVSEIISYWGFPSEEYLVETEDGYILC 62

Query: 62   VNRIPYGRTHARSTGPRPVVVYMQHALFADNAYWLENYANGSLGFLLADAGYDVWMGNSRG 121
            +NRIP+GR +     GP+PVV+++QH L  AD++  W+ N AN SLGF+LADAG+DVWMGNSRG
Sbjct: 63   LNRIPHGRKNHSDKGPKPVVFLQHGLLADSSNWVTNLANSSLGFILADAGFDVWMGNSRG 122
```

FIG.2B

```
Query:  122 NTWSRRHKTLSETDEKFWAFSFDEMAKYDLPGVIDFIVNKTGQEKLYFIGHSLGTTIGFV 181
             NTWSR+HKTLS + ++FWAFS+DEMAKYDLP  I+FI+NKTGQE++Y++GHS GTTIGF+
Sbjct:  123 NTWSRKHKTLSVSQDEFWAFSYDEMAKYDLPASINFILNKTGQEQVYYVGHSQGTTIGFI 182

Query:  182 AFSTMPELAQRIKMNFALGPTISFKYPTGIFTRFFLLPNSIIKAVFGTKGFFLEDKKTKI 241
             AFS +PELA+RIKM FALGP  S  + T   +     LP+ +IK +FG K F +    K
Sbjct:  183 AFSQIPELAKRIKMFFALGPVASVAFCTSPMAKLGRLPDHLIKDLFGDKEFLPQSAFLKW 242

Query:  242 ASTKICNNKILWLICSEFMSLWAGSNKKNMNQSRMDVYMSHAPTGSSVHNILHIKQLYHS 301
                 T +C + IL +C       L  G N++N+N SR+DVY +H+P G+SV N+LH  Q
Sbjct:  243 LGTHVCTHVILKELCGNLCFLLCGFNERNLNMSRVDVYTTHSPAGTSVQNMLHWSQAVKF 302

Query:  302 DEFRAYDWGNDADNMKHYNQSHPPIYDLTAMKVPTAIWAGGHDVLGTPQDVARILPQIKS 361
                +F+A+DWG+ A N   HYNQS+PP Y++  M VPTA+W+GGHD L    DV  +L QI +
Sbjct:  303 QKFQAFDWGSSAKNYFHYNQSYPPTYNVKDMLVPTAVWSGGHDWLADVYDVNILLTQITN 362

Query:  362 LSLVLSLLPEWEPTFDFVWGLDAPQRMFSGNHNL 395
             L   S +PEWE   DF+WGLDAP R+++   NL
Sbjct:  363 LVFHES-IPEWE-HLDFIWGLDAPWRLYNKIINL 394 (SEQ ID NO: 4)

Hmmer search results (Pfam):
Scores for sequence family classification (score includes all domains):
Model      Description                                        Score    E-value  N
--------   -----------                                        -----    -------  ---
PF00561    alpha/beta hydrolase fold                           46.7    2.5e-13  2

Parsed for domains:
Model      Domain  seq-f  seq-t    hmm-f  hmm-t       score  E-value
--------   ------  -----  -----    -----  -----       -----  -------
PF00561    1/2      112    195 ..      1     71 [.     38.8  6.7e-11
PF00561    2/2      294    352 ..    139    196 ..      8.0     0.19
```

FIG. 2C

```
Hmmer search results (Pfam):
Scores for sequence family classification (score includes all domains):
Model      Description                                          Score    E-value    N
--------   -----------                                          -----    -------    ---
PF00561    alpha/beta hydrolase fold                            46.7     2.5e-13    2

Parsed for domains:
Model      Domain    seq-f  seq-t      hmm-f  hmm-t       score   E-value
--------   ------    -----  -----      -----  -----       -----   -------
PF00561    1/2       112    195   ..       1     71  [.    38.8   6.7e-11
PF00561    2/2       294    352   ..     139    196  ..     8.0     0.19
```

FIG. 2D

```
   1 TTATGGCCTA ACCTTTTTAA CTTTGAGTTA TTTTCAAGAG AAAATTTGAA
  51 AAAGCAGCCT TGAGGAGAA AGAAGCAATC CAACAAACAA AAAGATAACC
 101 ACACTGTAAT AGGAAATGTG TTTTGAATAG GACATTGGAA GAAAAATAAT
 151 AATCATTTTT ACAGGTAGAT CCCAAAGTCA AGGATCTATG TTCAACCATG
 201 TGTGTTCCAC CATCTTCACA ATTGAATGAG TAACCATCAT TAAGCAGTTA
 251 GCTTAGGCCG TAATATGATT CTTGGACTGA GATTTCAAAA ATACCACAGG
 301 CCTTCTGAAA GGTTACCCCT TTCTAGCTCC ACTATCATCT AATTTTATTA
 351 AAAAAAAAAA AAAAGGAAAA ATTTGAGCTT CTAGAGAGTA GGGGCTACCA
 401 TTTTGTATCC CACAGGGCCA AGGAACAAGT TTTAATGTAT TCATTTAAAT
 451 TAATTTCAGT ATGAGTATTG AAATATATAA TAGAAATATT GTAACATTAT
 501 ATATTTTCTA TATACTTTTA TTATATAGAA AATATATATT ACAGAATATA
 551 TTATTAAATA TTGTAGAACA ATATATAATA CAGAAAAATA TATAATACTC
 601 AGTAATATAT TAAATACTTA TTAAAATAGC AAGCTTATAT AGGAAGAGTG
 651 ATGGAGCATT GTGAGAAAGT TTCAGCTTTA TTTCTTTGAC ATTACTTTGT
 701 TTCTGCACAA ACAAAAGAAT TACAGGAATT GTCCAGATTA TTCAAATAAC
 751 TCGAAGTTGA GGAGGGAATA TAAGTCAATG ATGTAGAAAC TCTTTTAAGA
 801 TTTGAGCTAG CCTACAATCT GTAAAGATCT GTGAAATTGA ACTATATTTG
 851 TGCTATTTCC ATATTAAGTC AAGGCAACAA ATCAATATTA ATAATAATAA
 901 CATAGCACTT CTAGAACTTT CTAAAGAGTC AATAAAGTT TTGTTAGAAA
 951 GGATTGTTTT TGAAGTTAAA AACCATGAGA AATTCCAGGA AAATCCACAT
1001 ACCTATGCCA TCATACTATC AATCAGGGCA AAACATGCTT GAGTCTTTCA
1051 TCAAGACTAA ATGATTAAGG AGTGGTACAT AACTTTTCCC TGTTCTGACT
1101 AGCTGAACAC TTCCTTTTAC TCCACATTTG TTTAATTGGC ATGAAATTTC
1151 CCACTCCACT AAAACAGATC TTAGGATTTG GACAACACAA AATATCATTT
1201 GTTTTGAAAG GATTTGAGGA TAAATCCAAA CTAATAGAAC TGAAACTTCT
1251 ATATTATGCT GGGTAGCAAC TTAGTTTTCC CTACCCTTCT TCATGCTGGG
1301 AGATGAAAGA GATTCAGTTA CGGCTTAAGC TCCACAGGCA TACAAAGTGA
1351 AGCAGAAAAC TGAGGCACGT GTGCCTCCAT TATCTGGTAT CTCATGTGGG
1401 GCTTAGAGGT AAATTGTCGT TATTTGGCCT CCATTTCTGC CTTTAACCAC
1451 TGGTGTAAAC AAAGGTTACT GTGCCAAAGT TGACAGCAAC CCAAATCCCT
1501 TTGGCATGTG AATTAGTTTC CTCTGCCATA CTGCTAGTTC CAAATTCCTT
1551 CTGGTTTCAG GATTTAGGAG TCAGGGTTGC CTCATCTTCT CAAATGAGTT
1601 ACAGTCACGC ACATCCCTAC ACACTGCATG GTTGGCACTA GTTCCTTGAT
1651 ATATGTTACT CCGTTTGATC CTCATGAAGG ATCAAATGGG GAAGGGAGAT
1701 ACTATTGTCT CTGATTGTCC ATTAAGATCT TGAGTATGTT CTACTTCCCT
1751 GTTTGACACA CTGGTTTGAA AATGTTGCTA AGTCTTCCCA ACAATGACAG
1801 ATACTCAGTG GAAACATGAA GGATTCCGTC AAACTGGTTA TTTTGCATCA
1851 TGTAGACCAC TATTTCCCAA CCTGCAAGTG CATCATGGCC TTTGGTGTGT
1901 CAGGGACACG CCTTGGGTGT GTGTCTCAGT CTAAAGCTTC CTCCTTTTCA
1951 CAAGCTTCCT GTTTCTCATC TCTCTAGCTT CTAACTGTCA CTGTAATCAT
2001 CTCTTACTCT TCAGCCTGAT GTCAAAAGCA AAGTTCAGA AGTTCCTCAT
2051 CAATAAGGAG TCCTTGTGAG CAGGTGAAGC TCATCTAACT AGGTAAGATG
2101 AAGATCTATC ATAACCAGGA GGCAGGTTGG AAGGTGCCAG TTGCACTGGC
2151 AGTCAGGTGC AAGAGCTCTG CAGTGAGGCT GCCTGAGTGT CCATCCTAGA
2201 TCTCTCACCT CTTGGCTCTG TGACCTTGAG CAGGTCTTAA ATCTCTCTAA
```

FIG. 3-1

```
2251 GCCTTTGTTT TTTTAATTGA TAAAATGAGG ATAATAATAG TACCAAAATT
2301 AGGGAGATTT TCAGAGCTTA AATAACATAC GTGAACTATT TAGAGTAATG
2351 CCTGCCATAA GGGGACTCAG TAGCTTATTA TTAGTTTCAT ACAATTTGAA
2401 AAGTTTCATA ATATTTGCAG ATATAAGATG ATCTTCAACC AGATAGCTAA
2451 TGTATGCAAA GCTATTTAGC TTCAGAAGTA AACTCTGCAT TTCTAGAAGT
2501 TAAATATTAC TTTGTTATAG TGAATTATCT GTAATATTTA TCTCTTGCTC
2551 ACTTTTATAA GAAAAATAGT GAAAGCATTT ATTAAGAACT TACACTGCAC
2601 TAAATGTTAT ATATGACTTA ATCCTCACTA TAACCCTATG AGATAGGTTA
2651 CATTATTGTC CTAATTTTAC TAACAAGGAA ACCAAGAGAC AAAGCTACTA
2701 AAACACTTGC CTGAGGTTAG ACATCTTCTT CTGTGGTGAG GCTGGATTTC
2751 AAATTTAGAC CATTTGACTG TAGCACTTAT ATGATGAGCA TGCTGTTTAG
2801 TGTTATAGTG TTGGTCTACC TTTGAATAGA CATACTTTTA AACCATGGCA
2851 AGGAAGTGAG ACTGCACATT GAAATATGTA AAATTTGCCT TTGGGTGCCA
2901 CGTGAGAAAT AGTCACATCA CTAGAAACTA ATCATAAGCT TTTGTGTTTG
2951 GTTAAAGTTT TATTGATCCA TTTTTCTTGT TTACTTTGTG GGATACTGGG
3001 CTTAACTAGG GGATACCTCC ACTTTTTACT TGGCCATGGT ATGAAAACCT
3051 GTCCTCTGAA TCTTTAGATA TTTTGGCAAA TTGTAGGCAA ACAAAGACTT
3101 AAAGCAATTC AACCTTGATT AAAATAAGAC CAAAAATGCC TCCATACTTG
3151 ATTAAATTTA TTTCATTTTA GGAACTGGAT TATAATCAAG ACAACTTCTA
3201 CATGAAAAAA TAGATTAATA GTGCTCCAAG TTAGTTCACT GTATTTATTC
3251 CTTTTTATAC ATTATCTGCC TTCGGTGTTA TTCAAGTTTT CATTAATCAT
3301 TAATAATTTC ACTAATCATT TTATTTCATT AATCAACATT GATAGTTAAA
3351 ATTAATCTGT GAATATTAAA TGTTTTATGC CAGGCATTTC TATGATGTGG
3401 CTGCTTTTAA CAACAACTTG TTTGATCTGT GGAACTTTAA ATGCTGGTGG
3451 ATTCCTTGAT TTGGAAAATG AAGTGAATCC TGAGGTGTGG ATGAATACTG
3501 TAAGTCATGG AAAACTGTGA AGAACATCAA ATAAAGCAGG ACTAATGGAG
3551 TATGAGGTTA CGAAAGGTCC TGTTGTAACA GAAAATCTCT GATAAAACAG
3601 ATAAAATGTA GATGGTTTTT AACCTCTGCA AGAGTCAAGC TAGTTAGATC
3651 TTTGTCTGAA AAACAAATAC TGTCCGGTAA TGAAAACCAA ATTGTGCTAT
3701 TGTGCTATCT ATCTATCTAT CTATCTATCT ATCTATCTAT CTATCTATCT
3751 ATCTATCTAT TTATCTATCT ATCTATAGAT AGAACCTCCT CTTTTGAATT
3801 TATGTTTTAA GAATATCAAG CTATTTGTTG ATATACATGA TTGCCTTCTA
3851 TTGATCTATA GTTCTATTAC TTTTAAAGCA AGAGGGGTCT CAAAAGACAA
3901 TTGACTTGAT AAATATAGCTT TGTCAGAAAG AATGGGTCAA TGCTAAATTT
3951 TCCCCCAACC CCCCAAAATA TTAGCCAATA GTAGATATTT TTTAAAATTC
4001 TACTTATTTT GTATTAAGAC TTTATTTATT AATTTTACAG TTACCTGGT
4051 CTACAAATTT CAGATAATTC ACCCTAATAA GCACACAACA GATGGTTTGT
4101 TTTGATTCCT TTTTATATCC TTTGGAGAAG TTCCACTAAC GACTGTATTT
4151 TTACTGGGCA GAGTGAAATC ATCATCTACA ATGGCTACCC CAGTGAAGAG
4201 TATGAAGTCA CCACTGAAGA TGGGTATATA CTCCTTGTCA ACAGAATTCC
4251 TTATGGGCGA ACACATGCTA GGAGCACAGG TACAAGATAT GTCTCTCCTG
4301 AAAAGGGGAC TGCATTGACC TCCTGCTTCT CAGGAGGAAT TTAATGCTAG
4351 ATATGCATCA ACAGAGTTTA TCAAAATTGG TTTGAATTAT TGGATTAGTC
4401 TTTAAATAGT TATCAGGGAG GCTCACTCTT TGCCTGATAA TTCTCTGAAG
4451 ACAGACAGGA ACCTAAAAAT ACAAACAGCA AGACTGATCT TGCTAACTGC
```

FIG. 3-2

```
4501 AACCAGAGGT ACTTGTTAGG GTGTAAACAG AAAGGCAGAG CCTGCATTTT
4551 GTCACCTCAT TACTGATTTA TCATGTGGAA AATTGCTTTG TCCCAGGAAA
4601 ATGGATCCTC TCATTGTCAG AAGGAGATTT TCTAGGTTGT ATGAAATTGA
4651 CTCTGGGGCA CCCAAGAAGA ACCTCTCCTG CTCCCACTAA AATTAAGGGG
4701 CCTCCCTCTG CAGGATAAAA AACAATCTAG TTAAATGACA ACGCATTTCT
4751 GAAAAGTTTT CCAGGACTGA AAACCTTAAC ATCCACATAC ACTTTGATCT
4801 AAGGGACAGA CGGTTCATAG AATGAAAGAG TATGGTGTCA ATAAGGCTTG
4851 AATTCTAGAA TGAGGAGCCA GCCATGCCAT AGCAGGGGAA TGATACTCCT
4901 TAAAAGGGAA AATTTAACTA CAAATCCTCT GAAGTAGAAA TGATAAGAAT
4951 AACCAAAATA TCTGCAATGG TTCAATAGCA AATAATTTAT TGGCAGCTGC
5001 TTACCGTGTT CATTTTGCAT CTTTTTTCCC ACCACACATA TTAAGGAGCA
5051 GCTGAAGTCA TGTTTGACAT TCTCTCCCTC TTTTATCTCC AGTTTCAGAA
5101 TGAAAAATGA GAGTGAGATA TGAGTAGTTT TACTAGTTAA AATATGAAAC
5151 ACCCAGTTAA ATTTGAAGGT CAGATAAACA ACAAATAATT TTGTATAAGT
5201 CTCATTTTAA GATAATACTA AAAAGTCATT ATTTATTCAC TATTATCACT
5251 ATTTATAAAA TTTTGTAGAG CATCCTGGAT CTTTTTGCTT ACTTTTGTTT
5301 TTATTTTTTG CTAAATCTGG CAATCCCAGG CACATGTGTG AAGGAGCTGT
5351 GAAATATAAA AGGAGAAAAC TTTTATGGGA AAGATTTGGC TTAAGGAGAG
5401 ATAATTTTGG AAAGATTTAG AATTAAAGAT CATTCATTAG ATGTAATGTT
5451 CTAAATACTT TATATCAGTT AAACTTCTCA TCAACAATAT GAGATGGGTA
5501 CCACTAATAG TCACCATTTC ACAAATGATG AAATTAAGGC ACAACCGGTT
5551 ATGTTAAGAG GCCTAAAGTC CACAAATAGC AAGCTGACAG ACCAGAATTT
5601 AAGCCCAGGC ATGCTGGCTC CAGAGCCTGT GCTCTTAGTC ATTAAATTAT
5651 AGTGCCTTAC TTGACCTTCC ACCCTGGTTA CTTTGGATCT CCCTGAATGC
5701 TCTCTCTCCC TCAGAAATAC TGGAAGTTGG CAGAGGGACA CTGAGCTGAG
5751 CATATTATTG TAGTTTTTAA ATGCTCTCCA CTGGACAGAA GATGGGGGAT
5801 TTGAATAGAA ATTTGGTGAG GAACTAATCA GTGTCCATTT ACACTCACCT
5851 CCTCTTCCTC CCTGGAAGAG CTATAGGACT TGAGTAAGCA TGATAAATTT
5901 CGTGTCTTTG TAAACCACAC CCAGGAAATT TGTATATACA AATACATAGA
5951 GCACAGTAGT TATCAGGACA GACTTTGACA TAAAAAGAAC TGGGTTTGAG
6001 TCCCTGCTCT GGCCTTCTTA TCTGGGTGGC CCTCTGGGAA AGTTACTTAA
6051 CTACATAAAG TTTTGTTTCC ATATCTACAA AATGAGGTTT CTCAAAATAG
6101 CAGCTAGTTT ATAGAGTTGT TGCAAGAATT TAGTAAGCTA ATACATATAA
6151 ATACGTCAAC ATAGCACCAG GTACAAAAAT ATGTGCTCAA GAAACTGAAG
6201 TTACCTGATT ATAATGCTCT ATACTATTGA CAAGGGAAAA GTGAAAACAG
6251 TTTTTGTTTT ACCATGTGTG TATGTGTGTG TGTCTGTGAT GTTTCCGACA
6301 TGCTCTATTT AACATAAATT ACTCTCACTC TTTCTCTCTC TCTCTTTCTC
6351 TTTCTCCCTC TCTCATCTTA CCCTTTCCCC CACCAGGTCC CCGGCCAGTT
6401 GTGTATATGC AGCATGCCCT GTTTGCAGAC AATGCCTACT GGCTTGAGAA
6451 TTATGCCAAT GGAAGCCTTG GATTCCTTCT AGCAGATGCA GGTTATGATG
6501 TATGGATGGG AAACAGTCGG GGAAACACTT GGTCAAGAAG ACACAAAACA
6551 CTCTCAGAGA CAGATGAGAA ATTCTGGGCC TTTAGGTAAA TATTAGCTAA
6601 GAAAACTCAA GGGGGAAATT GGAGGCAATT TTAAAAAAAT AACGTGGACG
6651 CTATTAATGA TTATCTTTGA CGCTTGAAGT CATATAGCTC CTTGTAGTTT
6701 CTGTTAAGAT CTCAAAGGAG GGTAACAGCA AGAAGCTCTG ATTTTTCACT
```

FIG. 3-3

```
6751 GATTCTCCCA CAAGCAAAGT ATGGCATTTC AACAAGATCA TTTTTACATC
6801 CAATTCTGTG AATTCTATGC ATTAAAAGTA TGTCCAAAGA GACAGCTCAG
6851 GAAATTATCA TGACCAATGT GCACATTCAT TCAGCCAATG TTTACTGAGT
6901 GGCTACTGTA TGCGCTGTTC TAGGCCCCGA ACATTCAAAC AGGGAACAGA
6951 CAAACTCTGA CCTCACAAAG CTTATGTTCA TTTTAGTGAT AATTTTACAA
7001 GTCATTGCTC CTGGATTGCC AATCAACTGT GTAAAGATGA TTTGGACCAG
7051 GACCTTATTG ATTTAGAGAA ACTGTGATTG ATTTAGAGAA ACTGAGATCG
7101 CACATAGTAC CATTTTCAGG AAAACTCCAA TATTAGATTT TTAAAACCTT
7151 GTTAATGGGC AATGAAGAAG AATCTTTTTT GATATCTTGT TTCTTTTAAT
7201 GGAAGAGTTT TCTGCTGTCA CCAGAGGACA GGCTGATGCC TGCGATAGAC
7251 TTTTCTTTCT TCAGGCCTAA GCTCCCTGTT GGTTTGTAAA CCTGATGCTA
7301 GAACAGACTG TGTATTCCTA TTACATTAAT AAAACATTCA GTACCCACTG
7351 AAAGTTTGAG AATAGTGGAG GAATAGAATA GAATGTTATA GTCTGAGTTC
7401 TTGGGCAGGG GCAAGCATCA GGAAATATTG AATCATTAGT CTTTAGGAGG
7451 TGTCACAACA ATTCTCCTAT TCTTGTAAGT CCCAATCTAT AGATTTCCTC
7501 ACATGTTCTT TTAATAAACA GGCTTCTAGC TTATGGAATA CCTGATTTGA
7551 CTAAATGTTA TATAGGCCCT TTTGTTCCTC CTGTCTGAAG AACAAAATAC
7601 TAGTACTATG GAATATTGGT ATATATTAAA TATATATCTA TATATCCATG
7651 TGGACAGGAA TACTACTACT AACAACATCT TACTGAGCAC CCACTGGCAG
7701 CCAGAGTCGT TTCTTTCATA CTATTAAACC CCGTTAGCAG CCCCGTAAAC
7751 CAGGTACTAC CCTGTTTATT TCCCAAATGA GAAAACATAG GCTCAGAGCA
7801 TTTCAGTAAT TTCTCAAGAG TTGCAAAGGC CATAAATAGT AGAATCATGA
7851 TTTACAAAAC CCCTGTTTCC AAAGATGGGT ATTAAATGGT CCTAACAATT
7901 GTGAAGCCTC ATGTGGGAGT CAGAAGTAGA GGCACACAAG CCAGATGGGG
7951 AAAGGGAGGG CAAAGAAAAG CAAGAGAAGG GAAGGAAGAG GAGGGATCAT
8001 AAGGTTGAAC TTCAAATATC ATACACAAGT TTCGAAAGTG TTCCTCTTAT
8051 AAGGAAGTAA AATGTACATA TGCAGAAAAA CAAAAAGCTA CAATAGCCTA
8101 CATATAATTG GATAAATAAT GAAATACACA TTGAATCTAA GTAAACAGCA
8151 TAGAATCTGG GTGTAAAAAA GAAGTGAGCA AGTGCTCTGA GTTTTAAACT
8201 TAAACTTGCA AGTATTTATA AAAGCCCCTG TTTTATTTTG CAGTTTTGAT
8251 GAAATGGCCA AATATGATCT CCCAGGAGTA ATAGACTTCA TTGTAAATAA
8301 AACTGGTCAG GAGAAATTGT ATTTCATTGG ACATTCACTT GGCACTACAA
8351 TAGGTATGTT TATGAGGGTC ACTGTTAGGT GTGTTTTTGA GGGTCAGTTT
8401 TCTCAGAGTC TTACAGGAGT TCACCTTTAT GTTGGAATAA AACAACTGTT
8451 ACTTATAGTG CCCTCAATTC CCTGTCCTCT GCTGGGAATA ACCCTAGTAC
8501 TCTAAGTAGC TGTGAGCCTG CAGTGCACAG ACTATATGTA GGGCAAACCT
8551 TTCCTGGGTC TCTGGTCACA GCAGCATATT GACTACGGTG ATGCAATTTC
8601 CCAGGAATAA CATGTGTTCC AAATTCAAAG AAATAATTCC ACAGAGTAAG
8651 TTTCTAGATT CCCTCTGAGC TGAAAAAGTA AAATTCAATG CCATGGAATA
8701 TGGCTGAAAC ATAATAAATG TGCATCAATC ATCTCTTTCT CACAACCCAA
8751 ATGGGATTTT TAAAAAATAA AAGGGAAGGG CTTATACCTA TATTTAAACA
8801 AATTGAAAAG GCATGGTTAT ATTTGTTTGT GAGTTGGAAC ACACAAGCTT
8851 ACTATAATAA ATCAATTGAG CTTATCTATT CAGTGTGTGA TTTAGTATTT
8901 ATGAAATAGC AAGTAAATGT AAGCACTATG TAGAAATTTC TAAAGTTTTT
8951 TAAGCTGACA ACTTACTTCT TAATTTACTT ACTTTACTTA ATTTACTTTA
```

FIG. 3-4

```
 9001 CAATTTACTT TCCAGGTATT TTGGAAAGAA ATCAATAATC TAGTTCCAAG
 9051 TAAAAGTTGA AAGGAACCCA CACTAATAAA AGCTTTGAAT TTGTCATTGA
 9101 ACTTCCACTA AAGTTTCCAA TTTTAAGAGA ATAAATCATG TGAAAGTGCA
 9151 ATATTTCAGT TTAGGGAAAT ATTTTCATTA TCACCACTAT CATCAGTAAC
 9201 AAACATATAT TCATTAGTAT TTTAGATTGA CAGGCACTTT CCAAGCTCAG
 9251 AACAGGCAGT TAGCATCAGT CAGCATATAC TAAAAAAGTA TCAAAGAACT
 9301 CATAGGAGAT CAAAAATGCC ACCAATAGGC AAATAATTAC AGTATCTAAC
 9351 ACTTATTGAG CATTCGTTAT GTGTAGGGTC TTGTGTTCAG GACCTTCCCC
 9401 ACAGTATCTC CCTCTGATCT TCAAAACAAC CCGAATGTTA TTATCCCCAT
 9451 CTCATAGAAG AAGAAACACA AGTTCAGAAC ACAGATTCAA ACCAGATGTA
 9501 TCTGATTTCA CCAATAGGGT GTGTAAGGAT TCCGGAGAAA TGGTGTAGAG
 9551 AAGAAGAAAT GACTTTAGTT GGTTTTGGAA AGTGGGTAGG ACTTAGATAT
 9601 GCTCTTATAC TTGATCTGCA AAAAAAAAAA AAAAAACCAT GGAGAATTTG
 9651 ATTATCTGTG CTCTGTGTTT CATTTAGGAC ATAAATATTT TTAGTGACTG
 9701 TTGTTTGCAT TTTGGACAGA GCAATTTCTG TTATGTAAGG AGCACCCACT
 9751 CTTTGTAGGA CATTTAGTAG GTCCCAGCCC ATTAAACAGG GCTCTGCAGT
 9801 CAGCGTGACC CTCAAAAATC TCACCTCCAC ACATTTCCAA ACACCCTCTG
 9851 GGGAAGTACT ATTCCTGATT CAGAGTCTTT TTATCAATTG TTCAGTCAAT
 9901 TATTTCAGTT CTTCTTTTTC TGGCCAAGAC AGTTTTAATG TTCCAACAAG
 9951 TGTTTCAGTA CACACATACA CACACACACA CACACACACA CACACACACA
10001 CACATGCTAG TGGAGGCCCA GGAAGGGACC TCTGGAAACC AAATTATATG
10051 GATATTCTCC CTAGCCTACC CAGTGTTGTG CTAATCTCCA TCCTCACAGA
10101 TATACAAAGG GGTGCAATGC TACTGCTGAA AGAGCAAAGC AAATGGAGAT
10151 GCCTGGTCCT TACTGGGCCA TCGTGGATGC TAGGGAAAGC CCCTTTCTTT
10201 TTGGAAACAG GGAAGAGTCT AGAGGGTTGA AAAACACCCA GTAAGACACT
10251 GGGAGCAGTG AAATTTCATT CCATAGTGAG AAAGAAAACC TGTTAGAATA
10301 ACTGGGTGAT GCTGCAGAAA GAAATCAATT CACCTCCTGT GACTGATTAT
10351 TTGCTTCTGG AAGCTCTGTG ATTCATTCTG GCATCTCAGA GTTAGGGATG
10401 AAATGAGAAT GTTGCCAGCA TTTACCCCAT GCTTGGGAAG TTTACACAGC
10451 AGTAGCTACT CCAGCAGCTT AACCATCACC TTTCCCCTGC CAACTACTCC
10501 ATTTCCCCCA ATCAAGTCAA ACTGTCCATA AATAGAATAA AATAAAATTG
10551 GAGACTTGAG AGCAGAGAAG ACTGAAGGCA GATTATCTTT ATAGAATAAC
10601 TCAGAAGACT TCCAATTCAT CCCCAGTATG ATCACGATAG AAGGAAAAAA
10651 TGACTAAGCA GAGCCCCAAT TTGTTAGAA ACATTGCGTA AGTATTTATT
10701 TTTACAAGAT TGTCTTATCT CCTGTTCTCT CAGGGTTTGT AGCCTTTTCC
10751 ACCATGCCTG AACTGGCACA AAGAATCAAA ATGAATTTTG CCTTGGGTCC
10801 TACGATCTCA TTCAAATATC CCACGGGCAT TTTTACCAGG TTTTTTCTAC
10851 TTCCAAATTC CATAATCAAG GTAGGCTCCT TTCAACAAAA TGTACCTGAG
10901 GATCTCATTT TGGATCATAA ATCCTTATTA TTTTCAAATC TACTGTAAAG
10951 TAAAAGTAGG AAATTTAGAT AAAATCTATA GAACTTAGAC TCTGTGGGTA
11001 TGTGCTTGTG TATGTGTGTC CCTGCGTGTG CGCATGTCTG TGCCATAGTA
11051 TCTGCAGGTT CTGTAATACA ATTTACTATA CAAGGTCATC AGCAGGCTGA
11101 GTATATGTCA GAATTTCTAG CTGAACTGAG TGCTATATGA CAACAAGGAT
11151 TTTTCTTGTT TTCCCAAGTG TTTTTTGTTC CATTTAGTCA GGTAGGTCAA
11201 TGAATTCACA TTGCCCAAAT GAAAGACACT TCAAGTTACC CATAATCACT
```

FIG. 3-5

```
11251 GATGTGTCCA ATTTTGACAT TAGAAAAACC TGATTAATAT ATTCCTTCCA
11301 ATATGGAAAC TTGCCCTAAT AACTAAAGCT AAGATTCCAA AGCCTAAATG
11351 TATTACAGCT CAAGTATTAA TTCAAATATT TATTGGTTAT TTTTCAGGAG
11401 TTGAAAAAGT CATTTGGTTG CCAATTGTGG ATTTGGGATT TTATCTATTA
11451 AAGGGTTTTT TTTTTTTTTC TCTTTGCTTT TGTTTCTCTA CAAAGGTCAT
11501 TGCCACAATG AACACAGCAT TTAATCAAAT TCCAGATTGG CCTTTGAACT
11551 TGGGATGATG GATAAAATGG ATTTGGGCCA AAATTGAAGT CAAGGAGACC
11601 AGTTAGAATA TCAAAATAAT TCATATATAA GAAAATGAGA CGTTGGTTTG
11651 GGGTAGAGTG GTAGGAATGA AAAAAATTAT TTGTGAGCTA ACACAAGGAA
11701 TAATTTCCAT AGGGCCTAAT AATAGTTAGG TCTGATAATA CTATGGTCTG
11751 ATAATAGTTT TATTGTATTG TTTACTGAGA GCACAAATGA TGTAACTTCC
11801 TTATTCAAGA GCTTTTCTAG TTTATTTAAA AATGTGTTGA CATCAGTTAG
11851 GTTTTAATGT TTTCTATATT TGGACAGTGT GAGCAAACTA ATTTGTTAAA
11901 TTAAATTCAG AGAGAGATAC ATCTATCTGT AAATACATAT ATGCGTTGTT
11951 TGTGTTGCTC TTCCTACATA GGTCAGCTAT AAGGCAAATA ATGTTCCTGG
12001 GTTATCTCAG TTTCACATTT CCCACTGTCA ATATTCCTGC TACTTTTAAG
12051 TCCCATATCC TGCTCTTTTC TTCCGTCAGT TTCCCCCAGA AGCTCCAAGA
12101 CCCCACCAGG AATCCCCATC CAAGTTTACT TTCCCAACTC CTGGAAGTTT
12151 CAATTGTGCT GCCTTTGTGA CATTATCATA TCTTTTCTGT TCAATGGTTG
12201 CTTCTCTTTG GCTCACTGTT CTCTACTTTT CAGCCTGAGA GCTGGCTAAT
12251 CTGGGACAGT ACTCGAATGC AGTGTACACA TGGGTAACAT GGAAAACCCC
12301 GATTTTCCCT TATATTCAAG GTATTATTTG ACCTTAAGAA AAACTGTTTT
12351 ACATTTCATA CCAATTAATG AGAAAAAAAT ATTGGCAAGC ACTGACTGGG
12401 CAGAATACAG GGAAGCTTCA CTATGGAGAA GTGAATTTGG GATTGAGGGC
12451 CTTTATTGCA ATCTCCTTGT AAATAATATT TGATACTCTT CCTCATCTGG
12501 AGACACATTC CTAAGTAACT TTTCCTGAAT AATTTGGTCT CCTTGACTGA
12551 ATCAGTAAGT ACAAATAGAT CCCCAAGCAT GGCTCTTTCC TAGAATGAAA
12601 GAAATGTCAA GAAGTCTGAA GATGATTCTT GAATTTTGGT TTTTTGCTAT
12651 TGCTATTTGG GCTTGTTGTC CTTGTTGTTG CTATTGAGTT GAGCTCCTTA
12701 TATATTCTGG TTACTAATCC CTTGTAATAT GGATAGTCTG CAAATATTTT
12751 ATCTCATTCA AAGATAATTA TTATTTACTT TCATAGGCTG TTTTTGGTAC
12801 CAAAGGTTTC TTTTTAGAAG ATAAGAAAAC GAAGATAGCT TCTACCAAAA
12851 TCTGCAACAA TAAGATACTC TGGTTGATAT GTAGCGAATT TATGTCCTTA
12901 TGGGCTGGAT CCAACAAGAA AAATATGAAT CAGGTATGTA TGATAATTAT
12951 AGGGCCATTT GATACCTTAA GAAATTCCAG CTTTCCTTTG ACTCATTTTG
13001 ATATATCTAT TTACTGTATA AATTCATATG GTATTCCAAA CCCTTAAAGA
13051 CAGATTTTTT TTTGCTTTTA AAAATGTTTA TGGGTATATA ATAGTTGTAC
13101 ATATTTATGA GACACATATA TTTTGATATA AGCATACAAT GTGTAATGAC
13151 CAAATCAGGG TAATTGGGAT ATCCATCACC TCAAGCATTT ATCATTTCTT
13201 TTTGTTAGAG ACATTCTAAT TTGACTCTTC TAGTTATTTT GAAATATACA
13251 ATGAATTATT GTTAACTATA GTCATCCTAT TGTGCATGCC AGACTTTAGT
13301 CCTTCTAACG GTATTTTGGT ACCCATTAAC CAATGCCTCT TTATCCTTCC
13351 CCCACCCCTA CTACCTTTCC CAGCCTCTGG TAACCATCAT TCTTCTCACT
13401 ATCTCTATAA GGTCAGTTTT TTTTTAAACT CCCCTATATG AGTGAGAACA
13451 TGCAGTATTT GTCTTTTTGT GCCTGGCTTA TTTCACTTAA TGTAATGTTC
```

FIG. 3-6

```
13501 TCTAATTTCA TCCACATTAT TGCAAATGAC ATGATTTCAT TCTTCTTATG
13551 GCTGTCTATA TGTACCACAT TTTATTTATC CACTCATCTG TTGATGGACA
13601 CTTAGGCTGA TTTCATATCT TGGTCATTGT GAATAGTGCT GTACTAAACA
13651 TGGGGGTGCA GATGTCTCTT CCATGGATTG ATTTCCTTTT TTTTTTCTGA
13701 ATATAGACCT AGCACTGGAA TTGCTGGATC ATATGGTAAT TCTACTTTTA
13751 GTTTTTTGAG GATCCCTCAT ACTCTTCCCC ATAGTTCCTG TACTAATTTA
13801 CATTCCTACC AACAGTCTGT GCAAGAGTTC TCTTTTCTCC ACATTCTTGT
13851 CAGCATCCAT TATTGCCTAT CTTTTTGATA AAAGCTATTT TAACTGGAGT
13901 GAGATAGTAC TTCATTGTAG TTTTAGTTCG CATTTCTCTA ATGATTAGTA
13951 ATGTTGAACA TTGTTTTTAA TGTACCTCTT GGCTATTTGT ATGTCTTCTT
14001 TTGAGAAATG TCTACTCAGA TCTTTTGTCC ATTTTTAAAT CAGATTTTTT
14051 TTTTGCAATT GAGTTATATG ACCTCTTTAT ATATTCTGGT TACTAATCCC
14101 TTGTCAGATG GGTAGTTTAC AAATATTTTC TCTCATTCAA CAGGTTCTTT
14151 AGTTCACTTT GTTGATGGTC TCCTTTGCTT TGCAGAAGCT TTTTAGCTTG
14201 ACGTAATCTA ATTTGTTCAT GTTTGCTTTG GTTGCCTGTG CATTTGAGGG
14251 CTTACCTCAA ATTGGCCCAG ACCAATGTCC CGGAGTGCTT CTGTAATGTT
14301 TGTTTTTTAG TAGTTTCATA GTTTTAGGTC TTAAATGTGT CTTTAATCCA
14351 TTTTGATTTT GTTTTTGTAT CTGGCAAGAG ATAGAGATCT AATTTCATTC
14401 TTCTGCATAT GGATATCTAG TTTTCCCAGC ATCATTTCTT GTGGAAATTG
14451 TCCTTTGCCC AATGTATGTT CTTGATGCCT TTGTTGAAAA TTAGTTGACT
14501 ATAAATGTGT GGATTTATTT GTGGGTTCTT TATTCTGTTC CATTGGTCTA
14551 TGTGTCTGTT TTTATGCCAG TATCATGCAG TTTTGATTAT TACAGGTTTG
14601 TAGTATAATT TGAAGTCAGG TCATGTGATG CCTCCAGCTT TGTTCTTTTT
14651 TCTCAGAATC TTATATTTAG AAAAACGTAA AGACTCCAAC AAAAAACCTG
14701 CTAGAACTGA TAAACAAATT CATTAAATTT GCAGGATACA ACATCAACAT
14751 ACAAAATTCA GCAGCATTTC AATATGCCAA GAGCAAATAA TCTTAAAAAA
14801 AAGAAAGAAA AAAAAACAAG AAATAATCCC ATTTATAATA GCTACAAATA
14851 AAATAAAACA CCTAGGAATA AACCATACCA AAGAAGTGAA AGATTTCTAC
14901 AATGAAAACT ATAAAACACT GATGAAAGAA ATTGAAAATG ACATTAAAAA
14951 ATGGAAAGGT ATTCCATGTT CATGGATTGC AAGAATCAAT ATTGTTAAAA
15001 TGTCCATATG ATCCAAAACA ATCTACAGAT TCAATGCAAT CCCTATCAAA
15051 ATACCAATGA CATTCTTCAT TGAAATAAAA AAAAAGCCTA AAATTTAAGT
15101 GGAACCATGA AGGTAGATGT CTGCTATACA TAGAAGATTA AGTACTCAAC
15151 AAACCTTGAA TATGAAGACT GGGGAAGTGA ATAGGCAGCT TCACTCTTCT
15201 ATTCCCTGGT GAAATTTAGG AGAATGGATG TTTTATAATG GGTAGCAGTT
15251 TCTTACATGT TCTCAATCAG CCATAACTTA CTACAGTCAA TTTGAATTTA
15301 TTGCATTTGA ATATATTGGA TTAAAAATAA AATCCTAAAA AAGGAGAGAA
15351 GCACATATAA ACCTGCGTCT TATTTCATGT GTTCCTTTCT TTGTGGGTGA
15401 CTTTTGTTTT GAAATAAAAC CTGCAAAATA ACAGGACAGG GTGGAAGGGA
15451 GATGGGATCC CCTCTTTATG AAGAAGCAGC AGTCCTGTTT TATCACCTCT
15501 TCATTTTCTG TTATTGAGAA TTCAAGAAGA AGGAGGAGGA AGAGTTCACA
15551 TCCACAGACT GGTGTGGTTG AATAGTTGTC TCTACTGTAT TCCAAATAGC
15601 AGCCAATGAG GCTGTTACAG TGAAGCCAGT CCCAAGATAA TTGTTCTGTA
15651 CCCCTATTCT CTAAGAAGCT AAATTGTGTT AGACTGAAAC CCATAAGGAA
15701 CCATTGTTCA AAGTTGGCTT GTTCAAAAGT AAAGATTTTT AATAGTTTCT
```

FIG. 3-7

```
15751 CTTAATTAGA TTATTTTCTA AGACATAGAA TTATGATTAC TATTTTATCT
15801 CTATAATTTT CATCTCTATA ACGTTTACAA ATACTGAAAT AACCTTTGGA
15851 AAAAATTGGC TTTTAGCTTT ACTTTTGCAA TATTTTATTT TATCCCCATA
15901 AAAGCCTAGG AAATTGGTAC TATGACTTTT AGTATGTTCA TTTAATAGAT
15951 GAAAACACAG AAACTCAAAG ATGTTAAATA TGGTGGCCAA GTTCACAAAG
16001 CTGATCATTA ACAACAACAG GCCTGAACT CCTGGTTTTC TGATTTAATC
16051 TGTGACAGTG CACCTGGGTG CGCATGCATG CATCACCCCC ACACTTGCAC
16101 ATAGAACCTT TCCTAGTTGG CTTTGCTCCA TGATGACCAT TACTGTTCCT
16151 TCTACTTCAA AATAAGCAAA TTATCCTACA GATTCAGAGC TGGTACAGGT
16201 GTGCTGTCAA GCAGCCCATT CCATTAGTCA GCTTGTGGTT CACTCACATT
16251 AAAGTATTGA CCTAAATGGT ATATTTATCT AGATAATTCT ACCTTGTTAT
16301 TTTCAAAGCC CCAGTCTTGT TTGCTAATTC TGTGCATCAT TTTTCTCTGA
16351 TTCTGAAAGG CAAAATTTTG TTGGGCAATT GCTGTAATAT GAGTTTTATC
16401 TCCTTTAGAG TCGAATGGAT GTGTATATGT CACATGCTCC CACTGGTTCA
16451 TCAGTACACA ACATTCTGCA TATAAAACAG GTAGAGTCTT AGTCATGGAA
16501 AACCATTCCA ATCCTTATTT TCAATATATT TAAAAAGACA GAATTGACCC
16551 TGTTAACAGG CCTACCCTAA GAATCTTAAG AGCTTGCTTC CAGTTTGTCC
16601 TTGCTGCCTT CTGTATGCCT TGATTTCCCT GGAATTTAAG AGAAAGGATG
16651 TTATGGTACA GACCAAGTAG ATGACATAAA TGAACACCAC CTTAAATCAG
16701 AGTTTTAAAA ATAGGCCCTG AACTGAAGCA AGAGGTAAAC TAGGGAAGCC
16751 TCAGGAGAAC TGAGACTTCT CCAGAGAGAA GTATCTGGGA TTTAACTTCT
16801 TTCTAATGAG GCTTGGTTTT CCATGAACTT TTCCTTTAAA CCAAGGGGGG
16851 TATTGCTCAT CTTTCTGTTG AGCCCCATTT GTCATAATTG TAAAATGGGT
16901 GGTTACATCC TTCTGGTGAT CTAGGAGCCC TATTTTCGTC CTAGCATACA
16951 GCATTTTTCT AAAATTTGCT GTTAGCTTTC ATGATTCTTA CCCTAACTAT
17001 TCTTTTTCTA AAAAACATTT GTTTCAGCTT TACCACTCTG ATGAATTCAG
17051 AGCTTATGAC TGGGGAAATG ACGCTGATAA TATGAAACAT TACAATCAGG
17101 TGAGCTATTT ACAGTAACCC CAGCATGCTG ATTTGATAA ATTATAATAA
17151 AAAATTATTT GAGGGTGGAA AGACTCCTAC CTGTCATTTG GTGGCATTTA
17201 TACTGATAGA ACTTTTTTTT AAAAAAATTT TAATTTTAAT TTTAATTTAT
17251 TTCAGAAAAT TTATAAATTA AAGAAGCATA TACAAAGAAA CTTACATCAT
17301 GTGTAATCCT TCCATCCAGA GATAACTAGA TGTACTAACA TTTTGGTGTA
17351 TTTATTCCAA TTTTCTCAGT ATTATATTGC TTTTAGACAA CTTTTAATCT
17401 TTCTATTTTA CTTAAGCTAT AGTAAGAGAT AACTAATATA ACTGAGGGAT
17451 TTTTAAATGC ATTTTTAATG GCTACATAAT AGAAATTATT TCATAAAAAT
17501 CTTTACAGCA TAAATGAATA TACACTTTTT AATACCAACA GAAAAATTAG
17551 AATTCCATAT GAAAGTTGAA TAAGTATTAC CCAACATTGA AGACTTGGGT
17601 CGTAAGGCAT CTTTCTCCAT ATAGCTTTAT GACATAAAAA TCTGTAGCCT
17651 TGTTTAGCAC CGTACTTTTA ATTAATCCTG TCACCATTTT TCTGTTCTCA
17701 TAGCCAGGGG CTTGGCTTAT AAGTATGAAC TAAGCAAACT AAATTAAATT
17751 GTTTTAAGTA TTTTCCCAGG CTATCATATT TTAAGCTATT TACTGGTGCA
17801 ACTATAGATT ATTAATAAGT TGTTTCTGAG GATCAAAACA ATCAGACTAA
17851 TCAATTTCTC AATAATGAAT TGGCCTGTTA GAGGAATAAT TCTACTAATC
17901 CTTAAAACCA CTACAAGAGA TAGACCATGT ATATTTTATT TATTTTTAAA
17951 AATAAGTTTA AGATGTGATT TACATACAAG AACATTACTA ATTTTGTGTG
```

FIG. 3-8

```
18001 TCCCATTTAA TAAGTTTTGA CAAATATATT TATTTGTGTA ACCACACCAC
18051 AATCTAAATA TAGGACGTTT ATATCACCAC TAAAAGTTTT TTTCCTGCTC
18101 CTGAGACTAT TTATAGACAC AAATGCGTGT ATTTGCAAAT GCTTAGAAAA
18151 GGTCTAGAAA AAAAAACAGT AAATGTTAAA GTGGTTATCT TCAGAGAGAA
18201 GAAAGAAGAA AAGAAGTGGA TGGACATGAA ACAGTAAAGG ACCCTCATTT
18251 TGGACTTTAC ATATGTCTGT TTTCTTCCAT TATTTTGAAT AAACATGCTA
18301 TATTTATAAA TTATTTACAT TTACAAGAAA ATGAAACAAA ATCAACACGC
18351 ACATTCAAGA TCATTATGGT CAAGTACTAA AGTATGTGAG AGTGTTAATG
18401 TCCTTAGAAT TTGGCCACAG TTAGCTGGTC CTACTCTGCT CCAAGCCGGT
18451 CCTATTTTGT GAATTAATCT CATTTGATGC CAATTTTTAT TACATTCTCT
18501 CCAAAAAACT AGTCTCAACA GTTTGCTCTC TCCTCAAGTT CACAGCATTA
18551 TCTCTGCTAT ATCTATATTT TATTGAGTAT AAGAGAATTA ACCCATGTAA
18601 GCTCCATGAG GGTAGGGATT TCTCATCGTT TTGTTCACCA GTGTTTTCTC
18651 ATCTTGAAGA GTACATGACA ATTACTGGGC TCCCAGTATC TATGTGTTGC
18701 ATTAATGAAA TTTCTTAACT TTAATCTACC TCAAAATGTC TCTATCTTCT
18751 TGATTCTCTC CTTCCTTTCT CTATCAGAAA ATGATGGTCC TCTTATTTTC
18801 CAAGTTATTC CGGTCCTGTG CCCTTGATCC CATCTCTTCT CACTTCCCCT
18851 TCCTTCCTGC CTCCATTCTC CTGTCCCTTA TGAAAAACAA GCAAGACCAT
18901 CAATTCTATC AAGTTATCAT TATGTCACTC TGTTCTTATC AACATATTTT
18951 TAGTATTGAA GAGGGCTTCT TCTACTTACT CCTGAACCTT GTACAATGTA
19001 GTTTAGGTCT TCATCTTTTT ATCATAGCTA CCTTATTTAA AGTCACCCAT
19051 GGCTTTTAAT TGCCAAATTC AATGGCCTAT CTTCACCTTT TGAAATGTGT
19101 TATGTTCGTT ACCACAGTCT CCTTGAAACT CAGTCCCCTG ACTTGGACTT
19151 CCATAACACA ATGATTTCTG ATTTTCCTTC TGTTTGTGAT TGTTCCTTTT
19201 GTCCCAGGCA CTGGCTACTC CACCTTCCAC CTCTCTGAAA TCATTAGCAT
19251 TCCCCAAGGA TTCTTCAAAA CTCTCTTTCT TCCTTGGAGA AGTCAGCATA
19301 GCTTTAATTT GGACCATTTC TATGGCTTAT CTAGATTTTT TCAGGACTTG
19351 CCTTCAACCT ATTCTTTCTG TAGGTGATTC CATTAACTGT TGCCCATATG
19401 GTAGTCCGAA GACAGACCTC CGAGAAATGA CCCTTGTCTC CAAAACTTCC
19451 GCAATATGTC CAAATTTCCT AGCCTGACAT TCAGACTTTG ATTATCTGCC
19501 TCCAAGTTTA TATCCTATCA TATTCCTTTA TATATTCTGT TCTCCAGGTA
19551 CACTGGGAAG CTTGCCATTC CTGATCATAG CCTACAAACT CTTCCTGCCT
19601 CCCACTCACC CTCATCTCTG CTGTCAAAAT GCAACCTTCC CTCAAGAGTC
19651 ATTTCACAGG ACCCCTCTTT CTATGAAGCC CTCAGGTGGA AATAATTTTT
19701 TGCCTTTTTT TCCATTTTAT TTTTGGAGTG TTTATGGCAT TTAACATACC
19751 TTACTTTGTA TACAAATATT TGCCTTGCTC CCTCTTTTGC AAATTTCTTA
19801 AAGGTAGAGA CCATTGTATG TTTTCTTCAT ATGTTGCTGG TGCCTAACAG
19851 AACTATGGCC ATTGTCCACA TTCATTTAGC AGCCTTTGTA GTTATTGCTT
19901 TGAGGAGCTT CCTCTCATGA ATGCCCTTGC TTTCTCTCCC ACAGAGTCAT
19951 CCCCCTATAT ATGACCTGAC TGCCATGAAA GTGCCTACTG CTATTTGGGC
20001 TGGTGGACAT GATGTCCTCG TAACACCCCA GGATGTGGCC AGGATACTCC
20051 CTCAAATCAA GAGTCTTCAT TACTTTAAGC TATTGCCAGA TTGGAACCAC
20101 TTTGATTTTG TCTGGGGCCT CGATGCCCCT CAACGGATGT ACAGTGAAAT
20151 CATAGCTTTA ATGAAGGCAT ATTCCTAAAT GCAATGCATT TACTTTTCAA
20201 TTAAAAGTTG CTTCCAAGCC CATAAGGGAC TTTAGAAAAA ATGGTAACCA
```

FIG. 3-9

```
20251 ACAATGAGGT TGTCCCCCAG CACCCTGGGG GAGATGCACA GTGGAGTCTG
20301 TTTTCCAAGT CAATTGTGTT AGTGTTATTT ATGTTTAGAG ACATCTTTGC
20351 ATGGGACCAT CTACAGGTCC TTATAAACAA TGAGGTAGAT TAGGCAAAAA
20401 GATAAACAAG TTGCTACTCT ATCTGGCATT TAAGTCTAAT TAAATTGTAA
20451 TTTTTAGGGC ATACCATGAA GTATAGAAAT GTCTGAAGCT TCAAAGGAAC
20501 AGTGAAATTC CTTTAAGGTC CTATATGGAA ACCTCTGTTG TCATTTTATT
20551 TATATGGATT GCTATGGCAA TGGACAGAGT GTGGGATTAG GAGGAGGGCC
20601 TGTAACTTCT TTATAAAAGT TTCTTAGCTA TCCTGAAGAT GTATAGACAT
20651 TTTTACTTTT TTAGGTATTT TCAACATCAG AAATTCAAAA AAGTCCCCAA
20701 AGATTCTTCC AGAGAAGCCC TCTTTTCTTA CAATCTTATC CCTGGCTATC
20751 TGCGTAAACG GAATCTTGAA CCCATAATAG GATACATGTA TAAAATCTTC
20801 CTTATTAAAG CAGAAATAAA TTGTACAGCA TCAATATCAT TTTATAATCA
20851 TAGGGAGGCT TCTTTGTTTA GCATGTAATG CCCCCTTTAC AGGCTTTTTG
20901 TTCTTTGAGG GGTTTGAACA TTCCATGAAA AACTGACAGA TAGGAAACTG
20951 ACAATAAAAG ATTGAGCTAA AGATGGAAGC AGAAAGTACT AGGCTAGATA
21001 GTCTCTAAAC ATTAAGTATT TTCTTCCTCC ATCTTAAAAG CAATGAGAAG
21051 CCACCAAAAT ATTTTACCTA ATGGAAACCT GATTGCCGCA TTTTTGTAAC
21101 CACCACTTTG GCTGCTACAT AGAGAATGGA TTAGAAGATG CCAACAAAAG
21151 ATTCTGAGCA AGTCTGTAAA TCTGATCAAG TGTTCTGATG CAGGCTGATA
21201 TCCTTCTGTG CTAAGAGAGA TGATCCTTGG AAAATCCAGA GCCAGCTCCA
21251 TAATACTTTC CTGCTCTGCT GGCAAATCCA CAAGCTGCTG GCCCCTGGAG
21301 CCATTCTTCT CTCAAAACTA GCATTCATCA ATTTAATGTA TACGTATTGA
21351 TGGGGAATAA TGGTCACTAT GAAAACCATG TGATAATATG GAAAAATACC
21401 CATGATATAA TGTTATGTGA AGAGAAGAAA ATGAAACTGG TAGAACTATG
21451 TGATTGCAAA TATATACAAA TATTAAAACA ATTATATGAC TTTATAAAAT
21501 ATTTGTATAT AATGAAAACT GAAGCAATAT AAAAAATAAA ATTAGTTGTG
21551 TCAGGGTAGT AACATGATGA GTGATTAATA GTTTTTAATT TTTAATATAG
21601 TAATGACATA ATGTTACAAC TTGTCCAAAT CTCACAAACA TAATATTCAG
21651 TAAAGGAAGA TAAACATAAA AGAATACATA TTTTATTATA CATTTTTATG
21701 TAGGCTAATT GATGGTTCTG AAAGCCTTAA AAAGCTTACT TTTAGGAGGA
21751 GAATCATGCC TTGGAGGACT CTAGGGTCCA GAAAAATGTC CTAATACTAG
21801 AGCTAGGTGC AGTCAGATTA ATTATAATAC ATTTCATTAT TTTGTCTGGA
21851 ATACCAAGAT GACTTCCAAG CAGGAATGGA GTCTAGCAAC ACTTTACTGA
21901 TGGGGAACTT GGCCACAGAC TTGTAATACA AATTTTTGGA TATGTTGACA
21951 ATGTTTCTCC TTATTTTTCT TACTTATACA AAGCAAGAAA TTTGGCTCAC
22001 AACCTTGAAA CAGACTTACC AGGTTCCTCC AGTTTCCCAA GCCTCAATAT
22051 CTCATTGCTA TTTTTAA
     (SEQ ID NO: 3)
```

SNPs:

| DNA Position | Major | Minor |
|---|---|---|
| 165 | G | A |

FIG. 3-10

| | | |
|---|---|---|
| 226 | A | G |
| 231 | T | C |
| 359 | A | – |
| 544 | G | T |
| 598 | C | T |
| 1621 | A | G |
| 2330 | C | T |
| 2498 | A | G |
| 2791 | T | C |
| 2877 | T | C |
| 2879 | T | C |
| 2912 | A | G |
| 3076 | G | T |
| 3745 | C | G |
| 3752 | T | – |
| 3762 | – | C T |
| 3833 | A | G |
| 4399 | T | C |
| 4945 | A | G |
| 5056 | A | G |
| 5280 | T | A |
| 5790 | A | G |
| 5901 | C | T |
| 6457 | C | T |
| 6632 | T | A |
| 6763 | A | G |
| 6955 | – | T C |
| 7017 | T | G |
| 7151 | G | T |
| 7308 | C | G |
| 7321 | T | C |
| 7542 | C | T |
| 8597 | T | C |
| 8803 | C | T |
| 9016 | G | A |
| 9967 | T | C |
| 10008 | C | T |
| 10363 | G | A |
| 10684 | T | C |
| 11177 | G | T |
| 12345 | T | C |
| 12349 | C | T |
| 13115 | C | T |
| 13354 | T | A |
| 13373 | C | G |

FIG. 3-11

| | | |
|---|---|---|
| 14677 | C | G |
| 14734 | G | A |
| 14747 | A | G |
| 14808 | - | A |
| 15086 | - | A G |
| 15414 | A | G |
| 15722 | T | C |
| 15861 | T | C |
| 16264 | A | T |
| 16314 | G | A |
| 16877 | A | G |
| 16966 | T | G |
| 17147 | A | G |
| 17219 | T | C |
| 18628 | A | G |
| 18655 | T | G |
| 18984 | G | T |
| 19407 | C | T |
| 19531 | T | C |
| 19911 | C | T |
| 20199 | A | G |
| 20243 | G | A |
| 20640 | T | C |
| 21156 | G | C |
| 21163 | A | T |
| 21425 | G | A |

Context:
DNA
Position

165    TTATGGCCTAACCTTTTTAACTTTGAGTTATTTTCAAGAGAAAATTTGAAAAAGCAGCCT
TTGAGGAGAAAGAAGCAATCCAACAAACAAAAAGATAACCACACTGTAATAGGAAATGTG
TTTTGAATAGGACATTGGAAGAAAAATAATAATCATTTTTACAG
[G,A]
TAGATCCCAAAGTCAAGGATCTATGTTCAACCATGTGTGTTCCACCATCTTCACAATTGA
ATGAGTAACCATCATTAAGCAGTTAGCTTAGGCCGTAATATGATTCTTGGACTGAGATTT
CAAAAATACCACAGGCCTTCTGAAAGGTTACCCCTTTCTAGCTCCACTATCATCTAATTT
TATTAAAAAAAAAAAAAAAGGAAAAATTTGAGCTTCTAGAGAGTAGGGGCTACCATTTTG
TATCCCACAGGGCCAAGGAACAAGTTTTAATGTATTCATTTAAATTAATTTCAGTATGAG

226    TTATGGCCTAACCTTTTTAACTTTGAGTTATTTTCAAGAGAAAATTTGAAAAAGCAGCCT
TTGAGGAGAAAGAAGCAATCCAACAAACAAAAAGATAACCACACTGTAATAGGAAATGTG
TTTTGAATAGGACATTGGAAGAAAAATAATAATCATTTTTACAGGTAGATCCCAAAGTCA
AGGATCTATGTTCAACCATGTGTGTTCCACCATCTTCACAATTGA

FIG. 3-12

[A,G]
TGAGTAACCATCATTAAGCAGTTAGCTTAGGCCGTAATATGATTCTTGGACTGAGATTTC
AAAAATACCACAGGCCTTCTGAAAGGTTACCCCTTTCTAGCTCCACTATCATCTAATTTT
ATTAAAAAAAAAAAAAAAGGAAAAATTTGAGCTTCTAGAGAGTAGGGGCTACCATTTTGT
ATCCCACAGGGCCAAGGAACAAGTTTTAATGTATTCATTTAAATTAATTTCAGTATGAGT
ATTGAAATATATAATAGAAATATTGTAACATTATATATTTTCTATATACTTTTATTATAT

231  TTATGGCCTAACCTTTTTAACTTTGAGTTATTTTCAAGAGAAAATTTGAAAAAGCAGCCT
TTGAGGAGAAAGAAGCAATCCAACAAACAAAAAGATAACCACACTGTAATAGGAAATGTG
TTTTGAATAGGACATTGGAAGAAAAATAATAATCATTTTTACAGGTAGATCCCAAAGTCA
AGGATCTATGTTCAACCATGTGTGTTCCACCATCTTCACAATTGAATGAG
[T,C]
AACCATCATTAAGCAGTTAGCTTAGGCCGTAATATGATTCTTGGACTGAGATTTCAAAAA
TACCACAGGCCTTCTGAAAGGTTACCCCTTTCTAGCTCCACTATCATCTAATTTTATTAA
AAAAAAAAAAAAAGGAAAAATTTGAGCTTCTAGAGAGTAGGGGCTACCATTTTGTATCCC
ACAGGGCCAAGGAACAAGTTTTAATGTATTCATTTAAATTAATTTCAGTATGAGTATTGA
AATATATAATAGAAATATTGTAACATTATATATTTTCTATATACTTTTATTATATAGAAA

359  CTTTGAGGAGAAAGAAGCAATCCAACAAACAAAAAGATAACCACACTGTAATAGGAAATG
TGTTTTGAATAGGACATTGGAAGAAAAATAATAATCATTTTTACAGGTAGATCCCAAAGT
CAAGGATCTATGTTCAACCATGTGTGTTCCACCATCTTCACAATTGAATGAGTAACCATC
ATTAAGCAGTTAGCTTAGGCCGTAATATGATTCTTGGACTGAGATTTCAAAAATACCACA
GGCCTTCTGAAAGGTTACCCCTTTCTAGCTCCACTATCATCTAATTTTATTAAAAAAAAA
[A,-]
AAAAAGGAAAAATTTGAGCTTCTAGAGAGTAGGGGCTACCATTTTGTATCCCACAGGGCC
AAGGAACAAGTTTTAATGTATTCATTTAAATTAATTTCAGTATGAGTATTGAAATATATA
ATAGAAATATTGTAACATTATATATTTTCTATATACTTTTATTATATAGAAATATATAT
TACAGAATATATTATTAAATATTGTAGAACAATATATAATACAGAAAATATATAATACT
CAGTAATATATTAAATACTTATTAAAATAGCAAGCTTATATAGGAAGAGTGATGGAGCAT

544  GCAGTTAGCTTAGGCCGTAATATGATTCTTGGACTGAGATTTCAAAAATACCACAGGCCT
TCTGAAAGGTTACCCCTTTCTAGCTCCACTATCATCTAATTTTATTAAAAAAAAAAAAAA
AGGAAAAATTTGAGCTTCTAGAGAGTAGGGGCTACCATTTTGTATCCCACAGGGCCAAGG
AACAAGTTTTAATGTATTCATTTAAATTAATTTCAGTATGAGTATTGAAATATATAATAG
AAATATTGTAACATTATATATTTTCTATATACTTTTATTATATAGAAATATATATTACA
[G,T]
AATATATTATTAAATATTGTAGAACAATATATAATACAGAAAATATATAATACTCAGTA
ATATATTAAATACTTATTAAAATAGCAAGCTTATATAGGAAGAGTGATGGAGCATTGTGA
GAAAGTTTCAGCTTTATTTCTTTGACATTACTTTGTTTCTGCACAAACAAAAGAATTACA
GGAATTGTCCAGATTATTCAAATAACTCGAAGTTGAGGAGGGAATATAAGTCAATGATGT
AGAAACTCTTTTAAGATTTGAGCTAGCCTACAATCTGTAAAGATCTGTGAAATTGAACTA

598  AGGCCTTCTGAAAGGTTACCCCTTTCTAGCTCCACTATCATCTAATTTTATTAAAAAAAA
AAAAAAGGAAAAATTTGAGCTTCTAGAGAGTAGGGGCTACCATTTTGTATCCCACAGGG
CCAAGGAACAAGTTTTAATGTATTCATTTAAATTAATTTCAGTATGAGTATTGAAATATA

FIG. 3-13

TAATAGAAATATTGTAACATTATATATTTTCTATATACTTTTATTATATAGAAAATATAT
ATTACAGAATATATTATTAAATATTGTAGAACAATATATAATACAGAAAAATATATAATA
[C,T]
TCAGTAATATATTAAATACTTATTAAAATAGCAAGCTTATATAGGAAGAGTGATGGAGCA
TTGTGAGAAAGTTTCAGCTTTATTTCTTTGACATTACTTTGTTTCTGCACAAACAAAAGA
ATTACAGGAATTGTCCAGATTATTCAAATAACTCGAAGTTGAGGAGGGAATATAAGTCAA
TGATGTAGAAACTCTTTTAAGATTTGAGCTAGCCTACAATCTGTAAAGATCTGTGAAATT
GAACTATATTTGTGCTATTTCCATATTAAGTCAAGGCAACAAATCAATATTAATAATAAT

1621  CGGCTTAAGCTCCACAGGCATACAAAGTGAAGCAGAAAACTGAGGCACGTGTGCCTCCAT
TATCTGGTATCTCATGTGGGGCTTAGAGGTAAATTGTCGTTATTTGGCCTCCATTTCTGC
CTTTAACCACTGGTGTAAACAAAGGTTACTGTGCCAAAGTTGACAGCAACCCAAATCCCT
TTGGCATGTGAATTAGTTTCCTCTGCCATACTGCTAGTTCCAAATTCCTTCTGGTTTCAG
GATTTAGGAGTCAGGGTTGCCTCATCTTCTCAAATGAGTTACAGTCACGCACATCCCTAC
[A,G]
CACTGCATGGTTGGCACTAGTTCCTTGATATATGTTACTCCGTTTGATCCTCATGAAGGA
TCAAATGGGGAAGGGAGATACTATTGTCTCTGATTGTCCATTAAGATCTTGAGTATGTTC
TACTTCCCTGTTTGACACACTGGTTTGAAAATGTTGCTAAGTCTTCCCAACAATGACAGA
TACTCAGTGGAAACATGAAGGATTCCGTCAAACTGGTTATTTTGCATCATGTAGACCACT
ATTTCCCAACCTGCAAGTGCATCATGGCCTTTGGTGTGTCAGGGACACGCCTTGGGTGTG

2330  AAAAGTTCAGAAGTTCCTCATCAATAAGGAGTCCTTGTGAGCAGGTGAAGCTCATCTAAC
TAGGTAAGATGAAGATCTATCATAACCAGGAGGCAGGTTGGAAGGTGCCAGTTGCACTGG
CAGTCAGGTGCAAGAGCTCTGCAGTGAGGCTGCCTGAGTGTCCATCCTAGATCTCTCACC
TCTTGGCTCTGTGACCTTGAGCAGGTCTTAAATCTCTCTAAGCCTTTGTTTTTTTAATTG
ATAAAATGAGGATAATAATAGTACCAAAATTAGGGAGATTTTCAGAGCTTAAATAACATA
[C,T]
GTGAACTATTTAGAGTAATGCCTGCCATAAGGGGACTCAGTAGCTTATTATTAGTTTCAT
ACAATTTGAAAAGTTTCATAATATTTGCAGATATAAGATGATCTTCAACCAGATAGCTAA
TGTATGCAAAGCTATTTAGCTTCAGAAGTAAACTCTGCATTTCTAGAAGTTAAATATTAC
TTTGTTATAGTGAATTATCTGTAATATTTATCTCTTGCTCACTTTTATAAGAAAAATAGT
GAAAGCATTTATTAAGAACTTACACTGCACTAAATGTTATATATGACTTAATCCTCACTA

2498  AGATCTCTCACCTCTTGGCTCTGTGACCTTGAGCAGGTCTTAAATCTCTCTAAGCCTTTG
TTTTTTTAATTGATAAAATGAGGATAATAATAGTACCAAAATTAGGGAGATTTTCAGAGC
TTAAATAACATACGTGAACTATTTAGAGTAATGCCTGCCATAAGGGGACTCAGTAGCTTA
TTATTAGTTTCATACAATTTGAAAAGTTTCATAATATTTGCAGATATAAGATGATCTTCA
ACCAGATAGCTAATGTATGCAAAGCTATTTAGCTTCAGAAGTAAACTCTGCATTTCTAGA
[A,G]
GTTAAATATTACTTTGTTATAGTGAATTATCTGTAATATTTATCTCTTGCTCACTTTTAT
AAGAAAAATAGTGAAAGCATTTATTAAGAACTTACACTGCACTAAATGTTATATATGACT
TAATCCTCACTATAACCCTATGAGATAGGTTACATTATTGTCCTAATTTTACTAACAAGG
AAACCAAGAGACAAAGCTACTAAAACACTTGCCTGAGGTTAGACATCTTCTTCTGTGGTG
AGGCTGGATTTCAAATTTAGACCATTTGACTGTAGCACTTATATGATGAGCATGCTGTTT

FIG. 3-14

2791  TTCTAGAAGTTAAATATTACTTTGTTATAGTGAATTATCTGTAATATTTATCTCTTGCTC
ACTTTTATAAGAAAAATAGTGAAAGCATTTATTAAGAACTTACACTGCACTAAATGTTAT
ATATGACTTAATCCTCACTATAACCCTATGAGATAGGTTACATTATTGTCCTAATTTTAC
TAACAAGGAAACCAAGAGACAAAGCTACTAAAACACTTGCCTGAGGTTAGACATCTTCTT
CTGTGGTGAGGCTGGATTTCAAATTTAGACCATTTGACTGTAGCACTTATATGATGAGCA
[T,C]
GCTGTTTAGTGTTATAGTGTTGGTCTACCTTTGAATAGACATACTTTTAAACCATGGCAA
GGAAGTGAGACTGCACATTGAAATATGTAAAATTTGCCTTTGGGTGCCACGTGAGAAATA
GTCACATCACTAGAAACTAATCATAAGCTTTTGTGTTTGGTTAAAGTTTTATTGATCCAT
TTTTCTTGTTTACTTTGTGGGATACTGGGCTTAACTAGGGGATACCTCCACTTTTTACTT
GGCCATGGTATGAAAACCTGTCCTCTGAATCTTTAGATATTTTGGCAAATTGTAGGCAAA

2877  ATTTATTAAGAACTTACACTGCACTAAATGTTATATATGACTTAATCCTCACTATAACCC
TATGAGATAGGTTACATTATTGTCCTAATTTTACTAACAAGGAAACCAAGAGACAAAGCT
ACTAAAACACTTGCCTGAGGTTAGACATCTTCTTCTGTGGTGAGGCTGGATTTCAAATTT
AGACCATTTGACTGTAGCACTTATATGATGAGCATGCTGTTTAGTGTTATAGTGTTGGTC
TACCTTTGAATAGACATACTTTTAAACCATGGCAAGGAAGTGAGACTGCACATTGAAATA
[T,C]
GTAAAATTTGCCTTTGGGTGCCACGTGAGAAATAGTCACATCACTAGAAACTAATCATAA
GCTTTTGTGTTTGGTTAAAGTTTTATTGATCCATTTTTCTTGTTTACTTTGTGGGATACT
GGGCTTAACTAGGGGATACCTCCACTTTTTACTTGGCCATGGTATGAAAACCTGTCCTCT
GAATCTTTAGATATTTTGGCAAATTGTAGGCAAACAAAGACTTAAAGCAATTCAACCTTG
ATTAAAATAAGACCAAAAATGCCTCCATACTTGATTAAATTTATTTCATTTTAGGAACTG

2879  TTATTAAGAACTTACACTGCACTAAATGTTATATATGACTTAATCCTCACTATAACCCTA
TGAGATAGGTTACATTATTGTCCTAATTTTACTAACAAGGAAACCAAGAGACAAAGCTAC
TAAAACACTTGCCTGAGGTTAGACATCTTCTTCTGTGGTGAGGCTGGATTTCAAATTTAG
ACCATTTGACTGTAGCACTTATATGATGAGCATGCTGTTTAGTGTTATAGTGTTGGTCTA
CCTTTGAATAGACATACTTTTAAACCATGGCAAGGAAGTGAGACTGCACATTGAAATATG
[T,C]
AAAATTTGCCTTTGGGTGCCACGTGAGAAATAGTCACATCACTAGAAACTAATCATAAGC
TTTTGTGTTTGGTTAAAGTTTTATTGATCCATTTTTCTTGTTTACTTTGTGGGATACTGG
GCTTAACTAGGGGATACCTCCACTTTTTACTTGGCCATGGTATGAAAACCTGTCCTCTGA
ATCTTTAGATATTTTGGCAAATTGTAGGCAAACAAAGACTTAAAGCAATTCAACCTTGAT
TAAAATAAGACCAAAAATGCCTCCATACTTGATTAAATTTATTTCATTTTAGGAACTGGA

2912  TATGACTTAATCCTCACTATAACCCTATGAGATAGGTTACATTATTGTCCTAATTTTACT
AACAAGGAAACCAAGAGACAAAGCTACTAAAACACTTGCCTGAGGTTAGACATCTTCTTC
TGTGGTGAGGCTGGATTTCAAATTTAGACCATTTGACTGTAGCACTTATATGATGAGCAT
GCTGTTTAGTGTTATAGTGTTGGTCTACCTTTGAATAGACATACTTTTAAACCATGGCAA
GGAAGTGAGACTGCACATTGAAATATGTAAAATTTGCCTTTGGGTGCCACGTGAGAAATA
[A,G]
TCACATCACTAGAAACTAATCATAAGCTTTTGTGTTTGGTTAAAGTTTTATTGATCCATT
TTTCTTGTTTACTTTGTGGGATACTGGGCTTAACTAGGGGATACCTCCACTTTTTACTTG
GCCATGGTATGAAAACCTGTCCTCTGAATCTTTAGATATTTTGGCAAATTGTAGGCAAAC

FIG. 3-15

```
          AAAGACTTAAAGCAATTCAACCTTGATTAAAATAAGACCAAAAATGCCTCCATACTTGAT
          TAAATTTATTTCATTTTAGGAACTGGATTATAATCAAGACAACTTCTACATGAAAAAATA

3076  CTTATATGATGAGCATGCTGTTTAGTGTTATAGTGTTGGTCTACCTTTGAATAGACATAC
          TTTTAAACCATGGCAAGGAAGTGAGACTGCACATTGAAATATGTAAAATTTGCCTTTGGG
          TGCCACGTGAGAAATAGTCACATCACTAGAAACTAATCATAAGCTTTTGTGTTTGGTTAA
          AGTTTTATTGATCCATTTTTCTTGTTTACTTTGTGGGATACTGGGCTTAACTAGGGGATA
          CCTCCACTTTTTACTTGGCCATGGTATGAAAACCTGTCCTCTGAATCTTTAGATATTTTG
          [G,T]
          CAAATTGTAGGCAAACAAAGACTTAAAGCAATTCAACCTTGATTAAAATAAGACCAAAAA
          TGCCTCCATACTTGATTAAATTTATTTCATTTTAGGAACTGGATTATAATCAAGACAACT
          TCTACATGAAAAAATAGATTAATAGTGCTCCAAGTTAGTTCACTGTATTTATTCCTTTTT
          ATACATTATCTGCCTTCGGTGTTATTCAAGTTTTCATTAATCATTAATAATTTCACTAAT
          CATTTTATTTCATTAATCAACATTGATAGTTAAAATTAATCTGTGAATATTAAATGTTTT

3745  TGGTGGATTCCTTGATTTGGAAAATGAAGTGAATCCTGAGGTGTGGATGAATACTGTAAG
          TCATGGAAAACTGTGAAGAACATCAAATAAAGCAGGACTAATGGAGTATGAGGTTACGAA
          AGGTCCTGTTGTAACAGAAAATCTCTGATAAAACAGATAAAATGTAGATGGTTTTTAACC
          TCTGCAAGAGTCAAGCTAGTTAGATCTTTGTCTGAAAAACAAATACTGTCCGGTAATGAA
          AACCAAATTGTGCTATTGTGCTATCTATCTATCTATCTATCTATCTATCTATCTATCTAT
          [C,G]
          TATCTATCTATCTATTTATCTATCTATCTATAGATAGAACCTCCTCTTTTGAATTTATGT
          TTTAAGAATATCAAGCTATTTGTTGATATACATGATTGCCTTCTATTGATCTATAGTTCT
          ATTACTTTTAAAGCAAGAGGGGTCTCAAAAGACAATTGACTTGATAATATAGCTTTGTCA
          GAAAGAATGGGTCAATGCTAAATTTTCCCCCAACCCCCCAAAATATTAGCCAATAGTAGA
          TATTTTTTAAAATTCTACTTATTTTGTATTAAGACTTTATTTATTAATTTTACAGTTACC

3752  TTCCTTGATTTGGAAAATGAAGTGAATCCTGAGGTGTGGATGAATACTGTAAGTCATGGA
          AAACTGTGAAGAACATCAAATAAAGCAGGACTAATGGAGTATGAGGTTACGAAAGGTCCT
          GTTGTAACAGAAAATCTCTGATAAAACAGATAAAATGTAGATGGTTTTTAACCTCTGCAA
          GAGTCAAGCTAGTTAGATCTTTGTCTGAAAAACAAATACTGTCCGGTAATGAAAACCAAA
          TTGTGCTATTGTGCTATCTATCTATCTATCTATCTATCTATCTATCTATCTATCTATCTA
          [T,-]
          CTATCTATTTATCTATCTATCTATAGATAGAACCTCCTCTTTTGAATTTATGTTTTAAGA
          ATATCAAGCTATTTGTTGATATACATGATTGCCTTCTATTGATCTATAGTTCTATTACTT
          TTAAAGCAAGAGGGGTCTCAAAAGACAATTGACTTGATAATATAGCTTTGTCAGAAAGAA
          TGGGTCAATGCTAAATTTTCCCCCAACCCCCCAAAATATTAGCCAATAGTAGATATTTTT
          TAAAATTCTACTTATTTTGTATTAAGACTTTATTTATTAATTTTACAGTTACCTGGTGCT

3762  TGGAAAATGAAGTGAATCCTGAGGTGTGGATGAATACTGTAAGTCATGGAAAACTGTGAA
          GAACATCAAATAAAGCAGGACTAATGGAGTATGAGGTTACGAAAGGTCCTGTTGTAACAG
          AAAATCTCTGATAAAACAGATAAAATGTAGATGGTTTTTAACCTCTGCAAGAGTCAAGCT
          AGTTAGATCTTTGTCTGAAAAACAAATACTGTCCGGTAATGAAAACCAAATTGTGCTATT
          GTGCTATCTATCTATCTATCTATCTATCTATCTATCTATCTATCTATCTATCTATCTATT
          [-,C,T]
```

FIG. 3-16

```
     ATCTATCTATCTATAGATAGAACCTCCTCTTTTGAATTTATGTTTTAAGAATATCAAGCT
     ATTTGTTGATATACATGATTGCCTTCTATTGATCTATAGTTCTATTACTTTTAAAGCAAG
     AGGGGTCTCAAAAGACAATTGACTTGATAATATAGCTTTGTCAGAAAGAATGGGTCAATG
     CTAAATTTTCCCCCAACCCCCCAAAATATTAGCCAATAGTAGATATTTTTTAAAATTCTA
     CTTATTTTGTATTAAGACTTTATTTATTAATTTTACAGTTACCTGGTGCTACAAATTTCA
```

3833 
```
     AAAGCAGGACTAATGGAGTATGAGGTTACGAAAGGTCCTGTTGTAACAGAAAATCTCTGA
     TAAAACAGATAAAATGTAGATGGTTTTTAACCTCTGCAAGAGTCAAGCTAGTTAGATCTT
     TGTCTGAAAAACAAATACTGTCCGGTAATGAAAACCAAATTGTGCTATTGTGCTATCTAT
     CTATCTATCTATCTATCTATCTATCTATCTATCTATCTATCTATCTATTTATCTATCTAT
     CTATAGATAGAACCTCCTCTTTTGAATTTATGTTTTAAGAATATCAAGCTATTTGTTGAT
     [A,G]
     TACATGATTGCCTTCTATTGATCTATAGTTCTATTACTTTTAAAGCAAGAGGGGTCTCAA
     AAGACAATTGACTTGATAATATAGCTTTGTCAGAAAGAATGGGTCAATGCTAAATTTTCC
     CCCAACCCCCCAAAATATTAGCCAATAGTAGATATTTTTTAAAATTCTACTTATTTTGTA
     TTAAGACTTTATTTATTAATTTTACAGTTACCTGGTGCTACAAATTTCAGATAATTCACC
     CTAATAAGCACACAACAGATGGTTTGTTTTGATTCCTTTTTATATCCTTTGGAGAAGTTC
```

4399
```
     GTTTTGATTCCTTTTTATATCCTTTGGAGAAGTTCCACTAACGACTGTATTTTTACTGGG
     CAGAGTGAAATCATCATCTACAATGGCTACCCCAGTGAAGAGTATGAAGTCACCACTGAA
     GATGGGTATATACTCCTTGTCAACAGAATTCCTTATGGGCGAACACATGCTAGGAGCACA
     GGTACAAGATATGTCTCTCCTGAAAAGGGGACTGCATTGACCTCCTGCTTCTCAGGAGGA
     ATTTAATGCTAGATATGCATCAACAGAGTTTATCAAAATTGGTTTGAATTATTGGATTAG
     [T,C]
     CTTTAAATAGTTATCAGGGAGGCTCACTCTTTGCCTGATAATTCTCTGAAGACAGACAGG
     AACCTAAAAATACAAACAGCAAGACTGATCTTGCTAACTGCAACCAGAGGTACTTGTTAG
     GGTGTAAACAGAAAGGCAGAGCCTGCATTTTGTCACCTCATTACTGATTTATCATGTGGA
     AAATTGCTTTGTCCCAGGAAAATGGATCCTCTCATTGTCAGAAGGAGATTTTCTAGGTTG
     TATGAAATTGACTCTGGGGCACCCAAGAAGAACCTCTCCTGCTCCCACTAAAATTAAGGG
```

4945
```
     AATTGACTCTGGGGCACCCAAGAAGAACCTCTCCTGCTCCCACTAAAATTAAGGGGCCTC
     CCTCTGCAGGATAAAAAACAATCTAGTTAAATGACAACGCATTTCTGAAAAGTTTTCCAG
     GACTGAAAACCTTAACATCCACATACACTTTGATCTAAGGGACAGACGGTTCATAGAATG
     AAAGAGTATGGTGTCAATAAGGCTTGAATTCTAGAATGAGGAGCCAGCCATGCCATAGCA
     GGGGAATGATACTCCTTAAAAGGGAAAATTTAACTACAAATCCTCTGAAGTAGAAATGAT
     [A,G]
     AGAATAACCAAAATATCTGCAATGGTTCAATAGCAAATAATTTATTGGCAGCTGCTTACC
     GTGTTCATTTTGCATCTTTTTTCCCACCACACATATTAAGGAGCAGCTGAAGTCATGTTT
     GACATTCTCTCCCTCTTTTATCTCCAGTTTCAGAATGAAAAATGAGAGTGAGATATGAGT
     AGTTTTACTAGTTAAAATATGAAACACCCAGTTAAATTTGAAGGTCAGATAAACAACAAA
     TAATTTTGTATAAGTCTCATTTTAAGATAATACTAAAAAGTCATTATTTATTCACTATTA
```

5056
```
     GTTTTCCAGGACTGAAAACCTTAACATCCACATACACTTTGATCTAAGGGACAGACGGTT
     CATAGAATGAAAGAGTATGGTGTCAATAAGGCTTGAATTCTAGAATGAGGAGCCAGCCAT
     GCCATAGCAGGGGAATGATACTCCTTAAAAGGGAAAATTTAACTACAAATCCTCTGAAGT
```

FIG. 3-17

```
        AGAAATGATAAGAATAACCAAAATATCTGCAATGGTTCAATAGCAAATAATTTATTGGCA
        GCTGCTTACCGTGTTCATTTTGCATCTTTTTTCCCACCACACATATTAAGGAGCAGCTGA
        [A,G]
        GTCATGTTTGACATTCTCTCCCTCTTTTATCTCCAGTTTCAGAATGAAAAATGAGAGTGA
        GATATGAGTAGTTTTACTAGTTAAAATATGAAACACCCAGTTAAATTTGAAGGTCAGATA
        AACAACAAATAATTTTGTATAAGTCTCATTTTAAGATAATACTAAAAAGTCATTATTTAT
        TCACTATTATCACTATTTATAAAATTTTGTAGAGCATCCTGGATCTTTTTGCTTACTTTT
        GTTTTTATTTTTTGCTAAATCTGGCAATCCCAGGCACATGTGTGAAGGAGCTGTGAAATA

5280    AAATAATTTATTGGCAGCTGCTTACCGTGTTCATTTTGCATCTTTTTTCCCACCACACAT
        ATTAAGGAGCAGCTGAAGTCATGTTTGACATTCTCTCCCTCTTTTATCTCCAGTTTCAGA
        ATGAAAAATGAGAGTGAGATATGAGTAGTTTTACTAGTTAAAATATGAAACACCCAGTTA
        AATTTGAAGGTCAGATAAACAACAAATAATTTTGTATAAGTCTCATTTTAAGATAATACT
        AAAAAGTCATTATTTATTCACTATTATCACTATTTATAAAATTTTGTAGAGCATCCTGGA
        [T,A]
        CTTTTTGCTTACTTTTGTTTTTATTTTTTGCTAAATCTGGCAATCCCAGGCACATGTGTG
        AAGGAGCTGTGAAATATAAAAGGAGAAAACTTTTATGGGAAAGATTTGGCTTAAGGAGAG
        ATAATTTTGGAAAGATTTAGAATTAAAGATCATTCATTAGATGTAATGTTCTAAATACTT
        TATATCAGTTAAACTTCTCATCAACAATATGAGATGGGTACCACTAATAGTCACCATTTC
        ACAAATGATGAAATTAAGGCACAACCGGTTATGTTAAGAGGCCTAAAGTCCACAAATAGC

5790    TGAGATGGGTACCACTAATAGTCACCATTTCACAAATGATGAAATTAAGGCACAACCGGT
        TATGTTAAGAGGCCTAAAGTCCACAAATAGCAAGCTGACAGACCAGAATTTAAGCCCAGG
        CATGCTGGCTCCAGAGCCTGTGCTCTTAGTCATTAAATTATAGTGCCTTACTTGACCTTC
        CACCCTGGTTACTTTGGATCTCCCTGAATGCTCTCTCTCCCTCAGAAATACTGGAAGTTG
        GCAGAGGGACACTGAGCTGAGCATATTATTGTAGTTTTTAAATGCTCTCCACTGGACAGA
        [A,G]
        GATGGGGGATTTGAATAGAAATTTGGTGAGGAACTAATCAGTGTCCATTTACACTCACCT
        CCTCTTCCTCCCTGGAAGAGCTATAGGACTTGAGTAAGCATGATAAATTTCGTGTCTTTG
        TAAACCACACCCAGGAAATTTGTATATACAAATACATAGAGCACAGTAGTTATCAGGACA
        GACTTTGACATAAAAAGAACTGGGTTTGAGTCCCTGCTCTGGCCTTCTTATCTGGGTGGC
        CCTCTGGGAAAGTTACTTAACTACATAAAGTTTTGTTTCCATATCTACAAAATGAGGTTT

5901    AAGCCCAGGCATGCTGGCTCCAGAGCCTGTGCTCTTAGTCATTAAATTATAGTGCCTTAC
        TTGACCTTCCACCCTGGTTACTTTGGATCTCCCTGAATGCTCTCTCTCCCTCAGAAATAC
        TGGAAGTTGGCAGAGGGACACTGAGCTGAGCATATTATTGTAGTTTTTAAATGCTCTCCA
        CTGGACAGAAGATGGGGGATTTGAATAGAAATTTGGTGAGGAACTAATCAGTGTCCATTT
        ACACTCACCTCCTCTTCCTCCCTGGAAGAGCTATAGGACTTGAGTAAGCATGATAAATTT
        [C,T]
        GTGTCTTTGTAAACCACACCCAGGAAATTTGTATATACAAATACATAGAGCACAGTAGTT
        ATCAGGACAGACTTTGACATAAAAAGAACTGGGTTTGAGTCCCTGCTCTGGCCTTCTTAT
        CTGGGTGGCCCTCTGGGAAAGTTACTTAACTACATAAAGTTTTGTTTCCATATCTACAAA
        ATGAGGTTTCTCAAAATAGCAGCTAGTTTATAGAGTTGTTGCAAGAATTTAGTAAGCTAA
        TACATATAAATACGTCAACATAGCACCAGGTACAAAAATATGTGCTCAAGAAACTGAAGT
```

FIG. 3-18

6457 CAACATAGCACCAGGTACAAAAATATGTGCTCAAGAAACTGAAGTTACCTGATTATAATG
CTCTATACTATTGACAAGGGAAAAGTGAAAACAGTTTTTGTTTTACCATGTGTGTATGTG
TGTGTGTCTGTGATGTTTCCGACATGCTCTATTTAACATAAATTACTCTCACTCTTTCTC
TCTCTCTCTTTCTCTTTCTCCCTCTCTCATCTTACCCTTTCCCCCACCAGGTCCCCGGCC
AGTTGTGTATATGCAGCATGCCCTGTTTGCAGACAATGCCTACTGGCTTGAGAATTATGC
[C,T]
AATGGAAGCCTTGGATTCCTTCTAGCAGATGCAGGTTATGATGTATGGATGGGAAACAGT
CGGGGAAACACTTGGTCAAGAAGACACAAAACACTCTCAGAGACAGATGAGAAATTCTGG
GCCTTTAGGTAAATATTAGCTAAGAAAACTCAAGGGGGAAATTGGAGGCAATTTTAAAAA
AATAACGTGGACGCTATTAATGATTATCTTTGACGCTTGAAGTCATATAGCTCCTTGTAG
TTTCTGTTAAGATCTCAAAGGAGGGTAACAGCAAGAAGCTCTGATTTTTCACTGATTCTC

6632 TTCTCTCTCTCTCTTTCTCTTTCTCCCTCTCTCATCTTACCCTTTCCCCCACCAGGTCCC
CGGCCAGTTGTGTATATGCAGCATGCCCTGTTTGCAGACAATGCCTACTGGCTTGAGAAT
TATGCCAATGGAAGCCTTGGATTCCTTCTAGCAGATGCAGGTTATGATGTATGGATGGGA
AACAGTCGGGGAAACACTTGGTCAAGAAGACACAAAACACTCTCAGAGACAGATGAGAAA
TTCTGGGCCTTTAGGTAAATATTAGCTAAGAAAACTCAAGGGGGAAATTGGAGGCAATTT
[T,A]
AAAAAAATAACGTGGACGCTATTAATGATTATCTTTGACGCTTGAAGTCATATAGCTCCT
TGTAGTTTCTGTTAAGATCTCAAAGGAGGGTAACAGCAAGAAGCTCTGATTTTTCACTGA
TTCTCCCACAAGCAAAGTATGGCATTTCAACAAGATCATTTTTACATCCAATTCTGTGAA
TTCTATGCATTAAAAGTATGTCCAAAGAGACAGCTCAGGAAATTATCATGACCAATGTGC
ACATTCATTCAGCCAATGTTTACTGAGTGGCTACTGTATGCGCTGTTCTAGGCCCCGAAC

6763 AAGCCTTGGATTCCTTCTAGCAGATGCAGGTTATGATGTATGGATGGGAAACAGTCGGGG
AAACACTTGGTCAAGAAGACACAAAACACTCTCAGAGACAGATGAGAAATTCTGGGCCTT
TAGGTAAATATTAGCTAAGAAAACTCAAGGGGGAAATTGGAGGCAATTTTAAAAAAATAA
CGTGGACGCTATTAATGATTATCTTTGACGCTTGAAGTCATATAGCTCCTTGTAGTTTCT
GTTAAGATCTCAAAGGAGGGTAACAGCAAGAAGCTCTGATTTTTCACTGATTCTCCCACA
[A,G]
GCAAAGTATGGCATTTCAACAAGATCATTTTTACATCCAATTCTGTGAATTCTATGCATT
AAAAGTATGTCCAAAGAGACAGCTCAGGAAATTATCATGACCAATGTGCACATTCATTCA
GCCAATGTTTACTGAGTGGCTACTGTATGCGCTGTTCTAGGCCCCGAACATTCAAACAGG
GAACAGACAAACTCTGACCTCACAAAGCTTATGTTCATTTTAGTGATAATTTTACAAGTC
ATTGCTCCTGGATTGCCAATCAACTGTGTAAAGATGATTTGGACCAGGACCTTATTGATT

6955 TAATGATTATCTTTGACGCTTGAAGTCATATAGCTCCTTGTAGTTTCTGTTAAGATCTCA
AAGGAGGGTAACAGCAAGAAGCTCTGATTTTTCACTGATTCTCCCACAAGCAAAGTATGG
CATTTCAACAAGATCATTTTTACATCCAATTCTGTGAATTCTATGCATTAAAAGTATGTC
CAAAGAGACAGCTCAGGAAATTATCATGACCAATGTGCACATTCATTCAGCCAATGTTTA
CTGAGTGGCTACTGTATGCGCTGTTCTAGGCCCCGAACATTCAAACAGGGAACAGACAAA
[-,T,C]
TCTGACCTCACAAAGCTTATGTTCATTTTAGTGATAATTTTACAAGTCATTGCTCCTGGA
TTGCCAATCAACTGTGTAAAGATGATTTGGACCAGGACCTTATTGATTTAGAGAAACTGT
GATTGATTTAGAGAAACTGAGATCGCACATAGTACCATTTTCAGGAAAACTCCAATATTA

FIG. 3-19

```
              GATTTTTAAAACCTTGTTAATGGGCAATGAAGAAGAATCTTTTTTGATATCTTGTTTCTT
              TTAATGGAAGAGTTTTCTGCTGTCACCAGAGGACAGGCTGATGCCTGCGATAGACTTTTC

7017     GGAGGGTAACAGCAAGAAGCTCTGATTTTTCACTGATTCTCCCACAAGCAAAGTATGGCA
              TTTCAACAAGATCATTTTTACATCCAATTCTGTGAATTCTATGCATTAAAAGTATGTCCA
              AAGAGACAGCTCAGGAAATTATCATGACCAATGTGCACATTCATTCAGCCAATGTTTACT
              GAGTGGCTACTGTATGCGCTGTTCTAGGCCCCGAACATTCAAACAGGGAACAGACAAACT
              CTGACCTCACAAAGCTTATGTTCATTTTAGTGATAATTTTACAAGTCATTGCTCCTGGAT
              [T,G]
              GCCAATCAACTGTGTAAAGATGATTTGGACCAGGACCTTATTGATTTAGAGAAACTGTGA
              TTGATTTAGAGAAACTGAGATCGCACATAGTACCATTTTCAGGAAAACTCCAATATTAGA
              TTTTTAAAACCTTGTTAATGGGCAATGAAGAAGAATCTTTTTTGATATCTTGTTTCTTTT
              AATGGAAGAGTTTTCTGCTGTCACCAGAGGACAGGCTGATGCCTGCGATAGACTTTTCTT
              TCTTCAGGCCTAAGCTCCCTGTTGGTTTGTAAACCTGATGCTAGAACAGACTGTGTATTC

7151     GAAATTATCATGACCAATGTGCACATTCATTCAGCCAATGTTTACTGAGTGGCTACTGTA
              TGCGCTGTTCTAGGCCCCGAACATTCAAACAGGGAACAGACAAACTCTGACCTCACAAAG
              CTTATGTTCATTTTAGTGATAATTTTACAAGTCATTGCTCCTGGATTGCCAATCAACTGT
              GTAAAGATGATTTGGACCAGGACCTTATTGATTTAGAGAAACTGTGATTGATTTAGAGAA
              ACTGAGATCGCACATAGTACCATTTTCAGGAAAACTCCAATATTAGATTTTTAAAACCTT
              [G,T]
              TTAATGGGCAATGAAGAAGAATCTTTTTTGATATCTTGTTTCTTTTAATGGAAGAGTTTT
              CTGCTGTCACCAGAGGACAGGCTGATGCCTGCGATAGACTTTTCTTTCTTCAGGCCTAAG
              CTCCCTGTTGGTTTGTAAACCTGATGCTAGAACAGACTGTGTATTCCTATTACATTAATA
              AAACATTCAGTACCCACTGAAAGTTTGAGAATAGTGGAGGAATAGAATAGAATGTTATAG
              TCTGAGTTCTTGGGCAGGGGCAAGCATCAGGAAATATTGAATCATTAGTCTTTAGGAGGT

7308     CTCCTGGATTGCCAATCAACTGTGTAAAGATGATTTGGACCAGGACCTTATTGATTTAGA
              GAAACTGTGATTGATTTAGAGAAACTGAGATCGCACATAGTACCATTTTCAGGAAAACTC
              CAATATTAGATTTTTAAAACCTTGTTAATGGGCAATGAAGAAGAATCTTTTTTGATATCT
              TGTTTCTTTTAATGGAAGAGTTTTCTGCTGTCACCAGAGGACAGGCTGATGCCTGCGATA
              GACTTTTCTTTCTTCAGGCCTAAGCTCCCTGTTGGTTTGTAAACCTGATGCTAGAACAGA
              [C,G]
              TGTGTATTCCTATTACATTAATAAAACATTCAGTACCCACTGAAAGTTTGAGAATAGTGG
              AGGAATAGAATAGAATGTTATAGTCTGAGTTCTTGGGCAGGGGCAAGCATCAGGAAATAT
              TGAATCATTAGTCTTTAGGAGGTGTCACAACAATTCTCCTATTCTTGTAAGTCCCAATCT
              ATAGATTTCCTCACATGTTCTTTTAATAAACAGGCTTCTAGCTTATGGAATACCTGATTT
              GACTAAATGTTATATAGGCCCTTTTGTTCCTCCTGTCTGAAGAACAAAATACTAGTACTA

7321     AATCAACTGTGTAAAGATGATTTGGACCAGGACCTTATTGATTTAGAGAAACTGTGATTG
              ATTTAGAGAAACTGAGATCGCACATAGTACCATTTTCAGGAAAACTCCAATATTAGATTT
              TTAAAACCTTGTTAATGGGCAATGAAGAAGAATCTTTTTTGATATCTTGTTTCTTTTAAT
              GGAAGAGTTTTCTGCTGTCACCAGAGGACAGGCTGATGCCTGCGATAGACTTTTCTTTCT
              TCAGGCCTAAGCTCCCTGTTGGTTTGTAAACCTGATGCTAGAACAGACTGTGTATTCCTA
              [T,C]
```

FIG. 3-20

```
         TACATTAATAAAACATTCAGTACCCACTGAAAGTTTGAGAATAGTGGAGGAATAGAATAG
         AATGTTATAGTCTGAGTTCTTGGGCAGGGGCAAGCATCAGGAAATATTGAATCATTAGTC
         TTTAGGAGGTGTCACAACAATTCTCCTATTCTTGTAAGTCCCAATCTATAGATTTCCTCA
         CATGTTCTTTTAATAAACAGGCTTCTAGCTTATGGAATACCTGATTTGACTAAATGTTAT
         ATAGGCCCTTTTGTTCCTCCTGTCTGAAGAACAAAATACTAGTACTATGGAATATTGGTA

7542     GCGATAGACTTTTCTTTCTTCAGGCCTAAGCTCCCTGTTGGTTTGTAAACCTGATGCTAG
         AACAGACTGTGTATTCCTATTACATTAATAAAACATTCAGTACCCACTGAAAGTTTGAGA
         ATAGTGGAGGAATAGAATAGAATGTTATAGTCTGAGTTCTTGGGCAGGGGCAAGCATCAG
         GAAATATTGAATCATTAGTCTTTAGGAGGTGTCACAACAATTCTCCTATTCTTGTAAGTC
         CCAATCTATAGATTTCCTCACATGTTCTTTTAATAAACAGGCTTCTAGCTTATGGAATAC
         [C,T]
         TGATTTGACTAAATGTTATATAGGCCCTTTTGTTCCTCCTGTCTGAAGAACAAAATACTA
         GTACTATGGAATATTGGTATATATTAAATATATATCTATATATCCATGTGGACAGGAATA
         CTACTACTAACAACATCTTACTGAGCACCCACTGGCAGCCAGAGTCGTTTCTTTCATACT
         ATTAAACCCCGTTAGCAGCCCCGTAAACCAGGTACTACCCTGTTTATTTCCCAAATGAGA
         AAACATAGGCTCAGAGCATTTCAGTAATTTCTCAAGAGTTGCAAAGGCCATAAATAGTAG

8597     ATAAAACTGGTCAGGAGAAATTGTATTTCATTGGACATTCACTTGGCACTACAATAGGTA
         TGTTTATGAGGGTCACTGTTAGGTGTGTTTTTGAGGGTCAGTTTTCTCAGAGTCTTACAG
         GAGTTCACCTTTATGTTGGAATAAAACAACTGTTACTTATAGTGCCCTCAATTCCCTGTC
         CTCTGCTGGGAATAACCCTAGTACTCTAAGTAGCTGTGAGCCTGCAGTGCACAGACTATA
         TGTAGGGCAAACCTTTCCTGGGTCTCTGGTCACAGCAGCATATTGACTACGGTGATGCAA
         [T,C]
         TTCCCAGGAATAACATGTGTTCCAAATTCAAAGAAATAATTCCACAGAGTAAGTTTCTAG
         ATTCCCTCTGAGCTGAAAAAGTAAAATTCAATGCCATGGAATATGGCTGAAACATAATAA
         ATGTGCATCAATCATCTCTTTCTCACAACCCAAATGGGATTTTTAAAAAATAAAAGGGAA
         GGGCTTATACCTATATTTAAACAAATTGAAAAGGCATGGTTATATTTGTTTGTGAGTTGG
         AACACACAAGCTTACTATAATAAATCAATTGAGCTTATCTATTCAGTGTGTGATTTAGTA

8803     TAAGTAGCTGTGAGCCTGCAGTGCACAGACTATATGTAGGGCAAACCTTTCCTGGGTCTC
         TGGTCACAGCAGCATATTGACTACGGTGATGCAATTTCCCAGGAATAACATGTGTTCCAA
         ATTCAAAGAAATAATTCCACAGAGTAAGTTTCTAGATTCCCTCTGAGCTGAAAAAGTAAA
         ATTCAATGCCATGGAATATGGCTGAAACATAATAAATGTGCATCAATCATCTCTTTCTCA
         CAACCCAAATGGGATTTTTAAAAAATAAAAGGGAAGGGCTTATACCTATATTTAAACAAA
         [C,T]
         TGAAAAGGCATGGTTATATTTGTTTGTGAGTTGGAACACACAAGCTTACTATAATAAATC
         AATTGAGCTTATCTATTCAGTGTGTGATTTAGTATTTATGAAATAGCAAGTAAATGTAAG
         CACTATGTAGAAATTTCTAAAGTTTTTTAAGCTGACAACTTACTTCTTAATTTACTTACT
         TTACTTAATTTACTTTACAATTTACTTTCCAGGTATTTTGGAAAGAAATCAATAATCTAG
         TTCCAAGTAAAAGTTGAAAGGAACCCACACTAATAAAAGCTTTGAATTTGTCATTGAACT

9016     AAATGTGCATCAATCATCTCTTTCTCACAACCCAAATGGGATTTTTAAAAAATAAAGGG
         AAGGGCTTATACCTATATTTAAACAAATTGAAAAGGCATGGTTATATTTGTTTGTGAGTT
         GGAACACACAAGCTTACTATAATAAATCAATTGAGCTTATCTATTCAGTGTGTGATTTAG
```

FIG. 3-21

TATTTATGAAATAGCAAGTAAATGTAAGCACTATGTAGAAATTTCTAAAGTTTTTTAAGC
TGACAACTTACTTCTTAATTTACTTACTTTACTTAATTTACTTTACAATTTACTTTCCAG
[G,A]
TATTTTGGAAAGAAATCAATAATCTAGTTCCAAGTAAAAGTTGAAAGGAACCCACACTAA
TAAAAGCTTTGAATTTGTCATTGAACTTCCACTAAAGTTTCCAATTTTAAGAGAATAAAT
CATGTGAAAGTGCAATATTTCAGTTTAGGGAAATATTTTCATTATCACCACTATCATCAG
TAACAAACATATATTCATTAGTATTTTAGATTGACAGGCACTTTCCAAGCTCAGAACAGG
CAGTTAGCATCAGTCAGCATATACTAAAAAAGTATCAAAGAACTCATAGGAGATCAAAAA

9967  GTTTCATTTAGGACATAAATATTTTTAGTGACTGTTGTTTGCATTTTGGACAGAGCAATT
TCTGTTATGTAAGGAGCACCCACTCTTTGTAGGACATTTAGTAGGTCCCAGCCCATTAAA
CAGGGCTCTGCAGTCAGCGTGACCCTCAAAAATCTCACCTCCACACATTTCCAAACACCC
TCTGGGGAAGTACTATTCCTGATTCAGAGTCTTTTTATCAATTGTTCAGTCAATTATTTC
AGTTCTTCTTTTTCTGGCCAAGACAGTTTTAATGTTCCAACAAGTGTTTCAGTACACACA
[T,C]
ACACACACACACACACACACACACACACACATGCTAGTGGAGGCCCAGGAAGGG
ACCTCTGGAAACCAAATTATATGGATATTCTCCCTAGCCTACCCAGTGTTGTGCTAATCT
CCATCCTCACAGATATACAAAGGGGTGCAATGCTACTGCTGAAAGAGCAAAGCAAATGGA
GATGCCTGGTCCTTACTGGGCCATCGTGGATGCTAGGGAAAGCCCCTTTCTTTTTGGAAA
CAGGGAAGAGTCTAGAGGGTTGAAAAACACCCAGTAAGACACTGGGAGCAGTGAAATTTC

10008 CATTTTGGACAGAGCAATTTCTGTTATGTAAGGAGCACCCACTCTTTGTAGGACATTTAG
TAGGTCCCAGCCCATTAAACAGGGCTCTGCAGTCAGCGTGACCCTCAAAAATCTCACCTC
CACACATTTCCAAACACCCTCTGGGGAAGTACTATTCCTGATTCAGAGTCTTTTTATCAA
TTGTTCAGTCAATTATTTCAGTTCTTCTTTTTCTGGCCAAGACAGTTTTAATGTTCCAAC
AAGTGTTTCAGTACACACATACACACACACACACACACACACACACACACACACATGC
[C,T]
AGTGGAGGCCCAGGAAGGGACCTCTGGAAACCAAATTATATGGATATTCTCCCTAGCCTA
CCCAGTGTTGTGCTAATCTCCATCCTCACAGATATACAAAGGGGTGCAATGCTACTGCTG
AAAGAGCAAAGCAAATGGAGATGCCTGGTCCTTACTGGGCCATCGTGGATGCTAGGGAAA
GCCCCTTTCTTTTTGGAAACAGGGAAGAGTCTAGAGGGTTGAAAAACACCCAGTAAGACA
CTGGGAGCAGTGAAATTTCATTCCATAGTGAGAAAGAAAACCTGTTAGAATAACTGGGTG

10363 AGCCTACCCAGTGTTGTGCTAATCTCCATCCTCACAGATATACAAAGGGGTGCAATGCTA
CTGCTGAAAGAGCAAAGCAAATGGAGATGCCTGGTCCTTACTGGGCCATCGTGGATGCTA
GGGAAAGCCCCTTTCTTTTTGGAAACAGGGAAGAGTCTAGAGGGTTGAAAAACACCCAGT
AAGACACTGGGAGCAGTGAAATTTCATTCCATAGTGAGAAAGAAAACCTGTTAGAATAAC
TGGGTGATGCTGCAGAAAGAAATCAATTCACCTCCTGTGACTGATTATTTGCTTCTGGAA
[G,A]
CTCTGTGATTCATTCTGGCATCTCAGAGTTAGGGATGAAATGAGAATGTTGCCAGCATTT
ACCCCATGCTTGGGAAGTTTACACAGCAGTAGCTACTCCAGCAGCTTAACCATCACCTTT
CCCCTGCCAACTACTCCATTTCCCCCAATCAAGTCAAACTGTCCATAAATAGAATAAAAT
AAAATTGGAGACTTGAGAGCAGAGAAGACTGAAGGCAGATTATCTTTATAGAATAACTCA
GAAGACTTCCAATTCATCCCCAGTATGATCACGATAGAAGGAAAAAATGACTAAGCAGAG

FIG. 3-22

10684  TCTCAGAGTTAGGGATGAAATGAGAATGTTGCCAGCATTTACCCCATGCTTGGGAAGTTT
ACACAGCAGTAGCTACTCCAGCAGCTTAACCATCACCTTTCCCCTGCCAACTACTCCATT
TCCCCCAATCAAGTCAAACTGTCCATAAATAGAATAAAATAAAATTGGAGACTTGAGAGC
AGAGAAGACTGAAGGCAGATTATCTTTATAGAATAACTCAGAAGACTTCCAATTCATCCC
CAGTATGATCACGATAGAAGGAAAAAATGACTAAGCAGAGCCCCAATTTTGTTAGAAACA
[T,C]
TGCGTAAGTATTTATTTTTACAAGATTGTCTTATCTCCTGTTCTCTCAGGGTTTGTAGCC
TTTTCCACCATGCCTGAACTGGCACAAAGAATCAAAATGAATTTTGCCTTGGGTCCTACG
ATCTCATTCAAATATCCCACGGGCATTTTTACCAGGTTTTTTCTACTTCCAAATTCCATA
ATCAAGGTAGGCTCCTTTCAACAAAATGTACCTGAGGATCTCATTTTGGATCATAAATCC
TTATTATTTTCAAATCTACTGTAAAGTAAAAGTAGGAAATTTAGATAAAATCTATAGAAC

11177  TCCTTTCAACAAAATGTACCTGAGGATCTCATTTTGGATCATAAATCCTTATTATTTTCA
AATCTACTGTAAAGTAAAAGTAGGAAATTTAGATAAAATCTATAGAACTTAGACTCTGTG
GGTATGTGCTTGTGTATGTGTGTCCCTGCGTGTGCGCATGTCTGTGCCATAGTATCTGCA
GGTTCTGTAATACAATTTACTATACAAGGTCATCAGCAGGCTGAGTATATGTCAGAATTT
CTAGCTGAACTGAGTGCTATATGACAACAAGGATTTTTCTTGTTTTCCCAAGTGTTTTTT
[G,T]
TTCCATTTAGTCAGGTAGGTCAATGAATTCACATTGCCCAAATGAAAGACACTTCAAGTT
ACCCATAATCACTGATGTGTCCAATTTTGACATTAGAAAAACCTGATTAATATATTCCTT
CCAATATGGAAACTTGCCCTAATAACTAAAGCTAAGATTCCAAAGCCTAAATGTATTACA
GCTCAAGTATTAATTCAAATATTTATTGGTTATTTTTCAGGAGTTGAAAAAGTCATTTGG
TTGCCAATTGTGGATTTGGGATTTTATCTATTAAAGGGTTTTTTTTTTTTTCTCTTTGC

12345  TTTAAGTCCCATATCCTGCTCTTTTCTTCCGTCAGTTTCCCCCAGAAGCTCCAAGACCCC
ACCAGGAATCCCCATCCAAGTTTACTTTCCCAACTCCTGGAAGTTTCAATTGTGCTGCCT
TTGTGACATTATCATATCTTTTCTGTTCAATGGTTGCTTCTCTTTGGCTCACTGTTCTCT
ACTTTTCAGCCTGAGAGCTGGCTAATCTGGGACAGTACTCGAATGCAGTGTACACATGGG
TAACATGGAAAACCCCGATTTTCCCTTATATTCAAGGTATTATTTGACCTTAAGAAAAAC
[T,C]
GTTTTACATTTCATACCAATTAATGAGAAAAAAATATTGGCAAGCACTGACTGGGCAGAA
TACAGGGAAGCTTCACTATGGAGAAGTGAATTTGGGATTGAGGGCCTTTATTGCAATCTC
CTTGTAAATAATATTTGATACTCTTCCTCATCTGGAGACACATTCCTAAGTAACTTTTCC
TGAATAATTTGGTCTCCTTGACTGAATCAGTAAGTACAAATAGATCCCCAAGCATGGCTC
TTTCCTAGAATGAAAGAAATGTCAAGAAGTCTGAAGATGATTCTTGAATTTTGGTTTTTT

12349  AGTCCCATATCCTGCTCTTTTCTTCCGTCAGTTTCCCCCAGAAGCTCCAAGACCCCACCA
GGAATCCCCATCCAAGTTTACTTTCCCAACTCCTGGAAGTTTCAATTGTGCTGCCTTTGT
GACATTATCATATCTTTTCTGTTCAATGGTTGCTTCTCTTTGGCTCACTGTTCTCTACTT
TTCAGCCTGAGAGCTGGCTAATCTGGGACAGTACTCGAATGCAGTGTACACATGGGTAAC
ATGGAAAACCCCGATTTTCCCTTATATTCAAGGTATTATTTGACCTTAAGAAAAACTGTT
[C,T]
TACATTTCATACCAATTAATGAGAAAAAAATATTGGCAAGCACTGACTGGGCAGAATACA
GGGAAGCTTCACTATGGAGAAGTGAATTTGGGATTGAGGGCCTTTATTGCAATCTCCTTG
TAAATAATATTTGATACTCTTCCTCATCTGGAGACACATTCCTAAGTAACTTTTCCTGAA

FIG. 3-23

```
         TAATTTGGTCTCCTTGACTGAATCAGTAAGTACAAATAGATCCCCAAGCATGGCTCTTTC
         CTAGAATGAAAGAAATGTCAAGAAGTCTGAAGATGATTCTTGAATTTTGGTTTTTTGCTA
```

13115
```
         TAGAAGATAAGAAAACGAAGATAGCTTCTACCAAAATCTGCAACAATAAGATACTCTGGT
         TGATATGTAGCGAATTTATGTCCTTATGGGCTGGATCCAACAAGAAAAATATGAATCAGG
         TATGTATGATAATTATAGGGCCATTTGATACCTTAAGAAATTCCAGCTTTCCTTTGACTC
         ATTTTGATATATCTATTTACTGTATAAATTCATATGGTATTCCAAACCCTTAAAGACAGA
         TTTTTTTTTGCTTTTAAAAATGTTTATGGGTATATAATAGTTGTACATATTTATGAGACA
         [C,T]
         ATATATTTTGATATAAGCATACAATGTGTAATGACCAAATCAGGGTAATTGGGATATCCA
         TCACCTCAAGCATTTATCATTTCTTTTTGTTAGAGACATTCTAATTTGACTCTTCTAGTT
         ATTTTGAAATATACAATGAATTATTGTTAACTATAGTCATCCTATTGTGCATGCCAGACT
         TTAGTCCTTCTAACGGTATTTTGGTACCCATTAACCAATGCCTCTTTATCCTTCCCCCAC
         CCCTACTACCTTTCCCAGCCTCTGGTAACCATCATTCTTCTCACTATCTCTATAAGGTCA
```

13354
```
         ATTTTTTTTTGCTTTTAAAAATGTTTATGGGTATATAATAGTTGTACATATTTATGAGAC
         ACATATATTTTGATATAAGCATACAATGTGTAATGACCAAATCAGGGTAATTGGGATATC
         CATCACCTCAAGCATTTATCATTTCTTTTTGTTAGAGACATTCTAATTTGACTCTTCTAG
         TTATTTTGAAATATACAATGAATTATTGTTAACTATAGTCATCCTATTGTGCATGCCAGA
         CTTTAGTCCTTCTAACGGTATTTTGGTACCCATTAACCAATGCCTCTTTATCCTTCCCCC
         [T,A]
         CCCCTACTACCTTTCCCAGCCTCTGGTAACCATCATTCTTCTCACTATCTCTATAAGGTC
         AGTTTTTTTTTAAACTCCCCTATATGAGTGAGAACATGCAGTATTTGTCTTTTTGTGCCT
         GGCTTATTTCACTTAATGTAATGTTCTCTAATTTCATCCACATTATTGCAAATGACATGA
         TTTCATTCTTCTTATGGCTGTCTATATGTACCACATTTTATTTATCCACTCATCTGTTGA
         TGGACACTTAGGCTGATTTCATATCTTGGTCATTGTGAATAGTGCTGTACTAAACATGGG
```

13373
```
         AATGTTTATGGGTATATAATAGTTGTACATATTTATGAGACACATATATTTTGATATAAG
         CATACAATGTGTAATGACCAAATCAGGGTAATTGGGATATCCATCACCTCAAGCATTTAT
         CATTTCTTTTTGTTAGAGACATTCTAATTTGACTCTTCTAGTTATTTTGAAATATACAAT
         GAATTATTGTTAACTATAGTCATCCTATTGTGCATGCCAGACTTTAGTCCTTCTAACGGT
         ATTTTGGTACCCATTAACCAATGCCTCTTTATCCTTCCCCCACCCCTACTACCTTTCCCA
         [C,G]
         CCTCTGGTAACCATCATTCTTCTCACTATCTCTATAAGGTCAGTTTTTTTTTAAACTCCC
         CTATATGAGTGAGAACATGCAGTATTTGTCTTTTTGTGCCTGGCTTATTTCACTTAATGT
         AATGTTCTCTAATTTCATCCACATTATTGCAAATGACATGATTTCATTCTTCTTATGGCT
         GTCTATATGTACCACATTTTATTTATCCACTCATCTGTTGATGGACACTTAGGCTGATTT
         CATATCTTGGTCATTGTGAATAGTGCTGTACTAAACATGGGGGTGCAGATGTCTCTTCCA
```

14677
```
         AGAGATAGAGATCTAATTTCATTCTTCTGCATATGGATATCTAGTTTTCCCAGCATCATT
         TCTTGTGGAAATTGTCCTTTGCCCAATGTATGTTCTTGATGCCTTTGTTGAAAATTAGTT
         GACTATAAATGTGTGGATTTATTTGTGGGTTCTTTATTCTGTTCCATTGGTCTATGTGTC
         TGTTTTTATGCCAGTATCATGCAGTTTTGATTATTACAGGTTTGTAGTATAATTTGAAGT
         CAGGTCATGTGATGCCTCCAGCTTTGTTCTTTTTTCTCAGAATCTTATATTTTAGAAAAAC
         [C,G]
```

FIG. 3-24

TAAAGACTCCAACAAAAAACCTGCTAGAACTGATAAACAAATTCATTAAATTTGCAGGAT
ACAACATCAACATACAAAATTCAGCAGCATTTCAATATGCCAAGAGCAAATAATCTTAAA
AAAAAGAAAGAAAAAAAAACAAGAAATAATCCCATTTATAATAGCTACAAATAAAATAAA
ACACCTAGGAATAAACCATACCAAAGAAGTGAAAGATTTCTACAATGAAAACTATAAAAC
ACTGATGAAAGAAATTGAAAATGACATTAAAAAATGGAAAGGTATTCCATGTTCATGGAT

14734    ATTTCTTGTGGAAATTGTCCTTTGCCCAATGTATGTTCTTGATGCCTTTGTTGAAAATTA
GTTGACTATAAATGTGTGGATTTATTTGTGGGTTCTTTATTCTGTTCCATTGGTCTATGT
GTCTGTTTTTATGCCAGTATCATGCAGTTTTGATTATTACAGGTTTGTAGTATAATTTGA
AGTCAGGTCATGTGATGCCTCCAGCTTTGTTCTTTTTTCTCAGAATCTTATATTTAGAAA
AACGTAAAGACTCCAACAAAAAACCTGCTAGAACTGATAAACAAATTCATTAAATTTGCA
[G,A]
GATACAACATCAACATACAAAATTCAGCAGCATTTCAATATGCCAAGAGCAAATAATCTT
AAAAAAAGAAAGAAAAAAAAACAAGAAATAATCCCATTTATAATAGCTACAAATAAAAT
AAAACACCTAGGAATAAACCATACCAAAGAAGTGAAAGATTTCTACAATGAAAACTATAA
AACACTGATGAAAGAAATTGAAAATGACATTAAAAAATGGAAAGGTATTCCATGTTCATG
GATTGCAAGAATCAATATTGTTAAAATGTCCATATGATCCAAAACAATCTACAGATTCAA

14747    ATTGTCCTTTGCCCAATGTATGTTCTTGATGCCTTTGTTGAAAATTAGTTGACTATAAAT
GTGTGGATTTATTTGTGGGTTCTTTATTCTGTTCCATTGGTCTATGTGTCTGTTTTTATG
CCAGTATCATGCAGTTTTGATTATTACAGGTTTGTAGTATAATTTGAAGTCAGGTCATGT
GATGCCTCCAGCTTTGTTCTTTTTTCTCAGAATCTTATATTTAGAAAAACGTAAAGACTC
CAACAAAAAACCTGCTAGAACTGATAAACAAATTCATTAAATTTGCAGGATACAACATCA
[A,G]
CATACAAAATTCAGCAGCATTTCAATATGCCAAGAGCAAATAATCTTAAAAAAAGAAAG
AAAAAAAAACAAGAAATAATCCCATTTATAATAGCTACAAATAAAATAAAACACCTAGGA
ATAAACCATACCAAAGAAGTGAAAGATTTCTACAATGAAAACTATAAAACACTGATGAAA
GAAATTGAAAATGACATTAAAAAATGGAAAGGTATTCCATGTTCATGGATTGCAAGAATC
AATATTGTTAAAATGTCCATATGATCCAAAACAATCTACAGATTCAATGCAATCCCTATC

14808    TGTGGATTTATTTGTGGGTTCTTTATTCTGTTCCATTGGTCTATGTGTCTGTTTTTATGC
CAGTATCATGCAGTTTTGATTATTACAGGTTTGTAGTATAATTTGAAGTCAGGTCATGTG
ATGCCTCCAGCTTTGTTCTTTTTTCTCAGAATCTTATATTTAGAAAAACGTAAAGACTCC
AACAAAAAACCTGCTAGAACTGATAAACAAATTCATTAAATTTGCAGGATACAACATCAA
CATACAAAATTCAGCAGCATTTCAATATGCCAAGAGCAAATAATCTTAAAAAAAGAAAG
[-,A]
AAAAAAAACAAGAAATAATCCCATTTATAATAGCTACAAATAAAATAAAACACCTAGGAA
TAAACCATACCAAAGAAGTGAAAGATTTCTACAATGAAAACTATAAAACACTGATGAAAG
AAATTGAAAATGACATTAAAAAATGGAAAGGTATTCCATGTTCATGGATTGCAAGAATCA
ATATTGTTAAAATGTCCATATGATCCAAAACAATCTACAGATTCAATGCAATCCCTATCA
AAATACCAATGACATTCTTCATTGAAATAAAAAAAAGCCTAAAATTTAAGTGGAACCAT

15086    AATAATCTTAAAAAAAGAAAGAAAAAAAAACAAGAAATAATCCCATTTATAATAGCTAC
AAATAAAATAAAACACCTAGGAATAAACCATACCAAAGAAGTGAAAGATTTCTACAATGA
AAACTATAAAACACTGATGAAAGAAATTGAAAATGACATTAAAAAATGGAAAGGTATTCC

FIG. 3-25

ATGTTCATGGATTGCAAGAATCAATATTGTTAAAATGTCCATATGATCCAAAACAATCTA
CAGATTCAATGCAATCCCTATCAAAATACCAATGACATTCTTCATTGAAATAAAAAAAAA
[-,A,G]
CCTAAAATTTAAGTGGAACCATGAAGGTAGATGTCTGCTATACATAGAAGATTAAGTACT
CAACAAACCTTGAATATGAAGACTGGGGAAGTGAATAGGCAGCTTCACTCTTCTATTCCC
TGGTGAAATTTAGGAGAATGGATGTTTTATAATGGGTAGCAGTTTCTTACATGTTCTCAA
TCAGCCATAACTTACTACAGTCAATTTGAATTTATTGCATTTGAATATATTGGATTAAAA
ATAAAATCCTAAAAAAGGAGAGAAGCACATATAAACCTGCGTCTTATTTCATGTGTTCCT

15414   TAGATGTCTGCTATACATAGAAGATTAAGTACTCAACAAACCTTGAATATGAAGACTGGG
GAAGTGAATAGGCAGCTTCACTCTTCTATTCCCTGGTGAAATTTAGGAGAATGGATGTTT
TATAATGGGTAGCAGTTTCTTACATGTTCTCAATCAGCCATAACTTACTACAGTCAATTT
GAATTTATTGCATTTGAATATATTGGATTAAAAATAAAATCCTAAAAAAGGAGAGAAGCA
CATATAAACCTGCGTCTTATTTCATGTGTTCCTTTCTTTGTGGGTGACTTTTGTTTTGAA
[A,G]
TAAAACCTGCAAAATAACAGGACAGGGTGGAAGGGAGATGGGATCCCCTCTTTATGAAGA
AGCAGCAGTCCTGTTTTATCACCTCTTCATTTTCTGTTATTGAGAATTCAAGAAGAAGGA
GGAGGAAGAGTTCACATCCACAGACTGGTGTGGTTGAATAGTTGTCTCTACTGTATTCCA
AATAGCAGCCAATGAGGCTGTTACAGTGAAGCCAGTCCCAAGATAATTGTTCTGTACCCC
TATTCTCTAAGAAGCTAAATTGTGTTAGACTGAAACCCATAAGGAACCATTGTTCAAAGT

15722   TGCAAAATAACAGGACAGGGTGGAAGGGAGATGGGATCCCCTCTTTATGAAGAAGCAGCA
GTCCTGTTTTATCACCTCTTCATTTTCTGTTATTGAGAATTCAAGAAGAAGGAGGAGGAA
GAGTTCACATCCACAGACTGGTGTGGTTGAATAGTTGTCTCTACTGTATTCCAAATAGCA
GCCAATGAGGCTGTTACAGTGAAGCCAGTCCCAAGATAATTGTTCTGTACCCCTATTCTC
TAAGAAGCTAAATTGTGTTAGACTGAAACCCATAAGGAACCATTGTTCAAAGTTGGCTTG
[T,C]
TCAAAAGTAAAGATTTTTAATAGTTTCTCTTAATTAGATTATTTTCTAAGACATAGAATT
ATGATTACTATTTTATCTCTATAATTTTCATCTCTATAACGTTTACAAATACTGAAATAA
CCTTTGGAAAAAATTGGCTTTTAGCTTTACTTTTGCAATATTTTATTTTATCCCCATAAA
AGCCTAGGAAATTGGTACTATGACTTTTAGTATGTTCATTTAATAGATGAAAACACAGAA
ACTCAAAGATGTTAAATATGGTGGCCAAGTTCACAAAGCTGATCATTAACAACAACAGGG

15861   GGTGTGGTTGAATAGTTGTCTCTACTGTATTCCAAATAGCAGCCAATGAGGCTGTTACAG
TGAAGCCAGTCCCAAGATAATTGTTCTGTACCCCTATTCTCTAAGAAGCTAAATTGTGTT
AGACTGAAACCCATAAGGAACCATTGTTCAAAGTTGGCTTGTTCAAAAGTAAAGATTTTT
AATAGTTTCTCTTAATTAGATTATTTTCTAAGACATAGAATTATGATTACTATTTTATCT
CTATAATTTTCATCTCTATAACGTTTACAAATACTGAAATAACCTTTGGAAAAAATTGGC
[T,C]
TTTAGCTTTACTTTTGCAATATTTTATTTTATCCCCATAAAAGCCTAGGAAATTGGTACT
ATGACTTTTAGTATGTTCATTTAATAGATGAAAACACAGAAACTCAAAGATGTTAAATAT
GGTGGCCAAGTTCACAAAGCTGATCATTAACAACAACAGGGCCTGAACTCCTGGTTTTCT
GATTTAATCTGTGACAGTGCACCTGGGTGCGCATGCATGCATCACCCCCACACTTGCACA
TAGAACCTTTCCTAGTTGGCTTTGCTCCATGATGACCATTACTGTTCCTTCTACTTCAAA

FIG. 3-26

16264 CTCAAAGATGTTAAATATGGTGGCCAAGTTCACAAAGCTGATCATTAACAACAACAGGGC
CTGAACTCCTGGTTTTCTGATTTAATCTGTGACAGTGCACCTGGGTGCGCATGCATGCAT
CACCCCCACACTTGCACATAGAACCTTTCCTAGTTGGCTTTGCTCCATGATGACCATTAC
TGTTCCTTCTACTTCAAAATAAGCAAATTATCCTACAGATTCAGAGCTGGTACAGGTGTG
CTGTCAAGCAGCCCATTCCATTAGTCAGCTTGTGGTTCACTCACATTAAAGTATTGACCT
[A,T]
AATGGTATATTTATCTAGATAATTCTACCTTGTTATTTTCAAAGCCCCAGTCTTGTTTGC
TAATTCTGTGCATCATTTTTCTCTGATTCTGAAAGGCAAAATTTTGTTGGGCAATTGCTG
TAATATGAGTTTTATCTCCTTTAGAGTCGAATGGATGTGTATATGTCACATGCTCCCACT
GGTTCATCAGTACACAACATTCTGCATATAAAACAGGTAGAGTCTTAGTCATGGAAAACC
ATTCCAATCCTTATTTTCAATATATTTAAAAAGACAGAATTGACCCTGTTAACAGGCCTA

16314 ACAACAGGGCCTGAACTCCTGGTTTTCTGATTTAATCTGTGACAGTGCACCTGGGTGCGC
ATGCATGCATCACCCCCACACTTGCACATAGAACCTTTCCTAGTTGGCTTTGCTCCATGA
TGACCATTACTGTTCCTTCTACTTCAAAATAAGCAAATTATCCTACAGATTCAGAGCTGG
TACAGGTGTGCTGTCAAGCAGCCCATTCCATTAGTCAGCTTGTGGTTCACTCACATTAAA
GTATTGACCTAAATGGTATATTTATCTAGATAATTCTACCTTGTTATTTTCAAAGCCCCA
[G,A]
TCTTGTTTGCTAATTCTGTGCATCATTTTTCTCTGATTCTGAAAGGCAAAATTTTGTTGG
GCAATTGCTGTAATATGAGTTTTATCTCCTTTAGAGTCGAATGGATGTGTATATGTCACA
TGCTCCCACTGGTTCATCAGTACACAACATTCTGCATATAAAACAGGTAGAGTCTTAGTC
ATGGAAAACCATTCCAATCCTTATTTTCAATATATTTAAAAAGACAGAATTGACCCTGTT
AACAGGCCTACCCTAAGAATCTTAAGAGCTTGCTTCCAGTTTGTCCTTGCTGCCTTCTGT

16877 TAAGAGCTTGCTTCCAGTTTGTCCTTGCTGCCTTCTGTATGCCTTGATTTCCCTGGAATT
TAAGAGAAAGGATGTTATGGTACAGACCAAGTAGATGACATAAATGAACACCACCTTAAA
TCAGAGTTTTAAAAATAGGCCCTGAACTGAAGCAAGAGGTAAACTAGGGAAGCCTCAGGA
GAACTGAGACTTCTCCAGAGAGAAGTATCTGGGATTTAACTTCTTTCTAATGAGGCTTGG
TTTTCCATGAACTTTTCCTTTAAACCAAGGGGGGTATTGCTCATCTTTCTGTTGAGCCCC
[A,G]
TTTGTCATAATTGTAAAATGGGTGGTTACATCCTTCTGGTGATCTAGGAGCCCTATTTTC
GTCCTAGCATACAGCATTTTTCTAAAATTTGCTGTTAGCTTTCATGATTCTTACCCTAAC
TATTCTTTTTCTAAAAAACATTTGTTTCAGCTTTACCACTCTGATGAATTCAGAGCTTAT
GACTGGGGAAATGACGCTGATAATATGAAACATTACAATCAGGTGAGCTATTTACAGTAA
CCCCAGCATGCTGATTTTGATAAATTATAATAAAAAATTATTTGAGGGTGGAAAGACTCC

16966 AGTAGATGACATAAATGAACACCACCTTAAATCAGAGTTTTAAAAATAGGCCCTGAACTG
AAGCAAGAGGTAAACTAGGGAAGCCTCAGGAGAACTGAGACTTCTCCAGAGAGAAGTATC
TGGGATTTAACTTCTTTCTAATGAGGCTTGGTTTTCCATGAACTTTTCCTTTAAACCAAG
GGGGGTATTGCTCATCTTTCTGTTGAGCCCCATTTGTCATAATTGTAAAATGGGTGGTTA
CATCCTTCTGGTGATCTAGGAGCCCTATTTTCGTCCTAGCATACAGCATTTTTCTAAAAT
[T,G]
TGCTGTTAGCTTTCATGATTCTTACCCTAACTATTCTTTTTCTAAAAAACATTTGTTTCA
GCTTTACCACTCTGATGAATTCAGAGCTTATGACTGGGGAAATGACGCTGATAATATGAA
ACATTACAATCAGGTGAGCTATTTACAGTAACCCCAGCATGCTGATTTTGATAAATTATA

FIG. 3-27

ATAAAAAATTATTTGAGGGTGGAAAGACTCCTACCTGTCATTTGGTGGCATTTATACTGA
TAGAACTTTTTTTTAAAAAAATTTTAATTTTAATTTTAATTTATTTCAGAAAATTTATAA

17147   GGGGTATTGCTCATCTTTCTGTTGAGCCCCATTTGTCATAATTGTAAAATGGGTGGTTAC
ATCCTTCTGGTGATCTAGGAGCCCTATTTTCGTCCTAGCATACAGCATTTTTCTAAAATT
TGCTGTTAGCTTTCATGATTCTTACCCTAACTATTCTTTTTCTAAAAAACATTTGTTTCA
GCTTTACCACTCTGATGAATTCAGAGCTTATGACTGGGGAAATGACGCTGATAATATGAA
ACATTACAATCAGGTGAGCTATTTACAGTAACCCCAGCATGCTGATTTTGATAAATTATA
[A,G]
TAAAAAATTATTTGAGGGTGGAAAGACTCCTACCTGTCATTTGGTGGCATTTATACTGAT
AGAACTTTTTTTTAAAAAAATTTTAATTTTAATTTTAATTTATTTCAGAAAATTTATAAA
TTAAAGAAGCATATACAAAGAAACTTACATCATGTGTAATCCTTCCATCCAGAGATAACT
AGATGTACTAACATTTTGGTGTATTTATTCCAATTTTCTCAGTATTATATTGCTTTTAGA
CAACTTTTAATCTTTCTATTTTACTTAAGCTATAGTAAGAGATAACTAATATAACTGAGG

17219   ATCTAGGAGCCCTATTTTCGTCCTAGCATACAGCATTTTTCTAAAATTTGCTGTTAGCTT
TCATGATTCTTACCCTAACTATTCTTTTTCTAAAAAACATTTGTTTCAGCTTTACCACTC
TGATGAATTCAGAGCTTATGACTGGGGAAATGACGCTGATAATATGAAACATTACAATCA
GGTGAGCTATTTACAGTAACCCCAGCATGCTGATTTTGATAAATTATAATAAAAAATTAT
TTGAGGGTGGAAAGACTCCTACCTGTCATTTGGTGGCATTTATACTGATAGAACTTTTTT
[T,C]
TAAAAAATTTTAATTTTAATTTTAATTTATTTCAGAAAATTTATAAATTAAAGAAGCAT
ATACAAAGAAACTTACATCATGTGTAATCCTTCCATCCAGAGATAACTAGATGTACTAAC
ATTTTGGTGTATTTATTCCAATTTTCTCAGTATTATATTGCTTTTAGACAACTTTTAATC
TTTCTATTTTACTTAAGCTATAGTAAGAGATAACTAATATAACTGAGGGATTTTTAAATG
CATTTTTAATGGCTACATAATAGAAATTATTTCATAAAAATCTTTACAGCATAAATGAAT

18628   AAAATGAAACAAAATCAACACGCACATTCAAGATCATTATGGTCAAGTACTAAAGTATGT
GAGAGTGTTAATGTCCTTAGAATTTGGCCACAGTTAGCTGGTCCTACTCTGCTCCAAGCC
GGTCCTATTTTGTGAATTAATCTCATTTGATGCCAATTTTTATTACATTCTCTCCAAAAA
ACTAGTCTCAACAGTTTGCTCTCTCCTCAAGTTCACAGCATTATCTCTGCTATATCTATA
TTTTATTGAGTATAAGAGAATTAACCCATGTAAGCTCCATGAGGGTAGGGATTTCTCATC
[A,G]
TTTTGTTCACCAGTGTTTTCTCATCTTGAAGAGTACATGACAATTACTGGGCTCCCAGTA
TCTATGTGTTGCATTAATGAAATTTCTTAACTTTAATCTACCTCAAAATGTCTCTATCTT
CTTGATTCTCTCCTTCCTTTCTCTATCAGAAAATGATGGTCCTCTTATTTTCCAAGTTAT
TCCGGTCCTGTGCCCTTGATCCCATCTCTTCTCACTTCCCCTTCCTTCCTGCCTCCATTC
TCCTGTCCCTTATGAAAAACAAGCAAGACCATCAATTCTATCAAGTTATCATTATGTCAC

18655   TCAAGATCATTATGGTCAAGTACTAAAGTATGTGAGAGTGTTAATGTCCTTAGAATTTGG
CCACAGTTAGCTGGTCCTACTCTGCTCCAAGCCGGTCCTATTTTGTGAATTAATCTCATT
TGATGCCAATTTTTATTACATTCTCTCCAAAAAACTAGTCTCAACAGTTTGCTCTCTCCT
CAAGTTCACAGCATTATCTCTGCTATATCTATATTTTATTGAGTATAAGAGAATTAACCC
ATGTAAGCTCCATGAGGGTAGGGATTTCTCATCGTTTTGTTCACCAGTGTTTTCTCATCT
[T,G]

FIG. 3-28

```
       GAAGAGTACATGACAATTACTGGGCTCCCAGTATCTATGTGTTGCATTAATGAAATTTCT
       TAACTTTAATCTACCTCAAAATGTCTCTATCTTCTTGATTCTCTCCTTCCTTTCTCTATC
       AGAAAATGATGGTCCTCTTATTTTCCAAGTTATTCCGGTCCTGTGCCCTTGATCCCATCT
       CTTCTCACTTCCCCTTCCTTCCTGCCTCCATTCTCCTGTCCCTTATGAAAAACAAGCAAG
       ACCATCAATTCTATCAAGTTATCATTATGTCACTCTGTTCTTATCAACATATTTTTAGTA

18984  CAGTATCTATGTGTTGCATTAATGAAATTTCTTAACTTTAATCTACCTCAAAATGTCTCT
       ATCTTCTTGATTCTCTCCTTCCTTTCTCTATCAGAAAATGATGGTCCTCTTATTTTCCAA
       GTTATTCCGGTCCTGTGCCCTTGATCCCATCTCTTCTCACTTCCCCTTCCTTCCTGCCTC
       CATTCTCCTGTCCCTTATGAAAAACAAGCAAGACCATCAATTCTATCAAGTTATCATTAT
       GTCACTCTGTTCTTATCAACATATTTTTAGTATTGAAGAGGGCTTCTTCTACTTACTCCT
       [G,T]
       AACCTTGTACAATGTAGTTTAGGTCTTCATCTTTTTATCATAGCTACCTTATTTAAAGTC
       ACCCATGGCTTTTAATTGCCAAATTCAATGGCCTATCTTCACCTTTTGAAATGTGTTATG
       TTCGTTACCACAGTCTCCTTGAAACTCAGTCCCCTGACTTGGACTTCCATAACACAATGA
       TTTCTGATTTTCCTTCTGTTTGTGATTGTTCCTTTTGTCCCAGGCACTGGCTACTCCACC
       TTCCACCTCTCTGAAATCATTAGCATTCCCCAAGGATTCTTCAAAACTCTCTTTCTTCCT

19407  CGTTACCACAGTCTCCTTGAAACTCAGTCCCCTGACTTGGACTTCCATAACACAATGATT
       TCTGATTTTCCTTCTGTTTGTGATTGTTCCTTTTGTCCCAGGCACTGGCTACTCCACCTT
       CCACCTCTCTGAAATCATTAGCATTCCCCAAGGATTCTTCAAAACTCTCTTTCTTCCTTG
       GAGAAGTCAGCATAGCTTTAATTTGGACCATTTCTATGGCTTATCTAGATTTTTTCAGGA
       CTTGCCTTCAACCTATTCTTTCTGTAGGTGATTCCATTAACTGTTGCCCATATGGTAGTC
       [C,T]
       GAAGACAGACCTCCGAGAAATGACCCTTGTCTCCAAAACTTCCGCAATATGTCCAAATTT
       CCTAGCCTGACATTCAGACTTTGATTATCTGCCTCCAAGTTTATATCCTATCATATTCCT
       TTATATATTCTGTTCTCCAGGTACACTGGGAAGCTTGCCATTCCTGATCATAGCCTACAA
       ACTCTTCCTGCCTCCCACTCACCCTCATCTCTGCTGTCAAAATGCAACCTTCCCTCAAGA
       GTCATTTCACAGGACCCCTCTTTCTATGAAGCCCTCAGGTGGAAATAATTTTTTGCCTTT

19531  CTCTCTGAAATCATTAGCATTCCCCAAGGATTCTTCAAAACTCTCTTTCTTCCTTGGAGA
       AGTCAGCATAGCTTTAATTTGGACCATTTCTATGGCTTATCTAGATTTTTTCAGGACTTG
       CCTTCAACCTATTCTTTCTGTAGGTGATTCCATTAACTGTTGCCCATATGGTAGTCCGAA
       GACAGACCTCCGAGAAATGACCCTTGTCTCCAAAACTTCCGCAATATGTCCAAATTTCCT
       AGCCTGACATTCAGACTTTGATTATCTGCCTCCAAGTTTATATCCTATCATATTCCTTTA
       [T,C]
       ATATTCTGTTCTCCAGGTACACTGGGAAGCTTGCCATTCCTGATCATAGCCTACAAACTC
       TTCCTGCCTCCCACTCACCCTCATCTCTGCTGTCAAAATGCAACCTTCCCTCAAGAGTCA
       TTTCACAGGACCCCTCTTTCTATGAAGCCCTCAGGTGGAAATAATTTTTTGCCTTTTTTT
       CCATTTTATTTTTGGAGTGTTTATGGCATTTAACATACCTTACTTTGTATACAAATATTT
       GCCTTGCTCCCTCTTTTGCAAATTTCTTAAAGGTAGAGACCATTGTATGTTTTCTTCATA

19911  CTCATCTCTGCTGTCAAAATGCAACCTTCCCTCAAGAGTCATTTCACAGGACCCCTCTTT
       CTATGAAGCCCTCAGGTGGAAATAATTTTTTGCCTTTTTTTTCCATTTTATTTTTGGAGTG
       TTTATGGCATTTAACATACCTTACTTTGTATACAAATATTTGCCTTGCTCCCTCTTTTGC
```

FIG. 3-29

```
        AAATTTCTTAAAGGTAGAGACCATTGTATGTTTTCTTCATATGTTGCTGGTGCCTAACAG
        AACTATGGCCATTGTCCACATTCATTTAGCAGCCTTTGTAGTTATTGCTTTGAGGAGCTT
        [C,T]
        CTCTCATGAATGCCCTTGCTTTCTCTCCCACAGAGTCATCCCCCTATATATGACCTGACT
        GCCATGAAAGTGCCTACTGCTATTTGGGCTGGTGGACATGATGTCCTCGTAACACCCCAG
        GATGTGGCCAGGATACTCCCTCAAATCAAGAGTCTTCATTACTTTAAGCTATTGCCAGAT
        TGGAACCACTTTGATTTTGTCTGGGGCCTCGATGCCCCTCAACGGATGTACAGTGAAATC
        ATAGCTTTAATGAAGGCATATTCCTAAATGCAATGCATTTACTTTTCAATTAAAAGTTGC

20199   TTTGAGGAGCTTCCTCTCATGAATGCCCTTGCTTTCTCTCCCACAGAGTCATCCCCCTAT
        ATATGACCTGACTGCCATGAAAGTGCCTACTGCTATTTGGGCTGGTGGACATGATGTCCT
        CGTAACACCCCAGGATGTGGCCAGGATACTCCCTCAAATCAAGAGTCTTCATTACTTTAA
        GCTATTGCCAGATTGGAACCACTTTGATTTTGTCTGGGGCCTCGATGCCCCTCAACGGAT
        GTACAGTGAAATCATAGCTTTAATGAAGGCATATTCCTAAATGCAATGCATTTACTTTTC
        [A,G]
        ATTAAAAGTTGCTTCCAAGCCCATAAGGGACTTTAGAAAAAATGGTAACCAACAATGAGG
        TTGTCCCCCAGCACCCTGGGGGAGATGCACAGTGGAGTCTGTTTTCCAAGTCAATTGTGT
        TAGTGTTATTTATGTTTAGAGACATCTTTGCATGGGACCATCTACAGGTCCTTATAAACA
        ATGAGGTAGATTAGGCAAAAAGATAAACAAGTTGCTACTCTATCTGGCATTTAAGTCTAA
        TTAAATTGTAATTTTTAGGGCATACCATGAAGTATAGAAATGTCTGAAGCTTCAAAGGAA

20243   AGAGTCATCCCCCTATATATGACCTGACTGCCATGAAAGTGCCTACTGCTATTTGGGCTG
        GTGGACATGATGTCCTCGTAACACCCCAGGATGTGGCCAGGATACTCCCTCAAATCAAGA
        GTCTTCATTACTTTAAGCTATTGCCAGATTGGAACCACTTTGATTTTGTCTGGGGCCTCG
        ATGCCCCTCAACGGATGTACAGTGAAATCATAGCTTTAATGAAGGCATATTCCTAAATGC
        AATGCATTTACTTTTCAATTAAAAGTTGCTTCCAAGCCCATAAGGGACTTTAGAAAAAAT
        [G,A]
        GTAACCAACAATGAGGTTGTCCCCCAGCACCCTGGGGGAGATGCACAGTGGAGTCTGTTT
        TCCAAGTCAATTGTGTTAGTGTTATTTATGTTTAGAGACATCTTTGCATGGGACCATCTA
        CAGGTCCTTATAAACAATGAGGTAGATTAGGCAAAAAGATAAACAAGTTGCTACTCTATC
        TGGCATTTAAGTCTAATTAAATTGTAATTTTTAGGGCATACCATGAAGTATAGAAATGTC
        TGAAGCTTCAAAGGAACAGTGAAATTCCTTTAAGGTCCTATATGGAAACCTCTGTTGTCA

20640   GACATCTTTGCATGGGACCATCTACAGGTCCTTATAAACAATGAGGTAGATTAGGCAAAA
        AGATAAACAAGTTGCTACTCTATCTGGCATTTAAGTCTAATTAAATTGTAATTTTTAGGG
        CATACCATGAAGTATAGAAATGTCTGAAGCTTCAAAGGAACAGTGAAATTCCTTTAAGGT
        CCTATATGGAAACCTCTGTTGTCATTTTATTTATATGGATTGCTATGGCAATGGACAGAG
        TGTGGGATTAGGAGGAGGGCCTGTAACTTCTTTATAAAAGTTTCTTAGCTATCCTGAAGA
        [T,C]
        GTATAGACATTTTTACTTTTTTAGGTATTTTCAACATCAGAAATTCAAAAAAGTCCCCAA
        AGATTCTTCCAGAGAAGCCCTCTTTTCTTACAATCTTATCCCTGGCTATCTGCGTAAACG
        GAATCTTGAACCCATAATAGGATACATGTATAAAATCTTCCTTATTAAAGCAGAAATAAA
        TTGTACAGCATCAATATCATTTTATAATCATAGGGAGGCTTCTTTGTTTAGCATGTAATG
        CCCCCTTTACAGGCTTTTTGTTCTTTGAGGGGTTTGAACATTCCATGAAAAACTGACAGA
```

FIG. 3-30

21156　AGGCTTCTTTGTTTAGCATGTAATGCCCCCTTTACAGGCTTTTTGTTCTTTGAGGGGTTT
GAACATTCCATGAAAAACTGACAGATAGGAAACTGACAATAAAAGATTGAGCTAAAGATG
GAAGCAGAAAGTACTAGGCTAGATAGTCTCTAAACATTAAGTATTTTCTTCCTCCATCTT
AAAAGCAATGAGAAGCCACCAAAATATTTTACCTAATGGAAACCTGATTGCCGCATTTTT
GTAACCACCACTTTGGCTGCTACATAGAGAATGGATTAGAAGATGCCAACAAAAGATTCT
[G,C]
AGCAAGTCTGTAAATCTGATCAAGTGTTCTGATGCAGGCTGATATCCTTCTGTGCTAAGA
GAGATGATCCTTGGAAAATCCAGAGCCAGCTCCATAATACTTTCCTGCTCTGCTGGCAAA
TCCACAAGCTGCTGGCCCCTGGAGCCATTCTTCTCTCAAAACTAGCATTCATCAATTTAA
TGTATACGTATTGATGGGGAATAATGGTCACTATGAAAACCATGTGATAATATGGAAAAA
TACCCATGATATAATGTTATGTGAAGAGAAGAAAATGAAACTGGTAGAACTATGTGATTG

21163　TTTGTTTAGCATGTAATGCCCCCTTTACAGGCTTTTTGTTCTTTGAGGGGTTTGAACATT
CCATGAAAAACTGACAGATAGGAAACTGACAATAAAAGATTGAGCTAAAGATGGAAGCAG
AAAGTACTAGGCTAGATAGTCTCTAAACATTAAGTATTTTCTTCCTCCATCTTAAAAGCA
ATGAGAAGCCACCAAAATATTTTACCTAATGGAAACCTGATTGCCGCATTTTTGTAACCA
CCACTTTGGCTGCTACATAGAGAATGGATTAGAAGATGCCAACAAAAGATTCTGAGCAAG
[A,T]
CTGTAAATCTGATCAAGTGTTCTGATGCAGGCTGATATCCTTCTGTGCTAAGAGAGATGA
TCCTTGGAAAATCCAGAGCCAGCTCCATAATACTTTCCTGCTCTGCTGGCAAATCCACAA
GCTGCTGGCCCCTGGAGCCATTCTTCTCTCAAAACTAGCATTCATCAATTTAATGTATAC
GTATTGATGGGGAATAATGGTCACTATGAAAACCATGTGATAATATGGAAAAATACCCAT
GATATAATGTTATGTGAAGAGAAGAAAATGAAACTGGTAGAACTATGTGATTGCAAATAT

21425　AATGGATTAGAAGATGCCAACAAAAGATTCTGAGCAAGTCTGTAAATCTGATCAAGTGTT
CTGATGCAGGCTGATATCCTTCTGTGCTAAGAGAGATGATCCTTGGAAAATCCAGAGCCA
GCTCCATAATACTTTCCTGCTCTGCTGGCAAATCCACAAGCTGCTGGCCCCTGGAGCCAT
TCTTCTCTCAAAACTAGCATTCATCAATTTAATGTATACGTATTGATGGGAATAATGGT
CACTATGAAAACCATGTGATAATATGGAAAAATACCCATGATATAATGTTATGTGAAGAG
[G,A]
AGAAAATGAAACTGGTAGAACTATGTGATTGCAAATATATACAAATATTAAAACAATTAT
ATGACTTTATAAAATATTTGTATATAATGAAAACTGAAGCAATATAAAAAATAAAATTAG
TTGTGTCAGGGTAGTAACATGATGAGTGATTAATAGTTTTTAATTTTTAATATAGTAATG
ACATAATGTTACAACTTGTCCAAATCTCACAAACATAATATTCAGTAAAGGAAGATAAAC
ATAAAAGAATACATATTTTATTATACATTTTTATGTAGGCTAATTGATGGTTCTGAAAGC

Chromosome map:
Chromosome 10

FIG. 3-31

ISOLATED HUMAN LIPASE PROTEINS, NUCLEIC ACID MOLECULES ENCODING HUMAN LIPASE PROTEINS, AND USES THEREOF

FIELD OF THE INVENTION

The present invention is in the field of lipase proteins that are related to the lysosomal acid lipase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Lipases

The lipases comprise a family of enzymes with the capacity to catalyze hydrolysis of compounds including phospholipids, mono-, di-, and triglycerides, and acyl-coa thioesters. Lipases play important roles in lipid digestion and metabolism. Different lipases are distinguished by their substrate specificity, tissue distribution and subcellular localization.

Lipases have an important role in digestion. Triglycerides make up the predominant type of lipid in the human diet. Prior to absorption in the small intestine, triglycerides are broken down to monoglycerides and free fatty acids to allow solubilization and emulsification before micelle formation in conjunction with bile acids and phospholipids secreted by the liver. Secreted lipases that act within the lumen include lingual, gastric and pancreatic lipases, each having the ability to act under appropriate pH conditions. Modulating the activity of these enzymes has the potential to alter the processing and absorption of dietary fats. This may be important in the treatment of obesity or malabsorption syndromes such as those that occur in the presence of pancreatic insufficiency.

Lipases have an important role in lipid transport and lipoprotein metabolism. Subsequent to absorption across the intestinal mucosa, fatty acids are transported in complexes with cholesterol and protein molecules termed apoliporoteins. These complexes include particles known as chylomicrons, very low density lipoproteins ("VLDLs"), low density lipoproteins ("LDLs") and high density lipoproteins ("HDLs") depending upon their particular forms. Lipoprotein lipase and hepatic lipase are bound to act at the endothelial surfaces of extrahepatic and hepatic tissues, respectively. Deficiencies of these enzymes are associated with pathological levels of circulating lipoprotein particles. Lipoprotein lipase functions as a homodimer and has the dual functions of triglyceride hydrolase and ligand/bridging factor for receptor-mediated lipoprotein uptake. Severe mutations that cause LPL deficiency result in type I hyperlipoproteinemia, while less extreme mutations in LPL are linked to many disorders of lipoprotein metabolism.

Lipases have an important role in lipolysis. Free fatty acids derived from adipose tissue triglycerides are the most important fuel in mammals, providing more than half the caloric needs during fasting. The enzyme hormone-sensitive lipase plays a vital role in the mobilization of free fatty acids from adipose tissue by controlling the rate of lipolysis of stored triglycerides. Hormone sensitive lipase is activated by catecholamines through cyclic AMP-mediated phosphorylation of serine-563. Dephosphorylation is induced by insulin. While mice with homozygous-null mutations of their hormone-sensitive lipase genes induced by homologous recombination have been shown to enlarged adipocytes in their brown adipose tissue and to a lesser extent their white adipose tissue, they are not obese. White adipose tissue from homozygous null mice retain 40% of their wild type triacylglycerol lipase activity suggesting that one or more other, as yet uncharacterized, enzymes also mediate the hydrolysis of triglycerides stored in adipocytes. Hormone-sensitive lipase does not show sequence homology to the other characterized mammalian lipase proteins.

The present invention has substantial similarity to lysosomal acid lipase. Human lysosomal acid lipase/cholesteryl ester hydrolase (EC 3.1.1.13) reveals that it is structurally related to enteric acid lipases, but lacks significant homology with any characterized neutral lipases.

The lysosomal enzyme catalyzes the deacylation of triacylglyceryl and cholesteryl ester core lipids of endocytosed low density lipoproteins; this activity is deficient in patients with Wolman disease and cholesteryl ester storage disease.

Its amino acid sequence, as deduced from the 2.6-kilobase cDNA nucleotide sequence, is 58 and 57% identical to those of human gastric lipase and rat lingual lipase, respectively, both of which are involved in the preduodenal breakdown of ingested triglycerides. Notable differences in the primary structure of the lysosomal lipase that may account for discrete catalytic and transport properties include the presence of 3 new cysteine residues, in addition to the 3 that are conserved in this lipase gene family, and of two additional potential N-linked glycosylation sites.

Two major disorders, the severe infantile-onset Wolman disease and the milder late-onset cholesteryl ester storage disease (CESD), are seemingly caused by mutations in different parts of the lysosomal acid lipase (LIPA) gene.

Burton and Reed (1981) demonstrated material crossreacting with antibodies to acid lipase in fibroblasts of 3 patients with Wolman disease and 3 with cholesterol ester storage disease. Quantitation of the CRM showed normal levels in both cell types. Enzyme activity was reduced about 200-fold in Wolman disease fibroblasts and 50- to 100-fold in cholesterol ester storage disease cells. The allelic nature of Wolman and cholesteryl ester storage diseases is the occurrence of possible genetic compounds, i.e., cases of intermediate severity (Schmitz and Assmann, 1989). In both Wolman disease and cholesteryl ester storage disease, Chatterjee et al. (1986) demonstrated that renal tubular cells shed in the urine are laden with cholesteryl esters and triacylglycerol and that LIPA is lacking in these cells. Yoshida and Kuriyama (1990) described lysosomal acid lipase deficiency in rats.

Aslanidis et al. (1994) summarized the exon structure of the LIPA gene, which consists of 10 exons, together with the sizes of genomic EcoRI and SacI fragments hybridizing to each exon. The DNA sequence of the putative promoter region was presented. Anderson et al. (1994) isolated and sequenced the gene for LIPA. They found that it is spread over 36 kb of genomic DNA. The 5-prime flanking region is GC-rich and has characteristics of a 'housekeeping' gene promoter.

Du et al. (1998) produced a mouse model of lysosomal acid lipase deficiency by a null mutation produced by targeting disruption of the mouse gene. Homozygous knockout mice produced no Lipl mRNA, protein, or enzyme activity. The homozygous deficient mice were born in mendelian ratios, were normal appearing at birth, and followed normal development into adulthood. However, massive accumulation of triglycerides and cholesteryl esters occurred in several organs. By 21 days, the liver developed a yellow-orange color and was up to 2 times larger than normal. The accumulated cholesteryl esters and triglycerides were approximately 30-fold greater than normal. The heterozygous mice had approximately 50% of normal enzyme activity and did not show lipid accumulation. Male and female homozygous deficient mice were fertile and could be bred to produce progeny. This mouse model is the phenotypic model of human CESD and a biochemical and histopathologic mimic of human Wolman disease.

For a review related to lysosomal acid lipase, see Anderson et al., Proc. Nat. Acad. Sci. 91: 2718–2722, 1994; Anderson et al., Genomics 15: 245–247, 1993; Anderson et al., J. Biol. Chem. 266: 22479–22484, 1991; Aslanidis et al., Genomics 20: 329–331, 1994; Aslanidis et al., Genomics 33: 85–93, 1996; Assmann et al., In: Stanbury, J. B.; Wyngaarden, J. B.; Fredrickson, D. S.; Goldstein, J. L.; Brown, M. S.: Metabolic Basis of Inherited Disease. New York: McGraw-Hill (pub.) (5th ed.) 1983. Pp. 803–819; Beaudet et al., J. Pediat. 90: 910–914, 1977; Besley et al., Clin. Genet. 26: 195–203, 1984; Burton et al., Am. J. Hum. Genet. 33: 203–208, 1981; Byrd et al., Acta Neuropath. 45: 37–42, 1979; Cagle et al., Am. J. Med. Genet. 24: 711–722, 1986; Chatterjee et al., Clin. Genet. 29: 360–368, 1986; Christomanou et al., Hum. Genet. 57: 440–441, 1981; Coates et al., Am. J. Med. Genet. 2: 397–407, 1978; Crocker et al., Pediatrics 35: 627–640, 1965; Desai et al., Am. J. Med. Genet. 26: 689–698, 1987; Di Bisceglie et al., Hepatology 11: 764–772, 1990; Du et al., Hum. Molec. Genet. 7: 1347–1354, 1998; Fujiyama et al., Hum. Mutat. 8: 377–380, 1996; Hoeg et al., Am. J. Hum. Genet. 36: 1190–1203, 1984; Kahana et al., Pediatrics 42: 70–76, 1968; Klima et al., J. Clin. Invest. 92: 2713–2718, 1993; Koch et al., Somat. Cell Genet. 7: 345–358, 1981; Koch et al., Cell Genet. 25: 174, 1979; Konno et al., Tohoku J. Exp. Med. 90: 375–389, 1966; Lake et al., J. Clin. Path. 24: 617–620, 1971; Lake et al., J. Pediat. 76: 262–266, 1970; Lough et al., Arch. Path. 89: 103–110, 1970; Marshall et al., Arch. Dis. Child. 44: 331–341, 1969; Maslen et al., Am. J. Hum. Genet. 53 (suppl.): A926, 1993; Muntoni et al., Hum. Genet. 95: 491–494, 1995; Muntoni et al., Hum. Genet. 97: 265–267, 1996; Pagani et al., Hum. Molec. Genet. 5: 1611–1617, 1996; Patrick et al., Nature 222: 1067–1068, 1969; Roytta et al., Clin. Genet. 42: 1–7, 1992; Schaub et al., Europ. J. Pediat. 135: 45–53, 1980; Schiff et al., Clinical aspects. Am. J. Med. 44: 538–546, 1968; Schmitz et al., The Metabolic Basis of Inherited Disease. New York: McGraw-Hill (pub.) (6th ed.) 1989. Pp. 1623–1644; Sloan et al., J. Clin. Invest. 51: 1923–1926, 1972; Spiegel-Adolf et al., Confin. Neurol. 28: 399–406, 1966; Wolman et al., Pediatrics 28: 742–757, 1961; Yokoyama et al., J. Inherit. Metab. Dis. 15: 291–292, 1992; Yoshida et al., Lab. Animal Sci. 40: 486–489, 1990; Young et al., Arch. Dis. Child. 45: 664–668, 1970.

As identified above and in the cited references, lipase proteins are a major target for drug action and development. Accordingly, it is valuable to the field of pharmaceutical development to identify and characterize previously unknown members of the lipase family of proteins. The present invention advances the state of the art by providing previously unidentified human proteins that have homology to known members of the lipase family of proteins.

Lipase proteins, particularly members of the lysosomal acid lipase subfamily, are a major target for drug action and development. Accordingly, it is valuable to the field of pharmaceutical development to identify and characterize previously unknown members of this subfamily of lipase proteins. The present invention advances the state of the art by providing a previously unidentified human lipase proteins that have homology to members of the lysosomal acid lipase subfamily.

SUMMARY OF THE INVENTION

The present invention is based in part on the identification of amino acid sequences of human lipase peptides and proteins that are related to the lysosomal acid lipase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate lipase activity in cells and tissues that express the lipase. Experimental data as provided in FIG. 1 indicates expression in the normal stomach and human leukocyte.

DESCRIPTION OF THE FIGURE SHEETS

FIG. 1 provides the nucleotide sequence of a cDNA molecule sequence that encodes the lipase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the normal stomach and human leukocyte.

FIG. 2 provides the predicted amino acid sequence of the lipase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the lipase protein of the present invention. (SEQ ID NO:3) In addition structure and functional information, such as intron/exon structure, promoter location, etc., is provided where available, allowing one to readily determine specific uses of inventions based on this molecular sequence. 72 SNPs, including 6 indels, have been identified in the gene encoding the transporter protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a lipase protein or part of a lipase protein and are related to the lysosomal acid lipase subfamily. Utilizing these sequences, additional genomic sequences were assembled and transcript and/or cDNA sequences were isolated and characterized. Based on this analysis, the present invention provides amino acid sequences of human lipase peptides and proteins that are related to the lysosomal acid lipase subfamily, nucleic acid sequences in the form of transcript sequences, cDNA sequences and/or genomic sequences that encode these lipase peptides and proteins, nucleic acid variation (allelic information), tissue distribution of expression, and information about the closest art known protein/peptide/domain that has structural or sequence homology to the lipase of the present invention.

In addition to being previously unknown, the peptides that are provided in the present invention are selected based on their ability to be used for the development of commercially important products and services. Specifically, the present peptides are selected based on homology and/or structural relatedness to known lipase proteins of the lysosomal acid lipase subfamily and the expression pattern observed. Experimental data as provided in FIG. 1 indicates expression in the normal stomach and human leukocyte. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known lysosomal acid lipase family or subfamily of lipase proteins.

Specific Embodiments

Peptide Molecules

The present invention provides nucleic acid sequences that encode protein molecules that have been identified as being members of the lipase family of proteins and are related to the lysosomal acid lipase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the lipase peptides of the present invention, lipase peptides, or peptides/proteins of the present invention.

The present invention provides isolated peptide and protein molecules that consist of, consist essentially of, or comprise the amino acid sequences of the lipase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the lipase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated lipase peptide can be purified from cells that naturally express it, purified from cells that have been altered to express it (recombinant), or synthesized using known protein synthesis methods. Experimental data as provided in FIG. 1 indicates expression in the normal stomach and human leukocyte. For example, a nucleic acid molecule encoding the lipase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the lipase peptides of the present invention are the naturally occurring mature proteins. A brief description of how various types of these proteins can be made/isolated is provided below.

The lipase peptides of the present invention can be attached to heterologous sequences to form chimeric or fusion proteins. Such chimeric and fusion proteins comprise a lipase peptide operatively linked to a heterologous protein having an amino acid sequence not substantially homologous to the lipase peptide. "Operatively linked" indicates that the lipase peptide and the heterologous protein are fused in-frame. The heterologous protein can be fused to the N-terminus or C-terminus of the lipase peptide.

In some uses, the fusion protein does not affect the activity of the lipase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant lipase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A lipase peptide-encoding nucleic acid can be cloned into such an expression vector such that the fusion moiety is linked in-frame to the lipase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the lipase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, el al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the lipase peptides of the present invention as well as being encoded by the same genetic locus as the lipase peptide provided herein. As indicated by the data presented in FIG. 3, the map position was determined to be on chromosome 10 by ePCR.

Allelic variants of a lipase peptide can readily be identified as being a human protein having a high degree (significant) of sequence homology/identity to at least a portion of the lipase peptide as well as being encoded by the same genetic locus as the lipase peptide provided herein. Genetic locus can readily be determined based on the genomic information provided in FIG. 3, such as the genomic sequence mapped to the reference human. As indicated by the data presented in FIG. 3, the map position was determined to be on chromosome 10 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a lipase peptide encoding nucleic acid molecule under stringent conditions as more fully described below.

FIG. 3 provides information on SNPs that have been identified in a gene encoding the transporter protein of the present invention. 72 SNP variants were found, including 6 indels (indicated by a "-"). SNPs, identified at different nucleotide positions in introns and regions 5' and 3' of the ORF, may affect control/regulatory elements.

Paralogs of a lipase peptide can readily be identified as having some degree of significant sequence homology/identity to at least a portion of the lipase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a lipase peptide encoding nucleic acid molecule under moderate to stringent conditions as more fully described below.

Orthologs of a lipase peptide can readily be identified as having some degree of significant sequence homology/identity to at least a portion of the lipase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a lipase peptide encoding nucleic acid molecule under moderate to stringent conditions, as more fully described below, depending on the degree of relatedness of the two organisms yielding the proteins.

Non-naturally occurring variants of the lipase peptides of the present invention can readily be generated using recombinant techniques. Such variants include, but are not limited to deletions, additions and substitutions in the amino acid sequence of the lipase peptide. For example, one class of substitutions are conserved amino acid substitution. Such substitutions are those that substitute a given amino acid in a lipase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant lipase peptides can be fully functional or can lack function in one or more activities, e.g. ability to bind substrate, ability to hydrolyze substrate, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as lipase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the lipase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a lipase peptide. Such fragments can be chosen based on the ability to retain one or more of the biological activities of the lipase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the lipase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in lipase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the lipase peptides of the present invention also encompass derivatives or analogs in which a substituted amino acid residue is not one encoded by the genetic code, in which a substituent group is included, in which the mature lipase peptide is fused with another compound, such as a compound to increase the half-life of the lipase peptide (for example, polyethylene glycol), or in which the additional amino acids are fused to the mature lipase peptide, such as a leader or secretory sequence or a sequence for purification of the mature lipase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a lipase-effector protein interaction or lipase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kinmmel eds., 1987.

The potential uses of the peptides of the present invention are based primarily on the source of the protein as well as the class/action of the protein. For example, lipases isolated from humans and their human/mammalian orthologs serve as targets for identifying agents for use in mammalian therapeutic applications, e.g. a human drug, particularly in modulating a biological or pathological response in a cell or tissue that expresses the lipase. Experimental data as provided in FIG. 1 indicates that lipase proteins of the present invention are expressed in normal stomach detected by a virtual northern blot. In addition, PCR-based tissue screening panel indicates expression in human leukocyte. A large percentage of pharmaceutical agents are being developed that modulate the activity of lipase proteins, particularly members of the lysosomal acid lipase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the normal stomach and human leukocyte. Such uses can readily be determined using the information provided herein, that which is known in the art, and routine experimentation.

The proteins of the present invention (including variants and fragments that may have been disclosed prior to the present invention) are useful for biological assays related to lipases that are related to members of the lysosomal acid lipase subfamily. Such assays involve any of the known lipase functions or activities or properties useful for diagnosis and treatment of lipase-related conditions that are specific for the subfamily of lipases that the one of the present invention belongs to, particularly in cells and tissues that express the lipase. Experimental data as provided in FIG. 1 indicates that lipase proteins of the present invention are expressed in normal stomach detected by a virtual northern blot. In addition, PCR-based tissue screening panel indicates expression in human leukocyte.

The proteins of the present invention are also useful in drug screening assays, in cell-based or cell-free systems. Cell-based systems can be native, i.e., cells that normally express the lipase, as a biopsy or expanded in cell culture. Experimental data as provided in FIG. 1 indicates expression in the normal stomach and human leukocyte. In an alternate embodiment, cell-based assays involve recombinant host cells expressing the lipase protein.

The polypeptides can be used to identify compounds that modulate lipase activity of the protein in its natural state or an altered form that causes a specific disease or pathology associated with the lipase. Both the lipases of the present invention and appropriate variants and fragments can be used in high-throughput screens to assay candidate compounds for the ability to bind to the lipase. These compounds can be further screened against a functional lipase to determine the effect of the compound on the lipase activity. Further, these compounds can be tested in animal or invertebrate systems to determine activity/effectiveness. Compounds can be identified that activate (agonist) or inactivate (antagonist) the lipase to a desired degree.

Further, the proteins of the present invention can be used to screen a compound for the ability to stimulate or inhibit interaction between the lipase protein and a molecule that normally interacts with the lipase protein, e.g. a substrate. Such assays typically include the steps of combining the lipase protein with a candidate compound under conditions that allow the lipase protein, or fragment, to interact with the target molecule, and to detect the formation of a complex between the protein and the target or to detect the biochemical consequence of the interaction with the lipase protein and the target, such as any of the associated effects of hydrolysis.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant lipases or appropriate fragments containing mutations that affect lipase function and thus compete for substrate. Accordingly, a fragment that competes for substrate, for example with a higher affinity, or a fragment that binds substrate but does not allow release, is encompassed by the invention.

Any of the biological or biochemical functions mediated by the lipase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the lipase can be assayed. Experimental data as provided in FIG. 1 indicates that lipase proteins of the present invention are expressed in normal stomach detected by a virtual northern blot. In addition, PCR-based tissue screening panel indicates expression in human leukocyte.

Binding and/or activating compounds can also be screened by using chimeric lipase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native lipase. Accordingly, a different set of signal transduction components is available as an end-point assay for activation. This allows for assays to be performed in other than the specific host cell from which the lipase is derived.

The proteins of the present invention are also useful in competition binding assays in methods designed to discover compounds that interact with the lipase (e.g. binding partners and/or ligands). Thus, a compound is exposed to a lipase polypeptide under conditions that allow the compound to bind or to otherwise interact with the polypeptide. Soluble lipase polypeptide is also added to the mixture. If the test compound interacts with the soluble lipase polypeptide, it decreases the amount of complex formed or activity from the lipase target. This type of assay is particularly useful in cases in which compounds are sought that interact with specific regions of the lipase. Thus, the soluble polypeptide that competes with the target lipase region is designed to contain peptide sequences corresponding to the region of interest.

To perform cell free drug screening assays, it is sometimes desirable to immobilize either the lipase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of lipase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a lipase-binding protein and a candidate compound are incubated in the lipase protein-presenting wells and the amount of complex trapped in the well can be quantitated. Methods for detecting such complexes, in addition to those described above for the GST-immobilized complexes, include immunodetection of complexes using antibodies reactive with the lipase protein target molecule, or which are reactive with lipase protein and compete with the target molecule, as well as enzyme-linked assays which rely on detecting an enzymatic activity associated with the target molecule.

Agents that modulate one of the lipases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of lipase protein activity identified according to these drug screening assays can be used to treat a subject with a disorder mediated by the lipase pathway, by treating cells or tissues that express the lipase. Experimental data as provided in FIG. 1 indicates expression in the normal stomach and human leukocyte. These methods of treatment include the steps of administering a modulator of lipase activity in a pharmaceutical composition to a subject in need of such treatment, the modulator being identified as described herein.

In yet another aspect of the invention, the lipase proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the lipase and are involved in lipase activity.

The two-hybrid system is based on the modular nature of most transcription factors, which consist of separable DNA-binding and activation domains. Briefly, the assay utilizes two different DNA constructs. In one construct, the gene that codes for a lipase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a lipase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the lipase protein.

This invention further pertains to novel agents identified by the above-described screening assays. Accordingly, it is within the scope of this invention to further use an agent identified as described herein in an appropriate animal model. For example, an agent identified as described herein (e.g., a lipase-modulating agent, an antisense lipase nucleic acid molecule, a lipase-specific antibody, or a lipase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The lipase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the normal stomach and human leukocyte. The method involves contacting a biological sample with a compound capable of interacting with the lipase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered lipase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the lipase protein in which one or more of the lipase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and lipase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the normal stomach and human leukocyte. Accordingly, methods for treatment include the use of the lipase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the lipase proteins. Antibodies can be prepared from any region of the peptide as described herein. However, preferred regions will include those involved in function/activity and/or lipase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that lipase proteins of the present invention are expressed in normal stomach detected by a virtual northern blot. In addition, PCR-based tissue screening panel indicates expression in human leukocyte. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the normal stomach and human leukocyte. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the normal stomach and human leukocyte. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the normal stomach and human leukocyte. Thus, where a specific protein has been correlated with expression in a specific tissue, antibodies that are specific for this protein can be used to identify a tissue type.

The antibodies are also useful for inhibiting protein function, for example, blocking the binding of the lipase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG.

2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a lipase peptide or protein of the present invention (cDNA, transcript and genomic sequence). Such nucleic acid molecules will consist of, consist essentially of, or comprise a nucleotide sequence that encodes one of the lipase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the lipase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof.

The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the lipase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 10 by ePCR.

FIG. 3 provides information on SNPs that have been identified in a gene encoding the transporter protein of the present invention. 72 SNP variants were found, including 6 indels (indicated by a "-"). SNPs, identified at different nucleotide positions in introns and regions 5' and 3' of the ORF, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 72 SNPs, including 6 indels, have been identified in the gene encoding the transporter protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 10 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that lipase proteins of the present invention are expressed in normal stomach detected by a virtual northern blot. In addition, PCR-based tissue screening panel indicates expression in human leukocyte. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in lipase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a lipase protein, such as by measuring a level of a lipase-encoding nucleic acid in a sample of cells from a subject e.g., mRNA or genomic DNA, or determining if a lipase gene has been mutated. Experimental data as provided in FIG. 1 indicates that lipase proteins of the present invention are expressed in normal stomach detected by a virtual northern blot. In addition, PCR-based tissue screening panel indicates expression in human leukocyte.

Nucleic acid expression assays are useful for drug screening to identify compounds that modulate lipase nucleic acid expression.

The invention thus provides a method for identifying a compound that can be used to treat a disorder associated with nucleic acid expression of the lipase gene, particularly biological and pathological processes that are mediated by the lipase in cells and tissues that express it. Experimental data as provided in FIG. 1 indicates expression in the normal stomach and human leukocyte. The method typically includes assaying the ability of the compound to modulate the expression of the lipase nucleic acid and thus identifying a compound that can be used to treat a disorder characterized by undesired lipase nucleic acid expression. The assays can be performed in cell-based and cell-free systems. Cell-based assays include cells naturally expressing the lipase nucleic acid or recombinant cells genetically engineered to express specific nucleic acid sequences.

The assay for lipase nucleic acid expression can involve direct assay of nucleic acid levels, such as mRNA levels. In this embodiment the regulatory regions of these genes can be operably linked to a reporter gene such as luciferase.

Thus, modulators of lipase gene expression can be identified in a method wherein a cell is contacted with a candidate compound and the expression of mRNA determined. The level of expression of lipase mRNA in the presence of the candidate compound is compared to the level of expression of lipase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment with the nucleic acid as a target, using a compound identified through drug screening as a gene modulator to modulate lipase nucleic acid expression in cells and tissues that express the lipase. Experimental data as provided in FIG. 1 indicates that lipase proteins of the present invention are expressed in normal stomach detected by a virtual northern blot. In addition, PCR-based tissue screening panel indicates expression in human leukocyte. Modulation includes both up-regulation (i.e. activation or agonization) or down-regulation (suppression or antagonization) or nucleic acid expression.

Alternatively, a modulator for lipase nucleic acid expression can be a small molecule or drug identified using the screening assays described herein as long as the drug or small molecule inhibits the lipase nucleic acid expression in the cells and tissues that express the protein. Experimental data as provided in FIG. 1 indicates expression in the normal stomach and human leukocyte.

The nucleic acid molecules are also useful for monitoring the effectiveness of modulating compounds on the expression or activity of the lipase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in lipase nucleic acid expression, and particularly in qualitative changes that lead to pathology. The nucleic acid molecules can be used to detect mutations in lipase genes and gene expression products such as mRNA. The nucleic acid molecules can be used as hybridization probes to detect naturally occurring genetic mutations in the lipase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the lipase gene associated with a dysfunction provides a diagnostic tool for an active disease or susceptibility to disease when the disease results from overexpression, underexpression, or altered expression of a lipase protein.

Individuals carrying mutations in the lipase gene can be detected at the nucleic acid level by a variety of techniques. FIG. 3 provides information on SNPs that have been identified in a gene encoding the transporter protein of the present invention. 72 SNP variants were found, including 6 indels (indicated by a "-"). SNPs, identified at different nucleotide positions in introns and regions 5' and 3' of the ORF, may affect control/regulatory elements. As indicated by the data presented in FIG. 3, the map position was determined to be on chromosome 10 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a lipase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant lipase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the lipase gene in an individual in order to select an appropriate compound or dosage regimen for treatment. FIG. 3 provides information on SNPs that have been identified in a gene encoding the transporter protein of the present invention. 72 SNP variants were found, including 6 indels (indicated by a "-"). SNPs, identified at different nucleotide positions in introns and regions 5' and 3' of the ORF, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control lipase gene expression in cells, tissues, and organisms. A DNA antisense nucleic acid molecule is designed to be complementary to a region of the gene involved in transcription, preventing transcription and hence production of lipase protein. An antisense RNA or DNA nucleic acid molecule would hybridize to the mRNA and thus block translation of mRNA into lipase protein.

Alternatively, a class of antisense molecules can be used to inactivate mRNA in order to decrease expression of lipase nucleic acid. Accordingly, these molecules can treat a disorder characterized by abnormal or undesired lipase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the lipase protein, such as substrate binding.

The nucleic acid molecules also provide vectors for gene therapy in patients containing cells that are aberrant in lipase gene expression. Thus, recombinant cells, which include the patient's cells that have been engineered ex vivo and returned to the patient, are introduced into an individual where the cells produce the desired lipase protein to treat the individual.

The invention also encompasses kits for detecting the presence of a lipase nucleic acid in a biological sample. Experimental data as provided in FIG. 1 indicates that lipase proteins of the present invention are expressed in normal stomach detected by a virtual northern blot. In addition, PCR-based tissue screening panel indicates expression in human leukocyte. For example, the kit can comprise reagents such as a labeled or labelable nucleic acid or agent capable of detecting lipase nucleic acid in a biological sample; means for determining the amount of lipase nucleic acid in the sample; and means for comparing the amount of lipase nucleic acid in the sample with a standard. The compound or agent can be packaged in a suitable container. The kit can further comprise instructions for using the kit to detect lipase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the lipase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the lipase gene of the present invention. FIG. 3 provides information on SNPs that have been identified in a gene encoding the transporter protein of the present invention. 72 SNP variants were found, including 6 indels (indicated by a "-"). SNPs, identified at different nucleotide positions in introns and regions 5' and 3' of the ORF, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified lipase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterolipase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed.*, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as lipases, appropriate secretion signals are incorporated into the vector. The signal sequence can be endogenous to the peptides or heterologous to these peptides.

Where the peptide is not secreted into the medium, which is typically the case with lipases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a lipase protein or peptide that can be further purified to produce desired amounts of lipase protein or fragments. Thus, host cells containing expression vectors are useful for peptide production.

Host cells are also useful for conducting cell-based assays involving the lipase protein or lipase protein fragments, such as those described above as well as other formats known in the art. Thus, a recombinant host cell expressing a native lipase protein is useful for assaying compounds that stimulate or inhibit lipase protein function.

Host cells are also useful for identifying lipase protein mutants in which these functions are affected. If the mutants naturally occur and give rise to a pathology, host cells containing the mutations are useful to assay compounds that have a desired effect on the mutant lipase protein (for example, stimulating or inhibiting function) which may not be indicated by their effect on the native lipase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a lipase protein and identifying and evaluating modulators of lipase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the lipase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the lipase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, and lipase protein activation, may not be evident from in vitro cell-free or cell-based assays. Accordingly, it is useful to provide non-human transgenic animals to assay in vivo lipase protein function, including substrate interaction, the effect of specific mutant lipase proteins on lipase protein function and substrate interaction, and the effect of chimeric lipase proteins. It is also possible to assess the effect of null mutations, that is mutations that substantially or completely eliminate one or more lipase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

SEQUENCE LISTING

<160> NUMBER OF SEQ ID NOS: 4

<210> SEQ ID NO 1
<211> LENGTH: 1360
<212> TYPE: DNA
<213> ORGANISM: Human

<400> SEQUENCE: 1

```
ctcttactct tcagcctgat gtcaaaagca aaagttcaga agttcctcat c aataaggag      60
tccttgtgag caggtgaagc tcatctaact aggcatttct atgatgtggc t gcttttaac    120
aacaacttgt ttgatctgtg aactttaaa tgctggtgga ttccttgatt t ggaaaatga    180
agtgaatcct gaggtgtgga tgaatactag tgaaatcatc atctacaatg g ctaccccag    240
tgaagagtat gaagtcacca ctgaagatgg gtatatactc cttgtcaaca g aattcctta    300
tgggcgaaca catgctagga gcacaggtcc ccggccagtt gtgtatatgc a gcatgccct    360
gtttgcagac aatgcctact ggcttgagaa ttatgccaat ggaagccttg g attccttct    420
agcagatgca ggttatgatg tatggatggg aaacagtcgg ggaaacactt g gtcaagaag    480
acacaaaaca ctctcagaga cagatgagaa attctgggcc tttagttttg a tgaaatggc    540
caaatatgat ctcccaggag taatagactt cattgtaaat aaaactggtc a ggagaaatt    600
gtatttcatt ggacattcac ttggcactac aatagggttt gtagcctttt c caccatgcc    660
tgaactggca caaagaatca aaatgaattt tgccttgggg cctacgatct c attcaaata    720
tcccacgggc attttttacca ggttttttct acttccaaat tccataatca a ggctgtttt    780
tggtaccaaa ggtttctttt tagaagataa gaaaacgaag atagcttcta c caaatctg    840
caacaataag atactctggt tgatatgtag cgaatttatg tccttatggg c tggatccaa    900
caagaaaaat atgaatcaga gtcgaatgga tgtgtatatg tcacatgctc c cactggttc    960
atcagtacac aacattctgc atataaaaca gctttaccac tctgatgaat t cagagctta   1020
tgactgggga aatgacgctg ataatatgaa acattacaat cagagtcatc c cctatata   1080
tgacctgact gccatgaaag tgcctactgc tatttgggct ggtggacatg a tgtcctcgg   1140
aacaccccag gatgtggcca ggatactccc tcaaatcaag agtctttcat t agtgctaag   1200
cctattgcca gaatgggaac ccacctttga ttttgtctgg ggccttgatg c ccctcaacg   1260
gatgttcagt ggaaatcata accttttaatg aaggcatatt tcctaaatgc c aatgcattt   1320
tacctttttc aatttaaagg ttggtttcca aagcccttac                            1360
```

<210> SEQ ID NO 2
<211> LENGTH: 395
<212> TYPE: PRT
<213> ORGANISM: Human

<400> SEQUENCE: 2

```
Met Met Trp Leu Leu Leu Thr Thr Thr Cys Leu Ile Cys Gly Thr Leu
 1               5                  10                  15

Asn Ala Gly Gly Phe Leu Asp Leu Glu Asn Glu Val Asn Pro Glu Val
                20                  25                  30

Trp Met Asn Thr Ser Glu Ile Ile Ile Tyr Asn Gly Tyr Pro Ser Glu
            35                  40                  45

Glu Tyr Glu Val Thr Thr Glu Asp Gly Tyr Ile Leu Leu Val Asn Arg
        50                  55                  60

Ile Pro Tyr Gly Arg Thr His Ala Arg Ser Thr Gly Pro Arg Pro Val
```

```
                65                  70                  75                  80
Val Tyr Met Gln His Ala Leu Phe Ala Asp Asn Ala Tyr Trp Leu Glu
                        85                  90                  95
Asn Tyr Ala Asn Gly Ser Leu Gly Phe Leu Ala Asp Ala Gly Tyr
            100                 105                 110
Asp Val Trp Met Gly Asn Ser Arg Gly Asn Thr Trp Ser Arg Arg His
            115                 120                 125
Lys Thr Leu Ser Glu Thr Asp Glu Lys Phe Trp Ala Phe Ser Phe Asp
            130                 135                 140
Glu Met Ala Lys Tyr Asp Leu Pro Gly Val Ile Asp Phe Ile Val Asn
145                 150                 155                 160
Lys Thr Gly Gln Glu Lys Leu Tyr Phe Ile Gly His Ser Leu Gly Thr
                165                 170                 175
Thr Ile Gly Phe Val Ala Phe Ser Thr Met Pro Glu Leu Ala Gln Arg
            180                 185                 190
Ile Lys Met Asn Phe Ala Leu Gly Pro Thr Ile Ser Phe Lys Tyr Pro
        195                 200                 205
Thr Gly Ile Phe Thr Arg Phe Phe Leu Pro Asn Ser Ile Ile Lys
        210                 215                 220
Ala Val Phe Gly Thr Lys Gly Phe Phe Leu Glu Asp Lys Lys Thr Lys
225                 230                 235                 240
Ile Ala Ser Thr Lys Ile Cys Asn Asn Lys Ile Leu Trp Leu Ile Cys
                245                 250                 255
Ser Glu Phe Met Ser Leu Trp Ala Gly Ser Asn Lys Lys Asn Met Asn
                260                 265                 270
Gln Ser Arg Met Asp Val Tyr Met Ser His Ala Pro Thr Gly Ser Ser
            275                 280                 285
Val His Asn Ile Leu His Ile Lys Gln Leu Tyr His Ser Asp Glu Phe
        290                 295                 300
Arg Ala Tyr Asp Trp Gly Asn Asp Ala Asp Asn Met Lys His Tyr Asn
305                 310                 315                 320
Gln Ser His Pro Pro Ile Tyr Asp Leu Thr Ala Met Lys Val Pro Thr
                325                 330                 335
Ala Ile Trp Ala Gly His Asp Val Leu Gly Thr Pro Gln Asp Val
            340                 345                 350
Ala Arg Ile Leu Pro Gln Ile Lys Ser Leu Ser Leu Val Leu Ser Leu
            355                 360                 365
Leu Pro Glu Trp Glu Pro Thr Phe Asp Phe Val Trp Gly Leu Asp Ala
        370                 375                 380
Pro Gln Arg Met Phe Ser Gly Asn His Asn Leu
385                 390                 395

<210> SEQ ID NO 3
<211> LENGTH: 22067
<212> TYPE: DNA
<213> ORGANISM: Human

<400> SEQUENCE: 3
ttatggccta acctttttaa ctttgagtta ttttcaagag aaaatttgaa a aagcagcct        60 ttgaggagaa agaagcaatc caacaaacaa aaagataacc acactgtaat a ggaaatgtg       120 ttttgaatag acattggaa gaaaataat aatcattttt acaggtagat c ccaaagtca        180 aggatctatg ttcaaccatg tgtgttccac catcttcaca attgaatgag t aaccatcat       240 taagcagtta gcttaggccg taatatgatt cttggactga gatttcaaaa a taccacagg      300
```

-continued

```
ccttctgaaa ggttacccct ttctagctcc actatcatct aatttttatta a aaaaaaaaa    360
aaaaggaaaa atttgagctt ctagagagta ggggctacca ttttgtatcc c acagggcca    420
aggaacaagt tttaatgtat tcatttaaat taatttcagt atgagtattg a aatatataa    480
tagaaatatt gtaacattat atattttcta tactttta ttatatagaa a atatatatt     540
acagaatata ttattaaata ttgtagaaca atatataata cagaaaaata t ataatactc    600
agtaatatat taaatactta ttaaaatagc aagcttatat aggaagagtg a tggagcatt    660
gtgagaaagt ttcagcttta tttctttgac attactttgt ttctgcacaa a caaaagaat    720
tacaggaatt gtccagatta ttcaaataac tcgaagttga ggagggaata t aagtcaatg    780
atgtagaaac tcttttaaga tttgagctag cctacaatct gtaaagatct g tgaaattga    840
actatatttg tgctatttcc atattaagtc aaggcaacaa atcaatatta a taataataa    900
catagcactt ctagaacttt ctaaagagtc caataaagtt ttgttagaaa g gattgtttt    960
tgaagttaaa aaccatgaga aattccagga aaatccacat acctatgcca t catactatc   1020
aatcagggca aaacatgctt gagtctttca tcaagactaa atgattaagg a gtggtacat   1080
aacttttccc tgttctgact agctgaacac ttccttttac tccacatttg t ttaattggc   1140
atgaaatttc ccactccact aaaacagatc ttaggatttg gacaacacaa a atatcattt   1200
gttttgaaag gatttgagga taaatccaaa ctaatagaac tgaaacttct a tattatgct   1260
gggtagcaac ttagttttcc ctacccttct tcatgctggg agatgaaaga g attcagtta   1320
cggcttaagc tccacaggca tacaaagtga agcagaaaac tgaggcacgt g tgcctccat   1380
tatctggtat ctcatgtggg gcttagaggt aaattgtcgt tatttggcct c catttctgc   1440
ctttaaccac tggtgtaaac aaaggttact gtgccaaagt tgacagcaac c caaatccct   1500
ttggcatgtg aattagtttc ctctgccata ctgctagttc caaattcctt c tggtttcag   1560
gatttaggag tcagggttgc ctcatcttct caaatgagtt acagtcacgc a catccctac   1620
acactgcatg gttggcacta gttccttgat atatgttact ccgtttgatc c tcatgaagg   1680
atcaaatggg gaagggagat actattgtct ctgattgtcc attaagatct t gagtatgtt   1740
ctacttccct gtttgacaca ctggtttgaa aatgttgcta agtctcccca a caatgacag   1800
atactcagtg gaaacatgaa ggattccgtc aaactggtta ttttgcatca t gtagaccac   1860
tatttcccaa cctgcaagtg catcatggcc tttggtgtgt cagggacacg c cttgggtgt   1920
gtgtctcagt ctaaagcttc ctccttttca caagcttcct gtttctcatc t ctctagctt   1980
ctaactgtca ctgtaatcat ctcttactct tcagcctgat gtcaaaagca a aagttcaga   2040
agttcctcat caataaggag tccttgtgag caggtgaagc tcatctaact a ggtaagatg   2100
aagatctatc ataaccagga ggcaggttgg aaggtgccag ttgcactggc a gtcaggtgc   2160
aagagctctg cagtgaggct gcctgagtgt ccatcctaga tctctcacct c ttggctctg   2220
tgaccttgag caggtcttaa atctctctaa gcctttgttt ttttaattga t aaaatgagg   2280
ataataatag taccaaaatt agggagattt tcagagctta aataacatac g tgaactatt   2340
tagagtaatg cctgccataa ggggactcag tagcttatta ttagtttcat a caatttgaa   2400
aagtttcata atatttgcag ataaagatg atcttcaacc agatagctaa t gtatgcaaa   2460
gctatttagc ttcagaagta aactctgcat ttctagaagt taaatattac t ttgttatag   2520
tgaattatct gtaatattta tctcttgctc acttttataa gaaaaatagt g aaagcattt   2580
attaagaact tacactgcac taaatgttat atatgactta atcctcacta t aaccctatg   2640
```

-continued

```
agataggtta cattattgtc ctaattttac taacaaggaa accaagagac a aagctacta    2700
aaacacttgc ctgaggttag acatcttctt ctgtggtgag gctggatttc a aatttagac    2760
catttgactg tagcacttat atgatgagca tgctgtttag tgttatagtg t tggtctacc    2820
tttgaataga catacttttc aaccatggca aggaagtgag actgcacatt g aaatatgta    2880
aaatttgcct ttgggtgcca cgtgagaaat agtcacatca ctagaaacta a tcataagct    2940
tttgtgtttg gttaaagttt tattgatcca tttttcttgt ttactttgtg g gatactggg    3000
cttaactagg ggatacctcc actttttact tggccatggt atgaaaacct g tcctctgaa    3060
tctttagata ttttggcaaa ttgtaggcaa acaaagactt aaagcaattc a accttgatt    3120
aaaataagac caaaaatgcc tccatacttg attaaattta tttcatttta g gaactggat    3180
tataatcaag acaacttcta catgaaaaaa tagattaata gtgctccaag t tagttcact    3240
gtatttattc cttttatac attatctgcc ttcggtgtta ttcaagtttt c attaatcat    3300
taataatttc actaatcatt ttatttcatt aatcaacatt gatagttaaa a ttaatctgt    3360
gaatattaaa tgttttatgc caggcatttc tatgatgtgg ctgctttaa c aacaacttg     3420
tttgatctgt ggaactttaa atgctggtgg attccttgat ttggaaaatg a agtgaatcc    3480
tgaggtgtgg atgaatactg taagtcatgg aaaactgtga agaacatcaa a taaagcagg    3540
actaatggag tatgaggtta cgaaaggtcc tgttgtaaca gaaaatctct g ataaaacag    3600
ataaaatgta gatggttttt aacctctgca agagtcaagc tagttagatc t ttgtctgaa    3660
aaacaaatac tgtccggtaa tgaaaaccaa attgtgctat tgtgctatct a tctatctat    3720
ctatctatct atctatctat ctatctatct atctatctat ttatctatct a tctatagat    3780
agaacctcct cttttgaatt tatgttttaa gaatatcaag ctatttgttg a tatacatga    3840
ttgccttcta ttgatctata gttctattac ttttaaagca agagggtct c aaaagacaa     3900
ttgacttgat aatatagctt tgtcagaaag aatgggtcaa tgctaaattt t cccccaacc    3960
ccccaaaata ttagccaata gtagatattt tttaaaattc tacttatttt g tattaagac    4020
tttatttatt aattttacag ttacctggtg ctacaaattt cagataattc a ccctaataa    4080
gcacacaaca gatggtttgt tttgattcct ttttatatcc tttggagaag t tccactaac    4140
gactgtattt ttactgggca gagtgaaatc atcatctaca atggctaccc c agtgaagag    4200
tatgaagtca ccactgaaga tgggtatata ctccttgtca acagaattcc t tatgggcga    4260
acacatgcta ggagcacagg tacaagatat gtctctcctg aaaagggggac t gcattgacc    4320
tcctgcttct caggaggaat ttaatgctag atatgcatca acagagttta t caaaattgg    4380
tttgaattat tggattagtc tttaaatagt tatcagggga gctcactctt t gcctgataa    4440
ttctctgaag acagacagga acctaaaaat acaaacagca agactgatct g ctaactgc     4500
aaccagaggt acttgttagg gtgtaaacag aaaggcagag cctgcatttt g tcacctcat    4560
tactgattta tcatgtggaa aattgctttg tcccaggaaa atggatcctc t cattgtcag    4620
aaggagattt tctaggttgt atgaaattga ctctggggca cccaagaaga a cctctcctg    4680
ctcccactaa aattaagggg cctccctctg caggataaaa acaatctag t taaatgaca    4740
acgcatttct gaaaagtttt ccaggactga aaacccttaac atccacatac a ctttgatct    4800
aagggacaga cggttcatag aatgaaagag tatggtgtca ataaggcttg a attctagaa    4860
tgaggagcca gccatgccat agcagggaa tgatactcct taaaaggaa a atttaacta     4920
caaatcctct gaagtagaaa tgataagaat aaccaaaata tctgcaatgg t tcaatagca    4980
aataatttat tggcagctgc ttaccgtgtt cattttgcat ctttttttccc a ccacacata   5040
```

-continued

```
ttaaggagca gctgaagtca tgtttgacat tctctccctc ttttatctcc a gtttcagaa    5100 tgaaaaatga gagtgagata tgagtagttt tactagttaa aatatgaaac a cccagttaa    5160 atttgaaggt cagataaaca acaaataatt ttgtataagt ctcattttaa g ataatacta    5220 aaaagtcatt atttattcac tattatcact atttataaaa ttttgtagag c atcctggat    5280 cttttttgctt acttttgttt ttattttttg ctaaatctgg caatcccagg c acatgtgtg    5340 aaggagctgt gaaatataaa aggagaaaac tttatggga aagatttggc t taaggagag    5400 ataattttgg aaagatttag aattaaagat cattcattag atgtaatgtt c taaatactt    5460 tatatcagtt aaacttctca tcaacaatat gagatgggta ccactaatag t caccatttc    5520 acaaatgatg aaattaaggc acaaccggtt atgttaagag gcctaaagtc c acaaatagc    5580 aagctgacag accagaattt aagcccaggc atgctggctc cagagcctgt g ctcttagtc    5640 attaaattat agtgccttac ttgaccttcc accctggtta ctttggatct c cctgaatgc    5700 tctctctccc tcagaaatac tggaagttgg cagagggaca ctgagctgag c atattattg    5760 tagtttttaa atgctctcca ctggacagaa gatgggggat ttgaatagaa a tttggtgag    5820 gaactaatca gtgtccattt acactcacct cctcttcctc cctggaagag c tataggact    5880 tgagtaagca tgataaattt cgtgtctttg taaaccacac ccaggaaatt t gtatataca    5940 aatacataga gcacagtagt tatcaggaca gactttgaca taaaaagaac t gggtttgag    6000 tccctgctct ggccttctta tctgggtggc cctctgggaa agttacttaa c tacataaag    6060 ttttgtttcc atatctacaa aatgaggttt ctcaaaatag cagctagttt a tagagttgt    6120 tgcaagaatt tagtaagcta atacatataa atacgtcaac atagcaccag g tacaaaaat    6180 atgtgctcaa gaaactgaag ttacctgatt ataatgctct atactattga c aagggaaaa    6240 gtgaaaacag tttttgtttt accatgtgtg tatgtgtgtg tgtctgtgat g tttccgaca    6300 tgctctattt aacataaatt actctcactc tttctctctc tctctttctc t ttctccctc    6360 tctcatctta ccctttcccc caccaggtcc ccggccagtt gtgtatatgc a gcatgccct    6420 gtttgcagac aatgcctact ggcttgagaa ttatgccaat ggaagccttg g attccttct    6480 agcagatgca ggttatgatg tatgatggg aaacagtcgg ggaaacactt g gtcaagaag    6540 acacaaaaca ctctcagaga cagatgagaa attctgggcc tttaggtaaa t attagctaa    6600 gaaaactcaa gggggaaatt ggaggcaatt ttaaaaaaat aacgtggacg c tattaatga    6660 ttatctttga cgcttgaagt catatagctc cttgtagttt ctgttaagat c tcaaaggag    6720 ggtaacagca agaagctctg attttttcact gattctccca caagcaaagt a tggcatttc    6780 aacaagatca ttttacatc caattctgtg aattctatgc attaaaagta t gtccaaaga    6840 gacagctcag gaaattatca tgaccaatgt gcacattcat tcagccaatg t ttactgagt    6900 ggctactgta tgcgctgttc taggccccga acattcaaac agggaacaga c aaactctga    6960 cctcacaaag cttatgttca ttttagtgat aattttacaa gtcattgctc c tggattgcc    7020 aatcaactgt gtaaagatga tttggaccag gaccttattg atttagagaa a ctgtgattg    7080 atttagagaa actgagatcg cacatagtac cattttcagg aaaactccaa t attagattt    7140 ttaaaacctt gttaatgggc aatgaagaag atcttttttt gatatcttgt t tcttttaat    7200 ggaagagttt tctgctgtca ccagaggaca ggctgatgcc tgcgatagac t ttctttct    7260 tcaggcctaa gctccctgtt ggtttgtaaa cctgatgcta aacagactg t gtattccta    7320 ttacattaat aaaacattca gtacccactg aaagtttgag aatagtggag g aatagaata    7380
```

-continued

```
gaatgttata gtctgagttc ttgggcaggg gcaagcatca ggaaatattg a atcattagt    7440
ctttaggagg tgtcacaaca attctcctat tcttgtaagt cccaatctat a gatttcctc    7500
acatgttctt ttaataaaca ggcttctagc ttatggaata cctgatttga c taaatgtta    7560
tataggccct tttgttcctc ctgtctgaag aacaaaatac tagtactatg g aatattggt    7620
atatattaaa tatatatcta tatatccatg tggacaggaa tactactact a acaacatct    7680
tactgagcac ccactggcag ccagagtcgt ttctttcata ctattaaacc c cgttagcag    7740
ccccgtaaac caggtactac cctgtttatt tcccaaatga gaaacatag g ctcagagca    7800
tttcagtaat ttctcaagag ttgcaaaggc cataaatagt agaatcatga t ttacaaaac    7860
ccctgtttcc aaagatgggt attaaatggt cctaacaatt gtgaagcctc a tgtgggagt    7920
cagaagtaga ggcacacaag ccagatgggg aaagggaggg caaagaaaag c aagagaagg    7980
gaaggaagag gagggatcat aaggttgaac ttcaaatatc atacacaagt t tcgaaagtg    8040
ttcctcttat aaggaagtaa atgtacata tgcagaaaaa caaaaagcta c aatagccta    8100
catataattg gataaataat gaaatacaca ttgaatctaa gtaaacagca t agaatctgg    8160
gtgtaaaaaa gaagtgagca agtgctctga gttttaaact taaacttgca a gtatttata    8220
aaagcccctg ttttattttg cagttttgat gaaatggcca aatatgatct c ccaggagta    8280
atagacttca ttgtaaataa aactggtcag gagaaattgt atttcattgg a cattcactt    8340
ggcactacaa taggtatgtt tatgagggtc actgttaggt gtgtttttga g ggtcagttt    8400
tctcagagtc ttacaggagt tcacctttat gttggaataa acaactgtt a cttatagtg    8460
ccctcaattc cctgtcctct gctgggaata accctagtac tctaagtagc t gtgagcctg    8520
cagtgcacag actatatgta gggcaaacct ttcctgggtc tctggtcaca g cagcatatt    8580
gactacggtg atgcaatttc ccaggaataa catgtgttcc aaattcaaag a aataattcc    8640
acagagtaag tttctagatt ccctctgagc tgaaaaagta aaattcaatg c catggaata    8700
tggctgaaac ataataaatg tgcatcaatc atctctttct cacaacccaa a tgggatttt    8760
taaaaaataa aagggaaggg cttataccta tatttaaaca aattgaaaag g catggttat    8820
atttgtttgt gagttggaac acacaagctt actataataa atcaattgag c ttatctatt    8880
cagtgtgtga tttagtattt atgaaatagc aagtaaatgt aagcactatg t agaaatttc    8940
taaagttttt taagctgaca acttacttct taatttactt actttactta a tttacttta    9000
caatttactt tccaggtatt ttggaaagaa atcaataatc tagttccaag t aaaagttga    9060
aaggaaccca cactaataaa agctttgaat ttgtcattga acttccacta a agtttccaa    9120
ttttaagaga ataaatcatg tgaaagtgca atatttcagt ttagggaaat a ttttcatta    9180
tcaccactat catcagtaac aaacatatat tcattagtat tttagattga c aggcacttt    9240
ccaagctcag aacaggcagt tagcatcagt cagcatatac taaaaaagta t caagaact    9300
cataggagat caaaatgcc accaataggc aaataattac agtatctaac a cttattgag    9360
cattcgttat gtgtagggtc ttgtgttcag gaccttcccc acagtatctc c ctctgatct    9420
tcaaaacaac ccgaatgtta ttatccccat ctcatagaag aagaaacaca a gttcagaac    9480
acagattcaa accagatgta tctgatttca ccaataggt gtgtaaggat t ccggagaaa    9540
tggtgtagag aagaagaaat gactttagtt ggttttggaa agtgggtagg a cttagatat    9600
gctcttatac ttgatctgca aaaaaaaaa aaaaaccat ggagaatttg a ttatctgtg    9660
ctctgtgttt catttaggac ataaatattt ttagtgactg ttgtttgcat t ttggacaga    9720
gcaatttctg ttatgtaagg agcacccact ctttgtagga catttagtag g tcccagccc    9780
```

```
attaaacagg gctctgcagt cagcgtgacc ctcaaaaatc tcacctccac a catttccaa    9840 acaccctctg gggaagtact attcctgatt cagagtcttt ttatcaattg t tcagtcaat    9900 tatttcagtt cttcttttc tggccaagac agttttaatg ttccaacaag t gtttcagta    9960 cacacataca cacacacaca cacacacaca cacacacaca cacatgctag t ggaggccca   10020 ggaagggacc tctggaaacc aaattatatg gatattctcc ctagcctacc c agtgttgtg   10080 ctaatctcca tcctcacaga tatacaaagg ggtgcaatgc tactgctgaa a gagcaaagc   10140 aaatggagat gcctggtcct tactgggcca tcgtggatgc tagggaaagc c cctttcttt   10200 ttggaaacag ggaagagtct agagggttga aaaacaccca gtaagacact g ggagcagtg   10260 aaatttcatt ccatagtgag aaagaaaacc tgttagaata actgggtgat g ctgcagaaa   10320 gaaatcaatt cacctcctgt gactgattat ttgcttctgg aagctctgtg a ttcattctg   10380 gcatctcaga gttagggatg aaatgagaat gttgccagca tttaccccat g cttgggaag   10440 tttacacagc agtagctact ccagcagctt aaccatcacc tttcccctgc c aactactcc   10500 atttccccca atcaagtcaa actgtccata aatagaataa aataaaattg g agacttgag   10560 agcagagaag actgaaggca gattatcttt atagaataac tcagaagact t ccaattcat   10620 ccccagtat atcacgatag aaggaaaaaa tgactaagca gagccccaat t tgttagaa    10680 acattgcgta agtatttatt tttacaagat tgtcttatct cctgttctct c agggtttgt   10740 agccttttcc accatgcctg aactggcaca aagaatcaaa atgaattttg c cttgggtcc   10800 tacgatctca ttcaaatatc ccacgggcat ttttaccagg ttttttctac t tccaaattc   10860 cataatcaag gtaggctcct ttcaacaaaa tgtacctgag gatctcattt t ggatcataa   10920 atccttatta ttttcaaatc tactgtaaag taaaagtagg aaatttagat a aaatctata   10980 gaacttagac tctgtgggta tgtgcttgtg tatgtgtgtc cctgcgtgtg c gcatgtctg   11040 tgccatagta tctgcaggtt ctgtaataca atttactata caaggtcatc a gcaggctga   11100 gtatatgtca gaatttctag ctgaactgag tgctatatga caacaaggat t tttcttgtt   11160 ttcccaagtg ttttttgttc catttagtca ggtaggtcaa tgaattcaca t tgcccaaat   11220 gaaagacact tcaagttacc cataatcact gatgtgtcca attttgacat t agaaaaacc   11280 tgattaatat attccttcca atatggaaac ttgccctaat aactaaagct a agattccaa   11340 agcctaaatg tattacagct caagtattaa ttcaaatatt tattggttat t tttcaggag   11400 ttgaaaaagt catttggttg ccaattgtgg atttgggatt tatctatta a agggtttt    11460 tttttttttc tctttgcttt tgtttctcta caaaggtcat tgccacaatg a acacagcat   11520 ttaatcaaat tccagattgg cctttgaact tgggatgatg gataaaatgg a tttgggcca   11580 aaattgaagt caaggagacc agttagaata tcaaaataat tcatatataa g aaaatgaga   11640 cgttggtttg gggtagagtg gtaggaatga aaaaaattat ttgtgagcta a cacaaggaa   11700 taatttccat agggcctaat aatagttagg tctgataata ctatggtctg a taatagttt   11760 tattgtattg tttactgaga gcacaaatga tgtaacttcc ttattcaaga g cttttctag   11820 tttatttaaa aatgtgttga catcagttag gttttaatgt tttctatatt t ggacagtgt   11880 gagcaaacta atttgttaaa ttaaattcag agagagatac atctatctgt a aatacatat   11940 atgcgttgtt tgtgttgctc ttcctacata ggtcagctat aaggcaaata a tgttcctgg   12000 gttatctcag tttcacattt cccactgtca atattcctgc tacttttaag t cccatatcc   12060 tgctcttttc ttccgtcagt ttcccccaga agctccaaga ccccaccagg a atccccatc   12120
```

-continued

```
caagtttact ttcccaactc ctggaagttt caattgtgct gcctttgtga c attatcata   12180 tcttttctgt tcaatggttg cttctctttg gctcactgtt ctctactttt c agcctgaga   12240 gctggctaat ctgggacagt actcgaatgc agtgtacaca tgggtaacat g gaaaacccc   12300 gattttccct tatattcaag gtattatttg accttaagaa aaactgtttt a catttcata   12360 ccaattaatg agaaaaaaat attggcaagc actgactggg cagaatacag g gaagcttca   12420 ctatggagaa gtgaatttgg gattgagggc ctttattgca atctccttgt a aataatatt   12480 tgatactctt cctcatctgg agacacattc ctaagtaact tttcctgaat a atttggtct   12540 ccttgactga atcagtaagt acaaatagat ccccaagcat ggctctttcc t agaatgaaa   12600 gaaatgtcaa gaagtctgaa gatgattctt gaattttggt tttttgctat t gctatttgg   12660 gcttgttgtc cttgttgttg ctattgagtt gagctcctta tatattctgg t tactaatcc   12720 cttgtaatat ggatagtctg caaatatttt atctcattca aagataatta t tatttactt   12780 tcataggctg ttttttggtac caaaggtttc tttttagaag ataagaaaac g aagatagct   12840 tctaccaaaa tctgcaacaa taagatactc tggttgatat gtagcgaatt t atgtcctta   12900 tgggctggat ccaacaagaa aaatatgaat caggtatgta tgataattat a gggccattt   12960 gataccttaa gaaattccag ctttcctttg actcattttg atatatctat t tactgtata   13020 aattcatatg gtattccaaa cccttaaaga cagattttt tttgctttta a aaatgtttta   13080 tgggtatata atagttgtac atatttatga gacacatata ttttgatata a gcatacaat   13140 gtgtaatgac caaatcaggg taattgggat atccatcacc tcaagcattt a tcatttctt   13200 tttgttagag acattctaat ttgactcttc tagttatttt gaaatataca a tgaattatt   13260 gttaactata gtcatcctat tgtgcatgcc agactttagt ccttctaacg g tattttggt   13320 acccattaac caatgcctct ttatccttcc cccaccccta ctacctttcc c agcctctgg   13380 taaccatcat tcttctcact atctctataa ggtcagtttt ttttttaaact c ccctatatg   13440 agtgagaaca tgcagtattt gtcttttttgt gcctggctta tttcacttaa t gtaatgttc   13500 tctaatttca tccacattat tgcaaatgac atgatttcat tcttcttatg g ctgtctata   13560 tgtaccacat tttatttatc cactcatctg ttgatggaca cttaggctga t ttcatatct   13620 tggtcattgt gaatagtgct gtactaaaca tgggggtgca gatgtctctt c catggattg   13680 atttccttt ttttttctga atatagacct agcactggaa ttgctggatc a tatggtaat   13740 tctactttta gtttttgag gatccctcat actcttcccc atagttcctg t actaattta   13800 cattcctacc aacagtctgt gcaagagttc tcttttctcc acattcttgt c agcatccat   13860 tattgcctat cttttgata aaagctattt taactggagt gagatagtac t tcattgtag   13920 ttttagttcg catttctcta atgattagta atgttgaaca ttgtttttaa t gtacctctt   13980 ggctatttgt atgtcttctt ttgagaaatg tctactcaga tcttttgtcc a tttttaaat   14040 cagatttttt tttttgcaatt gagttatatg acctctttat atattctggt t actaatccc   14100 ttgtcagatg ggtagtttac aaatattttc tctcattcaa caggttcttt a gttcacttt   14160 gttgatggtc tcctttgctt tgcagaagct ttttagcttg acgtaatcta a tttgttcat   14220 gtttgctttg gttgcctgtg catttgaggg cttacctcaa attggcccag a ccaatgtcc   14280 cggagtgctt ctgtaatgtt tgtttttttag tagtttcata gttttaggtc t taaatgtgt   14340 ctttaatcca ttttgatttt gttttttgtat ctggcaagag atagagatct a atttcattc   14400 ttctgcatat ggatatctag ttttcccagc atcatttctt gtggaaattg t cctttgccc   14460 aatgtatgtt cttgatgcct ttgttgaaaa ttagttgact ataaatgtgt g gatttattt   14520
```

-continued

```
gtgggttctt tattctgttc cattggtcta tgtgtctgtt tttatgccag t atcatgcag   14580 ttttgattat tacaggtttg tagtataatt tgaagtcagg tcatgtgatg c ctccagctt   14640 tgttctttt  tctcagaatc ttatatttag aaaaacgtaa agactccaac a aaaaacctg   14700 ctagaactga taaacaaatt cattaaattt gcaggataca acatcaacat a caaaattca   14760 gcagcatttc aatatgccaa gagcaaataa tcttaaaaaa agaaagaaa a aaaaacaag   14820 aaataatccc atttataata gctacaaata aaataaaaca cctaggaata a accatacca   14880 aagaagtgaa agatttctac aatgaaaact ataaaacact gatgaaagaa t tgaaaatg    14940 acattaaaaa atggaaaggt attccatgtt catggattgc aagaatcaat a ttgttaaaa   15000 tgtccatatg atccaaaaca atctacagat tcaatgcaat ccctatcaaa a taccaatga   15060 cattcttcat tgaaataaaa aaaagcctaa aaatttaagt ggaaccatga a ggtagatgt   15120 ctgctataca tagaagatta agtactcaac aaaccttgaa tatgaagact g gggaagtga   15180 ataggcagct tcactcttct attccctggt gaaatttagg agaatggatg t tttataatg   15240 ggtagcagtt tcttacatgt tctcaatcag ccataactta ctacagtcaa t ttgaattta   15300 ttgcatttga atatattgga ttaaaaataa aatcctaaaa aaggagagaa g cacatataa   15360 acctgcgtct tatttcatgt gttccttct  ttgtgggtga cttttgtttt g aaataaaac   15420 ctgcaaaata acaggacagg gtggaaggga gatgggatcc cctctttatg a agaagcagc   15480 agtcctgttt tatcacctct tcattttctg ttattgagaa ttcaagaaga a ggaggagga   15540 agagttcaca tccacagact ggtgtggttg aatagttgtc tctactgtat t ccaaatagc   15600 agccaatgag gctgttacag tgaagccagt cccaagataa ttgttctgta c ccctattct   15660 ctaagaagct aaattgtgtt agactgaaac ccataaggaa ccattgttca a agttggctt   15720 gttcaaaagt aaagatttt  aatagtttct cttaattaga ttattttcta a gacatagaa   15780 ttatgattac tattttatct ctataatttt catctctata acgtttacaa a tactgaaat   15840 aacctttgga aaaaattggc ttttagcttt acttttgcaa tatttttattt t atccccata   15900 aaagcctagg aaattggtac tatgacttt  agtatgttca tttaatagat g aaaacacag   15960 aaactcaaag atgttaaata tggtggccaa gttcacaaag ctgatcatta a caacaacag   16020 ggcctgaact cctggttttc tgatttaatc tgtgacagtg cacctgggtg c gcatgcatg   16080 catcaccccc acacttgcac atagaacctt tcctagttgg ctttgctcca t gatgaccat   16140 tactgttcct tctacttcaa aataagcaaa ttatcctaca gattcagagc t ggtacaggt   16200 gtgctgtcaa gcagcccatt ccattagtca gcttgtggtt cactcacatt a aagtattga   16260 cctaaatggt atatttatct agataattct accttgttat tttcaaagcc c cagtcttgt   16320 ttgctaattc tgtgcatcat ttttctctga ttctgaaagg caaaattttg t tgggcaatt   16380 gctgtaatat gagttttatc tcctttagag tcgaatggat gtgtatatgt c acatgctcc   16440 cactggttca tcagtacaca acattctgca tataaaacag gtagagtctt a gtcatggaa   16500 aaccattcca atccttattt tcaatatatt taaaagaca gaattgaccc t gttaacagg   16560 cctaccctaa gaatcttaag agcttgcttc cagtttgtcc ttgctgcctt c tgtatgcct   16620 tgatttccct ggaatttaag agaaaggatg ttatggtaca gaccaagtag a tgacataaa   16680 tgaacaccac cttaaatcag agttttaaaa ataggccctg aactgaagca a gaggtaaac   16740 tagggaagcc tcaggagaac tgagacttct ccagagagaa gtatctggga t ttaacttct   16800 ttctaatgag gcttggtttt ccatgaactt ttccctttaaa ccaagggggg t attgctcat   16860
```

```
ctttctgttg agccccattt gtcataattg taaaatgggt ggttacatcc t tctggtgat  16920 ctaggagccc tattttcgtc ctagcataca gcattttcct aaaatttgct g ttagctttc  16980 atgattctta ccctaactat tcttttccta aaaacatttt gtttcagctt t accactctg  17040 atgaattcag agcttatgac tggggaaatg acgctgataa tatgaaacat t acaatcagg  17100 tgagctattt acagtaaccc cagcatgctg attttgataa attataataa a aaattattt  17160 gagggtggaa agactcctac ctgtcatttg gtggcattta tactgataga a cttttttt  17220 aaaaaaattt taattttaat tttaatttat ttcagaaaat ttataaatta a agaagcata  17280 tacaaagaaa cttacatcat gtgtaatcct tccatccaga gataactaga t gtactaaca  17340 ttttggtgta tttattccaa ttttctcagt attatattgc ttttagacaa c ttttaatct  17400 ttctatttta cttaagctat agtaagagat aactaatata actgagggat t tttaaatgc  17460 atttttaatg gctacataat agaaattatt tcataaaaat ctttacagca t aaatgaata  17520 tacacttttt aataccaaca gaaaaattag aattccatat gaaagttgaa t aagtattac  17580 ccaacattga agacttgggt cgtaaggcat ctttctccat atagctttat g acataaaaa  17640 tctgtagcct tgtttagcac cgtactttta attaatcctg tcaccatttt t ctgttctca  17700 tagccagggg cttggcttat aagtatgaac taagcaaact aaattaaatt g ttttaagta  17760 ttttcccagg ctatcatatt ttaagctatt tactggtgca actatagatt a ttaataagt  17820 tgtttctgag gatcaaaaca atcagactaa tcaatttctc aataatgaat t ggcctgtta  17880 gaggaataat tctactaatc cttaaaacca ctacaagaga tagaccatgt a tattttatt  17940 tatttttaaa aataagttta agatgtgatt tacatacaag aacattacta a ttttgtgtg  18000 tcccatttaa taagttttga caaatatatt tatttgtgta accacaccac a atctaaata  18060 taggacgttt atatcaccac taaaagtttt tttcctgctc ctgagactat t tatagacac  18120 aaatgcgtgt atttgcaaat gcttagaaaa ggtctagaaa aaaaaacagt a aatgttaaa  18180 gtggttatct tcagagagaa gaaagaagaa aagaagtgga tggacatgaa a cagtaaagg  18240 accctcattt tggactttac atatgtctgt tttcttccat tattttgaat a aacatgcta  18300 tatttataaa ttatttacat ttacaagaaa atgaaacaaa tcaacacgc a cattcaaga  18360 tcattatggt caagtactaa agtatgtgag agtgttaatg tccttagaat t tggccacag  18420 ttagctggtc ctactctgct ccaagccggt cctattttgt gaattaatct c atttgatgc  18480 caatttttat tacattctct ccaaaaaact agtctcaaca gtttgctctc t cctcaagtt  18540 cacagcatta tctctgctat atctatattt tattgagtat aagagaatta a cccatgtaa  18600 gctccatgag ggtagggatt tctcatcgtt ttgttcacca gtgttttctc a tcttgaaga  18660 gtacatgaca attactgggc tcccagtatc tatgtgttgc attaatgaaa t ttcttaact  18720 ttaatctacc tcaaaatgtc tctatcttct tgattctctc cttcctttct c tatcagaaa  18780 atgatggtcc tcttatttc caagttattc cggtcctgtg cccttgatcc c atctcttct  18840 cacttcccct tccttcctgc ctccattctc ctgtcccctta tgaaaaacaa g caagaccat  18900 caattctatc aagttatcat tatgtcactc tgttcttatc aacatatttt t agtattgaa  18960 gagggcttct tctacttact cctgaacctt gtacaatgta gttaggtct t catcttttt  19020 atcatagcta cctatttaa agtcacccat ggcttttaat tgccaaattc a atggcctat  19080 cttcaccttt tgaaatgtgt tatgttcgtt accacagtct ccttgaaact c agtcccctg  19140 acttggactt ccataacaca atgatttctg attttccttc tgtttgtgat t gttcctttt  19200 gtcccaggca ctggctactc caccttccac ctctctgaaa tcattagcat t ccccaagga  19260
```

```
ttcttcaaaa ctctctttct tccttggaga agtcagcata gctttaattt g gaccatttc    19320
tatggcttat ctagatttt tcaggacttg ccttcaacct attctttctg t aggtgattc     19380
cattaactgt tgcccatatg gtagtccgaa gacagacctc cgagaaatga c ccttgtctc    19440
caaaacttcc gcaatatgtc caaatttcct agcctgacat tcagactttg a ttatctgcc   19500
tccaagttta tatcctatca tattccttta tatattctgt tctccaggta c actgggaag   19560
cttgccattc ctgatcatag cctacaaact cttcctgcct cccactcacc c tcatctctg   19620
ctgtcaaaat gcaaccttcc ctcaagagtc atttcacagg acccctcttt c tatgaagcc   19680
ctcaggtgga aataattttt tgccttttt tccatttat ttttggagtg t ttatggcat      19740
ttaacatacc ttactttgta tacaaatatt tgccttgctc cctcttttgc a aatttctta   19800
aaggtagaga ccattgtatg ttttcttcat atgttgctgg tgcctaacag a actatggcc   19860
attgtccaca ttcatttagc agcctttgta gttattgctt tgaggagctt c ctctcatga   19920
atgcccttgc tttctctccc acagagtcat cccctatat atgacctgac t gccatgaaa    19980
gtgcctactg ctatttgggc tggtggacat gatgtcctcg taacacccca g gatgtggcc   20040
aggatactcc ctcaaatcaa gagtcttcat tactttaagc tattgccaga t tggaaccac   20100
tttgattttg tctggggcct cgatgcccct caacggatgt acagtgaaat c atagcttta   20160
atgaaggcat attcctaaat gcaatgcatt tactttcaa ttaaaagttg c ttccaagcc    20220
cataagggac tttagaaaaa atggtaacca acaatgaggt tgtcccccag c accctgggg   20280
gagatgcaca gtggagtctg ttttccaagt caattgtgtt agtgttattt a tgtttagag   20340
acatctttgc atgggaccat ctacaggtcc ttataaacaa tgaggtagat t aggcaaaaa   20400
gataaacaag ttgctactct atctggcatt taagtctaat taaattgtaa t tttagggc    20460
ataccatgaa gtatagaaat gtctgaagct tcaaaggaac agtgaaattc c tttaaggtc   20520
ctatatggaa acctctgttg tcattttatt tatatggatt gctatggcaa t ggacagagt   20580
gtgggattag gaggagggcc tgtaacttct ttataaagt ttcttagcta t cctgaagat    20640
gtatagacat ttttactttt ttaggtattt tcaacatcag aaattcaaaa a agtccccaa   20700
agattcttcc agagaagccc tcttttctta caatcttatc cctggctatc t gcgtaaacg   20760
gaatcttgaa cccataatag gatacatgta taaaatcttc cttattaaag c agaaataaa   20820
ttgtacagca tcaatatcat tttataatca tagggaggct tctttgttta g catgtaatg   20880
cccccttac aggcttttg ttctttgagg ggtttgaaca ttccatgaaa a actgacaga     20940
taggaaactg acaataaaag attgagctaa agatggaagc agaaagtact a ggctagata   21000
gtctctaaac attaagtatt ttcttcctcc atcttaaaag caatgagaag c caccaaaat   21060
attttaccta atggaaacct gattgccgca tttttgtaac caccactttg c tgctacat    21120
agagaatgga ttagaagatg ccaacaaaag attctgagca agtctgtaaa t ctgatcaag   21180
tgttctgatg caggctgata tccttctgtg ctaagagaga tgatccttgg a aaatccaga   21240
gccagctcca taatactttc ctgctctgct ggcaaatcca caagctgctg g ccctggag    21300
ccattcttct ctcaaaacta gcattcatca atttaatgta tacgtattga t ggggaataa   21360
tggtcactat gaaaaccatg tgataatatg gaaaatacc catgatataa t gttatgtga    21420
agagaagaaa atgaaactgg tagaactatg tgattgcaaa tatatacaaa t attaaaaca   21480
attatatgac tttataaaat atttgtatat aatgaaaact gaagcaatat a aaaataaa    21540
attagttgtg tcagggtagt aacatgatga gtgattaata gttttaattt t ttaatatag   21600
```

-continued

```
taatgacata atgttacaac ttgtccaaat ctcacaaaca taatattcag t aaaggaaga  21660 taaacataaa agaatacata ttttattata cattttatg taggctaatt g atggttctg   21720 aaagccttaa aaagcttact tttaggagga gaatcatgcc ttggaggact c tagggtcca  21780 gaaaaatgtc ctaatactag agctaggtgc agtcagatta attataatac a tttcattat  21840 tttgtctgga ataccaagat gacttccaag caggaatgga gtctagcaac a ctttactga  21900 tggggaactt ggccacagac ttgtaataca aattttgga tatgttgaca a tgtttctcc   21960 ttatttttct tacttataca aagcaagaaa tttggctcac aaccttgaaa c agacttacc  22020 aggttcctcc agtttcccaa gcctcaatat ctcattgcta tttttaa               22067
```

<210> SEQ ID NO 4
<211> LENGTH: 392
<212> TYPE: PRT
<213> ORGANISM: Human

<400> SEQUENCE: 4

```
Met Arg Phe Leu Gly Leu Val Val Cys Leu V al Leu Trp Thr Leu His
 1               5                  10                  15

Ser Glu Gly Ser Gly Gly Lys Leu Thr Ala V al Asp Pro Glu Thr Asn
            20                  25                  30

Met Asn Val Ser Glu Ile Ile Ser Tyr Trp G ly Phe Pro Ser Glu Glu
        35                  40                  45

Tyr Leu Val Glu Thr Glu Asp Gly Tyr Ile L eu Cys Leu Asn Arg Ile
    50                  55                  60

Pro His Gly Arg Lys Asn His Ser Asp Lys G ly Pro Lys Pro Val Val
65                  70                  75                  80

Phe Leu Gln His Gly Leu Leu Ala Asp Ser S er Asn Trp Val Thr Asn
                85                  90                  95

Leu Ala Asn Ser Ser Leu Gly Phe Ile Leu A la Asp Ala Gly Phe Asp
            100                 105                 110

Val Trp Met Gly Asn Ser Arg Gly Asn Thr T rp Ser Arg Lys His Lys
        115                 120                 125

Thr Leu Ser Val Ser Gln Asp Glu Phe Trp A la Phe Ser Tyr Asp Glu
    130                 135                 140

Met Ala Lys Tyr Asp Leu Pro Ala Ser Ile A sn Phe Ile Leu Asn Lys
145                 150                 155                 160

Thr Gly Gln Glu Gln Val Tyr Tyr Val Gly H is Ser Gln Gly Thr Thr
                165                 170                 175

Ile Gly Phe Ile Ala Phe Ser Gln Ile Pro G lu Leu Ala Lys Arg Ile
            180                 185                 190

Lys Met Phe Phe Ala Leu Gly Pro Val Ala S er Val Ala Phe Cys Thr
        195                 200                 205

Ser Pro Met Ala Lys Leu Gly Arg Leu Pro A sp His Leu Ile Lys Asp
    210                 215                 220

Leu Phe Gly Asp Lys Glu Phe Leu Pro Gln S er Ala Phe Leu Lys Trp
225                 230                 235                 240

Leu Gly Thr His Val Cys Thr His Val Ile L eu Lys Glu Leu Cys Gly
                245                 250                 255

Asn Leu Cys Phe Leu Leu Cys Gly Phe Asn G lu Arg Asn Leu Asn Met
            260                 265                 270

Ser Arg Val Asp Val Tyr Thr Thr His Ser P ro Ala Gly Thr Ser Val
        275                 280                 285

Gln Asn Met Leu His Trp Ser Gln Ala Val L ys Phe Gln Lys Phe Gln
```

```
                    290                 295                 300
Ala Phe Asp Trp Gly Ser Ser Ala Lys Asn T yr Phe His Tyr Asn Gln
305                 310                 315                 320

Ser Tyr Pro Pro Thr Tyr Asn Val Lys Asp M et Leu Val Pro Thr Ala
                325                 330                 335

Val Trp Ser Gly Gly His Asp Trp Leu Ala A sp Val Tyr Asp Val Asn
                340                 345                 350

Ile Leu Leu Thr Gln Ile Thr Asn Leu Val P he His Glu Ser Ile Pro
                355                 360                 365

Glu Trp Glu His Leu Asp Phe Ile Trp Gly L eu Asp Ala Pro Trp Arg
                370                 375                 380

Leu Tyr Asn Lys Ile Ile Asn Leu
385                 390
```

That which is claimed is:

1. An isolated nucleic acid molecule encoding a lysosomal acid lipase protein consisting of a nucleotide sequence selected from the group consisting of:
   (a) a nucleotide sequence that encodes a protein comprising the an amino acid sequence of SEQ ID NO:2;
   (b) a nucleic acid molecule consisting of the nucleic acid sequence of SEQ ID NO:1; and
   (c) a nucleic add molecule consisting of the nucleic acid sequence of SEQ ID NO:3.

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the peptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

10. An isolated nucleic acid molecule consisting of a nucleotide sequence that is completely complementary to a nucleotide sequence of claim 1.

11. An isolated nucleic acid molecule encoding a lysosomal acid lipase protein consisting of a nucleotide sequence that has at least 95% homology with a nucleotide sequence of claim 1.

* * * * *